US 12,251,088 B2

(12) United States Patent
Ye et al.

(10) Patent No.: US 12,251,088 B2
(45) Date of Patent: Mar. 18, 2025

(54) LOW-FRICTION, SMALL PROFILE MEDICAL TOOLS HAVING EASY-TO-ASSEMBLE COMPONENTS

(71) Applicant: Intuitive Surgical Operations, Inc., Sunnyvale, CA (US)

(72) Inventors: Zhou Ye, Santa Clara, CA (US); Harsukhdeep Ratia, Foster City, CA (US); Alain Sadaka, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 318 days.

(21) Appl. No.: 17/869,045

(22) Filed: Jul. 20, 2022

(65) Prior Publication Data

US 2022/0354474 A1    Nov. 10, 2022

Related U.S. Application Data

(63) Continuation of application No. 16/971,982, filed as application No. PCT/US2019/020653 on Mar. 5, 2019, now Pat. No. 11,439,376.

(Continued)

(51) Int. Cl.
*A61B 17/00* (2006.01)
*A61B 17/29* (2006.01)
(Continued)

(52) U.S. Cl.
CPC ........ *A61B 17/00234* (2013.01); *A61B 34/35* (2016.02); *A61B 2017/00327* (2013.01);
(Continued)

(58) Field of Classification Search
CPC ............. A61B 17/00234; A61B 17/29; A61B 17/320016; A61B 18/1445;
(Continued)

(56) References Cited

U.S. PATENT DOCUMENTS 2,186,181 A    1/1940    Gustav et al.
3,618,420 A    11/1971   Horwitt et al.
(Continued)

FOREIGN PATENT DOCUMENTS

CA    2853431 A1    5/2013
CN    102458551 A   5/2012
(Continued)

OTHER PUBLICATIONS

Extended European Search Report for EP Application No. 19764084.0, mailed Oct. 27, 2021, 9 pages.
(Continued)

*Primary Examiner* — Mohamed G Gabr

(57) ABSTRACT

A low-friction medical device includes a first link, a second link, and a tension member. The first link is coupled to an instrument shaft and a first guide path is defined in the first link. The second link is rotatable relative to the first link through an angular range. A distal end portion of the second link is rotatably coupled to a tool member. A curved guide path is defined within the second link between the tool member and the first guide path. A curved guide surface of the second link defines a portion of the second guide path. A first portion of the tension member is parallel to a centerline of the first guide path, and a second portion is coupled to the tool member. A third portion of the tension member between the first and second portions is in contact with the curved guide surface throughout a portion of the angular range.

24 Claims, 46 Drawing Sheets

Related U.S. Application Data

(60) Provisional application No. 62/639,631, filed on Mar. 7, 2018.

(51) Int. Cl.
*A61B 17/32* (2006.01)
*A61B 18/00* (2006.01)
*A61B 34/00* (2016.01)
*A61B 34/30* (2016.01)
*A61B 34/35* (2016.01)

(52) U.S. Cl.
CPC ..... *A61B 2017/00845* (2013.01); *A61B 17/29* (2013.01); *A61B 17/320016* (2013.01); *A61B 2018/00595* (2013.01); *A61B 2034/302* (2016.02); *A61B 2034/715* (2016.02)

(58) Field of Classification Search
CPC ........... A61B 2017/00327; A61B 2017/00477; A61B 2017/00845; A61B 2018/00595; A61B 2034/302; A61B 2034/305; A61B 2034/715; A61B 34/35; A61B 34/71; A61B 34/76

See application file for complete search history.

(56) References Cited

U.S. PATENT DOCUMENTS

| | | | |
|---|---|---|---|
| 4,341,144 A | 7/1982 | Milne | |
| 5,325,845 A | 7/1994 | Adair | |
| 5,396,900 A | 3/1995 | Slater et al. | |
| 5,482,054 A | 1/1996 | Slater et al. | |
| 5,624,398 A | 4/1997 | Smith et al. | |
| 5,784,542 A | 7/1998 | Ohm et al. | |
| 5,792,135 A | 8/1998 | Madhani et al. | |
| 5,807,377 A | 9/1998 | Madhani et al. | |
| 5,855,583 A | 1/1999 | Wang et al. | |
| 5,876,325 A | 3/1999 | Mizuno et al. | |
| 5,899,914 A | 5/1999 | Zirps et al. | |
| 5,916,146 A | 6/1999 | Allotta et al. | |
| 6,007,550 A | 12/1999 | Wang et al. | |
| 6,197,017 B1 | 3/2001 | Brock et al. | |
| 6,206,903 B1 | 3/2001 | Ramans | |
| 6,309,397 B1 | 10/2001 | Julian et al. | |
| 6,331,181 B1 | 12/2001 | Tierney et al. | |
| 6,371,952 B1 | 4/2002 | Madhani et al. | |
| 6,394,998 B1 | 5/2002 | Wallace et al. | |
| 6,491,626 B1 | 12/2002 | Stone et al. | |
| 6,491,701 B2 | 12/2002 | Tierney et al. | |
| 6,554,844 B2 | 4/2003 | Lee et al. | |
| 6,676,684 B1 | 1/2004 | Morley et al. | |
| 6,685,698 B2 | 2/2004 | Morley et al. | |
| 6,767,349 B2 | 7/2004 | Ouchi | |
| 6,817,974 B2 | 11/2004 | Cooper et al. | |
| 6,840,938 B1 | 1/2005 | Morley et al. | |
| 6,843,793 B2 | 1/2005 | Brock et al. | |
| 6,949,106 B2 | 9/2005 | Brock et al. | |
| 6,969,385 B2 | 11/2005 | Moreyra | |
| 6,994,708 B2 | 2/2006 | Manzo | |
| 7,083,571 B2 | 8/2006 | Wang et al. | |
| 7,090,683 B2 | 8/2006 | Brock et al. | |
| 7,125,403 B2 | 10/2006 | Julian et al. | |
| 7,147,650 B2 | 12/2006 | Lee | |
| 7,169,141 B2 | 1/2007 | Brock et al. | |
| 7,214,230 B2 | 5/2007 | Brock et al. | |
| 7,316,681 B2 | 1/2008 | Madhani et al. | |
| 7,320,700 B2 | 1/2008 | Cooper et al. | |
| 7,338,505 B2 | 3/2008 | Belson | |
| 7,338,513 B2 | 3/2008 | Lee et al. | |
| 7,371,210 B2 | 5/2008 | Brock et al. | |
| 7,608,083 B2 | 10/2009 | Lee et al. | |
| 7,682,307 B2 | 3/2010 | Danitz et al. | |
| 7,699,835 B2 | 4/2010 | Lee et al. | |
| 7,785,252 B2 | 8/2010 | Danitz et al. | |
| 7,824,401 B2 | 11/2010 | Manzo et al. | |
| 7,935,130 B2 | 5/2011 | Williams | |
| 8,142,421 B2 | 3/2012 | Cooper et al. | |
| 8,142,447 B2 | 3/2012 | Cooper et al. | |
| 8,245,595 B2 | 8/2012 | Milenkovic | |
| 8,323,297 B2 | 12/2012 | Hinman et al. | |
| 8,347,757 B2 | 1/2013 | Duval | |
| 8,479,969 B2 | 7/2013 | Shelton, IV | |
| 8,540,748 B2 | 9/2013 | Murphy et al. | |
| 8,551,115 B2 | 10/2013 | Steger et al. | |
| 8,578,810 B2 | 11/2013 | Donhowe | |
| 8,602,288 B2 | 12/2013 | Shelton, IV et al. | |
| 8,771,270 B2 | 7/2014 | Burbank | |
| 8,800,838 B2 | 8/2014 | Shelton, IV | |
| 8,821,480 B2 | 9/2014 | Burbank | |
| 8,939,963 B2 | 1/2015 | Rogers et al. | |
| 9,028,494 B2 | 5/2015 | Shelton, IV et al. | |
| 9,055,961 B2 | 6/2015 | Manzo et al. | |
| 9,078,684 B2 | 7/2015 | Williams | |
| 9,186,221 B2 | 11/2015 | Burbank | |
| 9,198,729 B2 | 12/2015 | Rogers | |
| 9,204,923 B2 | 12/2015 | Manzo et al. | |
| 9,232,979 B2 | 1/2016 | Parihar et al. | |
| 9,259,275 B2 | 2/2016 | Burbank | |
| 9,358,031 B2 | 6/2016 | Manzo | |
| 9,533,122 B2 | 1/2017 | Weitzner et al. | |
| 9,615,846 B2 | 4/2017 | Prestel | |
| 9,962,228 B2 | 5/2018 | Schuh et al. | |
| 10,130,366 B2 | 11/2018 | Shelton, IV et al. | |
| 10,219,874 B2 | 3/2019 | Yu et al. | |
| 10,285,763 B2 | 5/2019 | Vale et al. | |
| 10,299,873 B2 | 5/2019 | Hares et al. | |
| 10,499,891 B2 | 12/2019 | Chaplin et al. | |
| 10,524,870 B2 | 1/2020 | Saraliev et al. | |
| 10,624,703 B2 | 4/2020 | Chaplin et al. | |
| 10,682,141 B2 | 6/2020 | Moore et al. | |
| 10,758,298 B2 | 9/2020 | Felder et al. | |
| 10,786,320 B2 | 9/2020 | Adams et al. | |
| 10,792,116 B2 | 10/2020 | Haraguchi et al. | |
| 10,813,706 B2 | 10/2020 | Chaplin et al. | |
| 11,020,112 B2 | 6/2021 | Shelton, IV et al. | |
| 11,045,270 B2 | 6/2021 | Shelton, IV et al. | |
| 11,109,928 B2 | 9/2021 | Schuh | |
| 11,129,686 B2 | 9/2021 | Chaplin et al. | |
| 11,272,977 B2 | 3/2022 | Manzo et al. | |
| 11,439,376 B2 * | 9/2022 | Ratia | A61B 34/71 |
| 11,717,364 B2 | 8/2023 | Penny et al. | |
| 2001/0025134 A1 | 9/2001 | Bon et al. | |
| 2002/0111621 A1 | 8/2002 | Wallace et al. | |
| 2004/0260198 A1 | 12/2004 | Rothberg et al. | |
| 2004/0266574 A1 | 12/2004 | Jinno et al. | |
| 2005/0240178 A1 | 10/2005 | Morley et al. | |
| 2006/0074415 A1 | 4/2006 | Scott et al. | |
| 2006/0131908 A1 | 6/2006 | Tadano | |
| 2006/0190034 A1 | 8/2006 | Nishizawa et al. | |
| 2007/0158385 A1 | 7/2007 | Hueil et al. | |
| 2007/0208375 A1 | 9/2007 | Nishizawa et al. | |
| 2007/0246508 A1 | 10/2007 | Green | |
| 2008/0046122 A1 | 2/2008 | Manzo et al. | |
| 2008/0065102 A1 | 3/2008 | Cooper | |
| 2008/0065105 A1 | 3/2008 | Larkin et al. | |
| 2008/0125794 A1 | 5/2008 | Brock et al. | |
| 2008/0196533 A1 | 8/2008 | Bergamasco et al. | |
| 2008/0255421 A1 | 10/2008 | Hegeman et al. | |
| 2009/0088774 A1 | 4/2009 | Swarup et al. | |
| 2009/0171348 A1 | 7/2009 | Guo et al. | |
| 2009/0198272 A1 | 8/2009 | Kerver et al. | |
| 2009/0326530 A1 | 12/2009 | Orban, III et al. | |
| 2010/0011900 A1 | 1/2010 | Burbank et al. | |
| 2010/0011901 A1 * | 1/2010 | Burbank | A61B 34/30 74/490.06 |
| 2010/0030238 A1 | 2/2010 | Viola et al. | |
| 2010/0198218 A1 | 8/2010 | Manzo | |
| 2010/0198253 A1 | 8/2010 | Jinno et al. | |
| 2011/0295269 A1 | 12/2011 | Swensgard et al. | |
| 2011/0295270 A1 | 12/2011 | Giordano et al. | |
| 2012/0330287 A1 | 12/2012 | Yim | |
| 2013/0123783 A1 | 5/2013 | Marczyk et al. | |
| 2013/0144395 A1 | 6/2013 | Stefanchik et al. | |

(56) References Cited

U.S. PATENT DOCUMENTS

| | | |
|---|---|---|
| 2013/0239735 A1 | 9/2013 | Solomon et al. |
| 2013/0304084 A1 | 11/2013 | Beira et al. |
| 2013/0345718 A1 | 12/2013 | Crawford et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0073856 A1 | 3/2014 | Stein et al. |
| 2014/0100558 A1 | 4/2014 | Schmitz et al. |
| 2014/0114327 A1 | 4/2014 | Boudreaux et al. |
| 2014/0257331 A1 | 9/2014 | Kim et al. |
| 2014/0276956 A1 | 9/2014 | Crainich et al. |
| 2015/0005786 A1 | 1/2015 | Burbank |
| 2015/0150635 A1 | 6/2015 | Kilroy et al. |
| 2015/0157355 A1 | 6/2015 | Price et al. |
| 2015/0313676 A1 | 11/2015 | Deodhar |
| 2016/0051274 A1 | 2/2016 | Howell et al. |
| 2016/0051318 A1 | 2/2016 | Manzo et al. |
| 2016/0058443 A1 | 3/2016 | Yates et al. |
| 2016/0143688 A1 | 5/2016 | Orban, III et al. |
| 2016/0287279 A1 | 10/2016 | Bovay et al. |
| 2016/0287346 A1 | 10/2016 | Hyodo et al. |
| 2016/0296219 A1 | 10/2016 | Srivastava et al. |
| 2016/0302819 A1 | 10/2016 | Stulen et al. |
| 2016/0303743 A1 | 10/2016 | Rockrohr |
| 2016/0361123 A1 | 12/2016 | Hares et al. |
| 2017/0007242 A1 | 1/2017 | Shelton, IV et al. |
| 2017/0007345 A1 | 1/2017 | Smith et al. |
| 2017/0042562 A1 | 2/2017 | Moody et al. |
| 2017/0095922 A1 | 4/2017 | Licht et al. |
| 2017/0120457 A1 | 5/2017 | Saraliev et al. |
| 2017/0165010 A1 | 6/2017 | Chaplin et al. |
| 2017/0165017 A1 | 6/2017 | Chaplin et al. |
| 2017/0234411 A1 | 8/2017 | Dewaele et al. |
| 2017/0252096 A1 | 9/2017 | Felder et al. |
| 2017/0265954 A1 | 9/2017 | Burbank et al. |
| 2018/0116708 A1 | 5/2018 | Manzo et al. |
| 2018/0200895 A1 | 7/2018 | Kan |
| 2018/0206904 A1 | 7/2018 | Felder et al. |
| 2019/0090940 A1 | 3/2019 | Manzo et al. |
| 2019/0094084 A1 | 3/2019 | Swinehart et al. |
| 2019/0099227 A1 | 4/2019 | Rockrohr |
| 2019/0099231 A1 | 4/2019 | Bruehwiler et al. |
| 2019/0159846 A1 | 5/2019 | Yates et al. |
| 2019/0167368 A1 | 6/2019 | Yoshii |
| 2019/0192137 A1 | 6/2019 | Shelton, IV et al. |
| 2019/0223960 A1 | 7/2019 | Chaplin et al. |
| 2019/0231374 A1 | 8/2019 | Kimura et al. |
| 2019/0239877 A1 | 8/2019 | Ragosta et al. |
| 2019/0239967 A1 | 8/2019 | Ragosta et al. |
| 2019/0328467 A1 | 10/2019 | Waterbury et al. |
| 2019/0336228 A1 | 11/2019 | Blumenkranz et al. |
| 2019/0380800 A1 | 12/2019 | Jogasaki et al. |
| 2020/0015807 A1 | 1/2020 | Limon et al. |
| 2020/0022765 A1 | 1/2020 | Limon et al. |
| 2020/0054405 A1 | 2/2020 | Schuh et al. |
| 2020/0054408 A1 | 2/2020 | Schuh et al. |
| 2020/0093554 A1 | 3/2020 | Schuh et al. |
| 2020/0138531 A1 | 5/2020 | Chaplin |
| 2020/0170734 A1 | 6/2020 | Saraliev et al. |
| 2020/0197112 A1 | 6/2020 | Chin et al. |
| 2020/0352660 A1 | 11/2020 | Prisco |
| 2020/0390430 A1 | 12/2020 | Ratia et al. |
| 2020/0390507 A1 | 12/2020 | Sadaka |
| 2020/0397522 A1 | 12/2020 | Ratia et al. |
| 2021/0022819 A1 | 1/2021 | Duque et al. |
| 2021/0244427 A1 | 8/2021 | Lee et al. |
| 2021/0290322 A1 | 9/2021 | Traina |
| 2022/0022943 A1 | 1/2022 | Manzo et al. |

FOREIGN PATENT DOCUMENTS

| | | |
|---|---|---|
| CN | 102488554 A | 6/2012 |
| CN | 104116547 A | 10/2014 |
| CN | 106714721 A | 5/2017 |
| CN | 113262051 A | 8/2021 |
| EP | 1847289 A2 | 10/2007 |
| EP | 2362285 A2 | 8/2011 |
| EP | 2415418 A1 | 2/2012 |
| EP | 2548529 A1 | 1/2013 |
| EP | 2783643 A1 | 10/2014 |
| EP | 3100666 A1 | 12/2016 |
| EP | 3103374 A1 | 12/2016 |
| FR | 3016543 A1 | 7/2015 |
| GB | 191012759 A | 3/1911 |
| GB | 2590881 A | 7/2021 |
| JP | 2002503131 A | 1/2002 |
| JP | 2002200091 A | 7/2002 |
| JP | 2004337994 A | 12/2004 |
| JP | 2006061364 A | 3/2006 |
| KR | 100778387 B1 | 11/2007 |
| WO | WO-2009123891 A1 | 10/2009 |
| WO | WO-2010081050 A1 | 7/2010 |
| WO | WO-2011097095 A1 | 8/2011 |
| WO | WO-2012006306 A2 | 1/2012 |
| WO | WO-2013181522 A1 | 12/2013 |
| WO | WO-2014025204 A1 | 2/2014 |
| WO | WO-2014151952 A1 | 9/2014 |
| WO | WO-2016025132 A1 | 2/2016 |
| WO | WO-2016161449 A1 | 10/2016 |
| WO | WO-2016189284 A1 | 12/2016 |
| WO | WO-2017064301 A1 | 4/2017 |
| WO | WO-2017064303 A1 | 4/2017 |
| WO | WO-2017064306 A1 | 4/2017 |
| WO | WO-2017098273 A1 | 6/2017 |
| WO | WO-2017136710 A2 | 8/2017 |
| WO | WO-2017188851 A1 | 11/2017 |
| WO | WO-2017209695 A1 | 12/2017 |
| WO | WO-2018049211 A1 | 3/2018 |
| WO | WO-2018069679 A1 | 4/2018 |
| WO | WO-2018094191 A1 | 5/2018 |
| WO | WO-2018123024 A1 | 7/2018 |
| WO | WO-2018179140 A1 | 10/2018 |
| WO | WO-2018234795 A1 | 12/2018 |
| WO | WO-2018234814 A1 | 12/2018 |
| WO | WO-2019118334 A1 | 6/2019 |
| WO | WO-2019118336 A1 | 6/2019 |
| WO | WO-2019118337 A1 | 6/2019 |
| WO | WO-2019173266 A1 | 9/2019 |
| WO | WO-2019173267 A1 | 9/2019 |
| WO | WO-2019173268 A1 | 9/2019 |
| WO | WO-2023177565 A1 | 9/2023 |

OTHER PUBLICATIONS

Extended European Search Report for Application No. 19764858.7, mailed on Nov. 2, 2021, 10 pages.

International Search Report and Written Opinion for Application No. PCT/US2019/020653, mailed on Jun. 11, 2019, 9 pages (ISRG10610/PCT).

International Search Report and Written Opinion for Application No. PCT/US2019/020654, mailed on Jun. 10, 2019, 7 pages (ISRG10611/PCT).

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for EP Application No. 19764084.0, mailed Feb. 13, 2024.

* cited by examiner

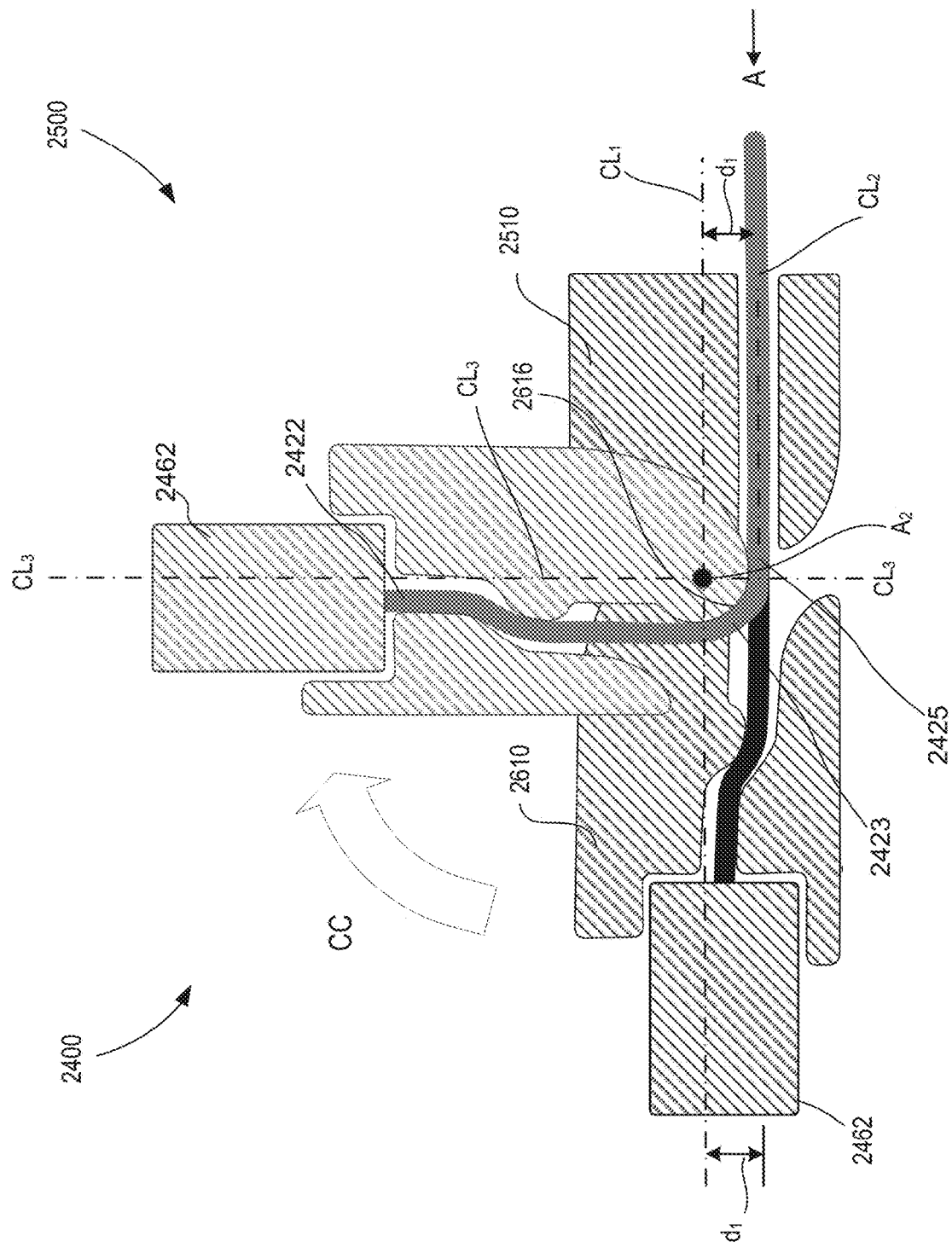

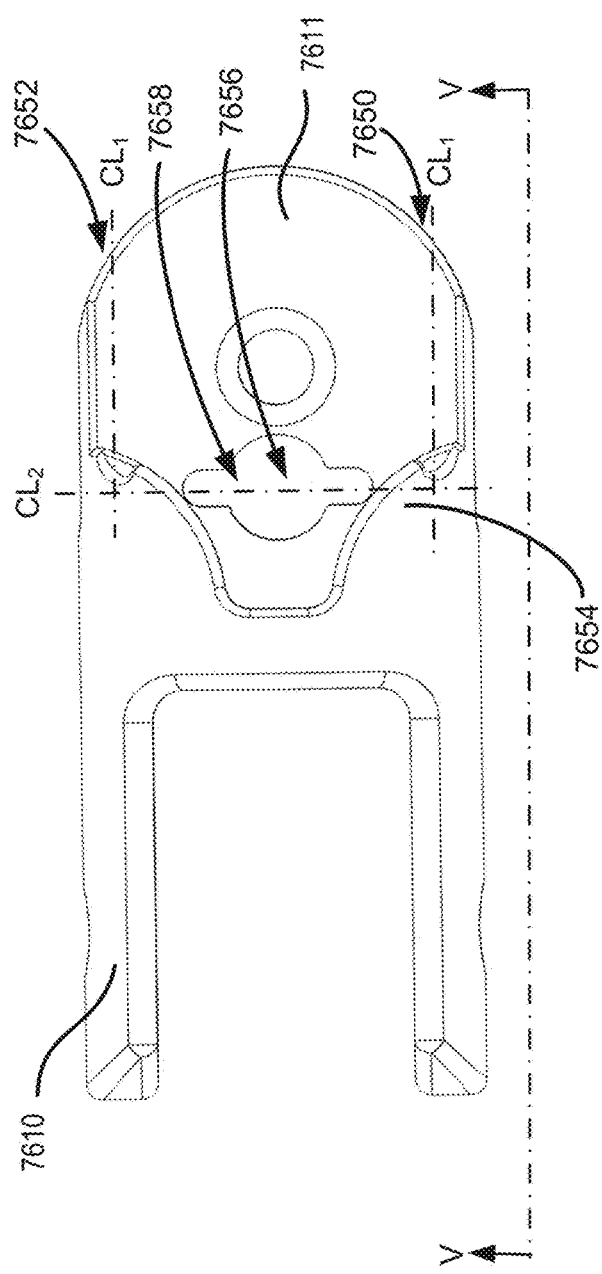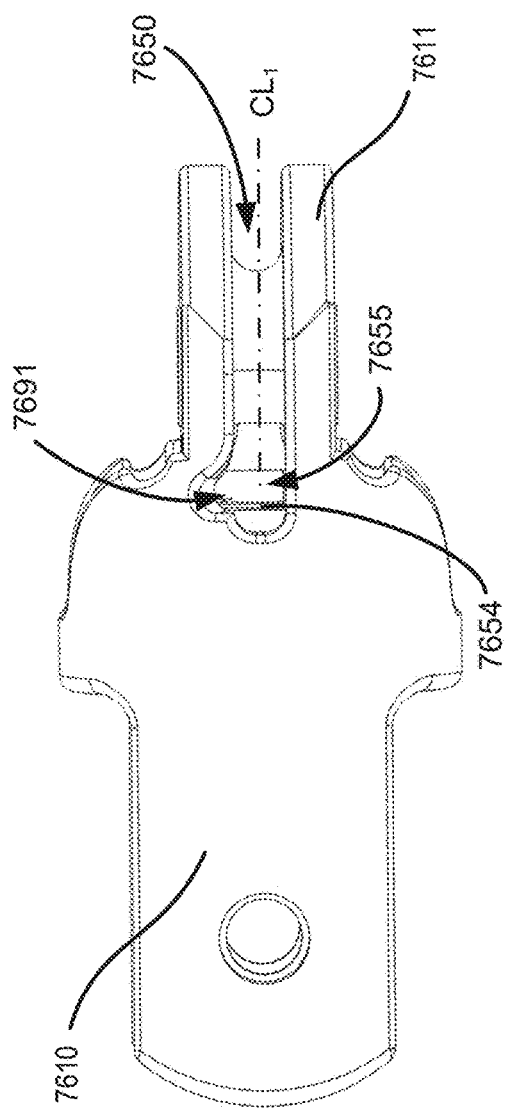

LOW-FRICTION, SMALL PROFILE MEDICAL TOOLS HAVING EASY-TO-ASSEMBLE COMPONENTS

RELATED APPLICATIONS

This patent application is a continuation of U.S. application Ser. No. 16/971,982 (filed Aug. 21, 2020) (entitled "LOW-FRICTION, SMALL PROFILE MEDICAL TOOLS HAVING EASY-TO-ASSEMBLE COMPONENTS"), which is a U.S. national stage filing under 35 U.S.C. § 371 of International Application No. PCT/US2019/020653 (filed Mar. 5, 2019) (entitled "LOW-FRICTION, SMALL PROFILE MEDICAL TOOLS HAVING EASY-TO-ASSEMBLE COMPONENTS"), which claims priority to and the filing date benefit of U.S. Provisional Patent Application No. 62/639,631 (filed Mar. 7, 2018) (entitled "LOW-FRICTION, SMALL PROFILE MEDICAL TOOLS HAVING EASY-TO-ASSEMBLE COMPONENTS"), each of which is incorporated by reference herein in its entirety.

BACKGROUND

The embodiments described herein relate to grasping tools, more specifically to medical devices, and still more specifically to endoscopic tools. More particularly, the embodiments described herein relate to low-friction tools and devices that include roller-assisted tension members that can be used, for example, in surgical applications.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of an extension (also referred to herein as the main tube or shaft). During an MIS procedure, the end effector, wrist mechanism, and the distal end of the main tube can be inserted into a small incision or a natural orifice of a patient to position the end effector at a work site within the patient's body. The optional wrist mechanism can be used to change the end effector's orientation with respect to the main tube to perform the desired procedure at the work site. Known wrist mechanisms generally provide the desired degrees of freedom (DOFs) for movement of the end effector. For example, for forceps or other grasping tools, known wrist mechanisms are often able to change the pitch and yaw of the end effector with reference to the main tube. A wrist may optionally provide a roll DOF for the end effector, or the roll DOF may be implemented by rolling the main tube. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the wrist mechanism and end effector, known instruments include tension members (e.g., cables, cable/hypotube combinations, tension bands) that extend through the main tube of the instrument and that connect the wrist mechanism to a transmission (also referred to herein as a backend mechanism). The backend mechanism moves the cables to operate the wrist mechanism. For teleoperated systems, the backend mechanism is motor driven and can be operably coupled to a processing system to provide a user interface for a doctor to control the instrument.

Patients benefit from continual efforts to improve the effectiveness of MIS methods and tools. For example, reducing the size and/or the operating footprint of the main tube and wrist mechanism can allow for smaller entry incisions, thereby reducing the negative effects of surgery, such as pain, scarring, and undesirable healing time. But, producing small diameter medical instruments that implement the clinically desired functions for minimally invasive procedures can be challenging. Specifically, simply reducing the size of known wrist mechanisms by "scaling down" the components will not result in an effective solution because required component and material properties do not scale. For example, efficient implementation of a wrist mechanism can be complicated because the cables must be carefully routed through the wrist mechanism to maintain cable tension throughout the range of motion of the wrist mechanism and to minimize the interactions (or coupling effects) of one rotation axis upon another. Further, pulleys and/or contoured surfaces are generally needed to reduce cable friction, which extends instrument life and permits operation without excessive forces being applied to the cables or other structures in the wrist mechanism. Increased localized forces that may result from smaller structures (including the cables and other components of the wrist mechanism) can result in undesirable lengthening (e.g., "stretch" or "creep") of the cables during storage and use, reduced cable life, and the like.

Further, some medical instruments have end effectors that require electrical energy for clinical functions such as desiccation, hemostasis, cutting, dissection, fulguration, incisions, tissue destruction, cauterizing, and vessel sealing. Accordingly, known instruments include one more conductors routed through the wrist mechanism to the portion of an end effector to be energized. Fitting all the components of the wrist mechanism, drive cables, and conductive wires into a small diameter, for example, less than about 10 mm, while preserving the necessary strength and function of these components can be difficult.

In addition to reducing the size of medical instruments, it is also desirable to develop low-cost instruments that are effectively disposable (i.e., that are intended for a single use only at an economic cost). With such instruments, each MIS procedure can be performed with a new, sterilized instrument, which eliminates cumbersome and expensive instrument reuse cleaning and sterilization procedures. Many current instrument designs are expensive to produce, however, and so for economy these instruments undergo sterile reprocessing for use during multiple surgical procedures. In part, the cost of these instruments may be due to multiple-strand tungsten cables and hypotube portions to withstand the operating loads.

In some instances, known wrist mechanisms make use of multiple pairs of cables to provide control for moving the wrist mechanism in various ranges of motion including yaw, pitch and roll movements of the wrist mechanism with reference to the main tube. These conventional wrist mechanisms use a pair of pitch cables that are coupled together to form a cable loop to provide pitch control for the wrist mechanism. The routing for each of the individual cables in such known wrist mechanisms can enhance pitch control, but may also restrict movement of the pitch cables during pitch movements and increase friction associated with actuating pitch movements. Further, the inclusion of cable guidance and connection features of these mechanisms may also increase the size of the wrist mechanism or make it difficult to reduce its size and footprint.

In addition, known wrist mechanisms can be difficult to assemble. For example, assembly procedures for some known wrist mechanisms can include performing cable crimping procedures to axially connect a pair of cables to each other to form a cable loop, and then coupling the cable pair to the wrist mechanism with the crimp being retained in a pocket formed in the wrist mechanism. Although crimping and connecting the cables to each other prior to installation may avoid damage pertaining to the crimping operation, installation of the cable loop, along with installation of the attached cable crimp, may complicate installation of the cable loop and increase undesirable bending of or damage to the cable loop during installation.

Thus, a need exists for improved endoscopic tools. Improvements may include wrist mechanisms having reduced size, reduced part count, lower cost of materials, and increased-strength tension members operating with low friction during use. In addition, improvements may permit easy assembly, including installation of tension members in wrist mechanisms to axially connect two or more individual tension members while avoiding adversely impacting the integrity of the tension members from bending, twisting, or other actions during installation.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, a low-friction medical device includes a first link, a second link, and a tension member. The first link is coupled to an instrument shaft and defines a first guide path therein. The second link has a proximal end portion and a distal end portion. The second link is rotatable relative to the first link through an angular range. The distal end portion of the second link is coupled to a tool member, and the tool member is rotatable relative to the second link about a second axis. A second guide path is defined within the second link between the tool member and the first guide path. The second link includes a curved guide surface that defines a portion of the second guide path. The tension member has a first tension member portion, a second tension member portion, and a third tension member portion between the first tension member portion and the second tension member portion. The first tension member portion is within the first guide path, and the second tension member portion is coupled to the tool member. The third tension member portion is in contact with the curved guide surface throughout a portion of the angular range. The first tension member portion is parallel to a centerline of the first guide path.

In some embodiments, a low-friction medical device includes a first link, a second link, and a tension member. The first link is coupled to an instrument shaft and defines a first guide path. The second link is coupled to the first link and is rotatable relative to the first link about a first axis. The second link defines a second guide path, a retention pocket, a connection path and an assembly path. The connection path extends through a portion of the second link between the second guide path and the retention pocket. A wall of the second link surrounds a portion of the connection path. A connection path centerline and a centerline of the second guide path define a first plane within the second link. The assembly path extends through the portion of the second link into the retention pocket. A centerline of the assembly path is nonparallel to the connection path centerline within a second plane that is nonparallel to the first plane. The tension member has a first tension member portion, a second tension member portion and a retention member coupled to the second tension member portion. The first tension member portion is configured to be: (A) inserted through the assembly path along the assembly path centerline, and (B) rotated until the first tension member portion is within the second guide path. The retention member is retained within the retention pocket after the first tension member portion is rotated such that movement of the tension member relative to the second link is limited. The second link is configured to rotate relative to the first link about the first axis when the first tension member portion is moved within the second guide path.

Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIG. 7 is a diagrammatic top view of the portion of the instrument shown in FIG. 5 in a second orientation.

FIG. 36 is a side view of the second link of the instrument of FIG. 32 in the first orientation.

FIG. 37 is a bottom view of the second link of the instrument of FIG. 32 in the first orientation, taken along line V-V shown in FIG. 36.

DETAILED DESCRIPTION

Figure 1:
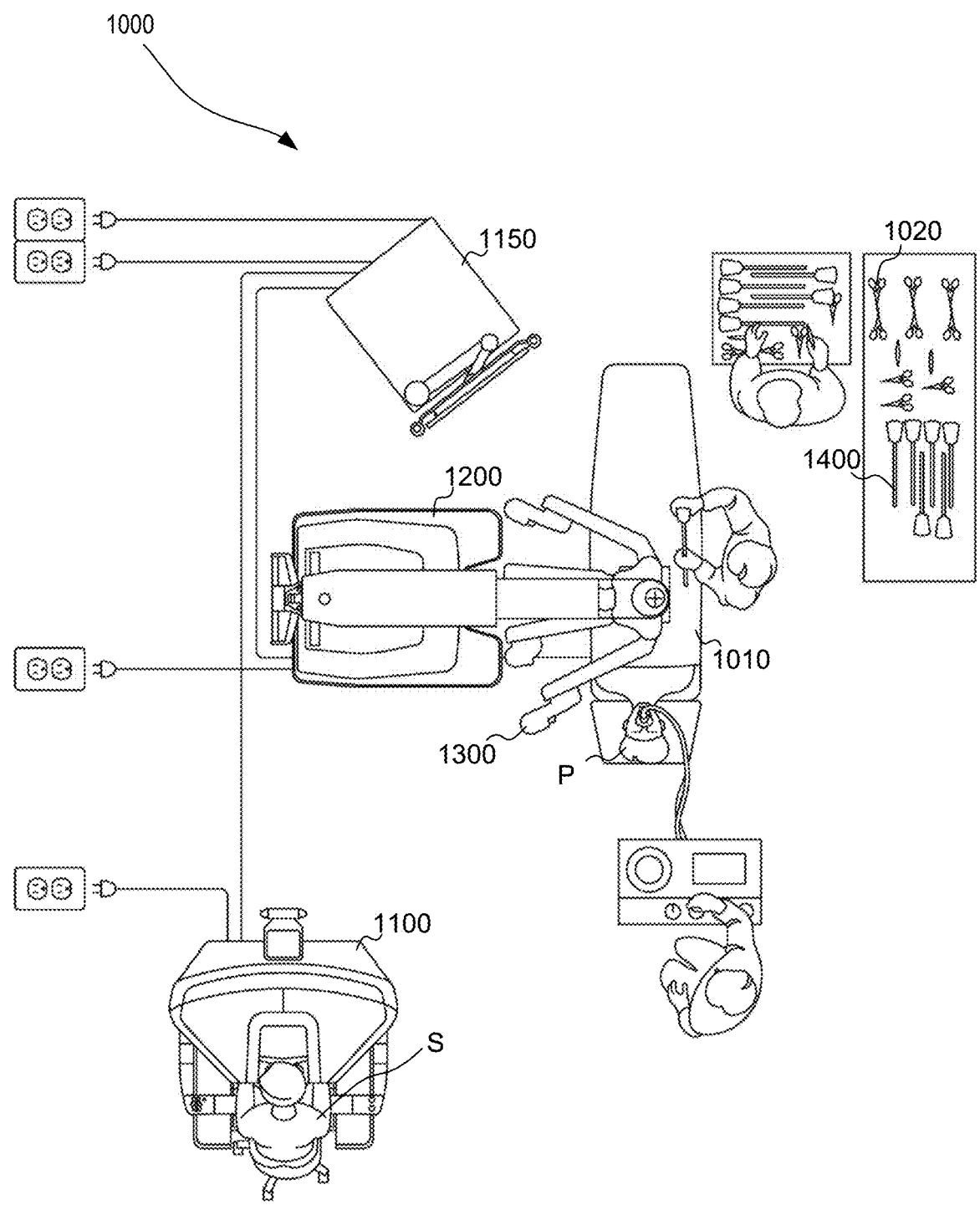
FIG. 1 is a plan view of a minimally invasive teleoperated medical system according to an embodiment, being used to perform a medical procedure such as surgery.

The embodiments described herein can advantageously be used in a wide variety of grasping, cutting, and manipulating operations associated with minimally invasive surgery. In particular, the instruments described herein can be low-cost, disposable instruments that facilitate being used for only one procedure. As described herein, the instruments include one or more cables (which act as tension members) that can be moved to actuate the end effector with multiple degrees of freedom. Moreover, the cables can include regions having a larger cross-sectional area to promote increased strength, or the cables can be wrapped or curved to allow efficient routing within a miniaturized wrist assembly.

In some embodiments, a low-friction medical device includes a first link, a second link, and a tension member. The first link is coupled to an instrument shaft and defines a first guide path therein. The second link has a proximal end portion and a distal end portion. The second link is rotatable relative to the first link about a first axis through an angular range. The distal end portion of the second link is coupled to a tool member and the tool member is rotatable relative to the second link about a second axis. A curved guide path is defined within the second link between the tool member and the first guide path. The second link includes a curved guide surface that defines a portion of the second guide path. The tension member has a first tension member portion, a second tension member portion, and a third tension member portion between the first tension member portion and the second tension member portion. The first tension member portion is within the first guide path, and the second tension member portion is coupled to the tool member. The third tension member portion is in contact with the curved guide surface throughout a portion of the angular range. The first tension member portion is parallel to a centerline of the first guide path.

In some embodiments, the centerline of the first guide path is offset from a centerline of the shaft by a first distance, and the curved guide surface is characterized by a radius about the first axis. In such embodiments, the radius is equal to the first distance. In some embodiments, the centerline of the first guide path is offset from a centerline of the shaft by a first distance, and the curved guide surface is characterized by a radius of curvature that defines a first portion of the second guide path. A center of the radius of curvature is offset from the shaft by a second distance, and the second distance is equal to the sum of the radius of curvature and the first distance.

In some embodiments, the tension member includes a fourth tension member portion between the first tension member portion and the third tension member portion. The fourth tension member portion is parallel to the centerline of first guide path throughout the angular range. In some embodiments, the curved guide surface of the second link is an outer surface of a pulley coupled to the second link, or the curved guide surface is a wall of the second link. In some embodiments, the curved guide surface is a first curved guide surface and the second link includes a second curved guide surface. The first curved guide surface includes an outer surface of a pulley coupled to the second link, and forms a first portion of the second guide path. The second curved guide surface defines a second portion of the second guide path. The portion of the angular range is a first portion, and the third tension member portion is in contact with the outer surface of the pulley throughout the first portion of the angular range. The third tension member portion is in contact with the second curved guide surface throughout a second portion of the angular range. The fourth tension member portion is parallel to the centerline of the first guide path throughout the first angular range and the second angular range. In some embodiments, the third tension member portion is spaced apart from the outer surface of the pulley and is in contact with the second curved guide surface when the second link is in a first orientation relative to the first link. The third tension member is spaced apart from the second curved guide surface and is contact with the outer surface of the pulley when the second link is in a second orientation relative to the first link.

In some embodiments, the centerline of the first guide path is offset from a centerline of the shaft by a distance, and the outer surface of the pulley defines a pulley radius equal to the distance. In some embodiments, the second curved guide surface is characterized by a radius of curvature, and the distance is less than the sum of the pulley radius and the radius of curvature. In some embodiments, the distance is a second distance, the center of the radius of curvature is offset from the centerline of the shaft by a first distance, and the first distance is equal to the sum of the second distance and the radius of curvature.

In some embodiments, a low-friction medical device includes a first link, a second link, and a tension member. A first guide path is defined within the first link, and a centerline of the first guide path is offset from a centerline of the shaft by a distance. The second link has a proximal end portion and a distal end portion. The proximal end portion of the second link is rotatably coupled to the first link and the second link is rotatable relative to the first link about a first axis through an angular range. The distal end portion of the second link is rotatably coupled to a tool member and the tool member is rotatable relative to the second link about a second axis. A second guide path is defined within the second link between the tool member and the first guide path. The second link includes a curved guide surface that defines a portion of the second guide path. The curved guide surface is characterized by a radius about the first axis. The radius is equal to the distance that the centerline of the first guide path is offset from the centerline of the shaft. The tension member has a first tension member portion, a second tension member portion, and a third tension member portion between the first tension member portion and the second tension member portion. The first tension member portion is within the first guide path, and the second tension member portion is coupled to the tool member. The third tension member portion is in contact with the curved guide surface throughout at least a portion of the angular range.

In some embodiments, a low-friction medical device includes a first link, a second link, and a tension member. A first guide path is defined within the first link. A centerline of the first guide path is offset from a centerline of the shaft by a first distance. The second link has a proximal end portion and a distal end portion. The proximal end portion of the second link is rotatably coupled to the first link. The second link is rotatable relative to the first link about a first axis through an angular range. The distal end portion of the second link is rotatably coupled to a tool member and the tool member is rotatable relative to the second link about a second axis. A second guide path is defined within the second link between the tool member and the first guide path. The second link includes a curved guide surface that defines a portion of the second guide path. The curved guide surface is characterized by a radius of curvature. A center of the radius of curvature is offset from the centerline of the shaft by a second distance. The second distance is equal to the sum of the radius of curvature and the first distance. The tension member has a first tension member portion, a second tension member portion, and a third tension member portion between the first tension member portion and the second tension member portion. The first tension member portion is within the first guide path, and the second tension member portion is coupled to the tool member. The third tension member portion is in contact with the curved guide surface throughout at least a portion of the angular range.

In some embodiments, the tool member has a pulley portion coupled to the distal end portion of the second link by a pin. The second portion of the tension member is wrapped about the pulley portion offset from the pin such that the tool member rotates relative to the second link about the second axis when the tension member is moved. The second portion of the tension member is parallel between the curved guide surface of the second link and the pulley portion of the tool member.

In some embodiments, a medical device includes a first link, a second link, and a tension member. The first link is coupled to an instrument shaft and defines a first guide path. The second link is rotatably coupled to the first link to rotate relative to the first link about a first axis. The second link defines a second guide path, a retention pocket, a connection path, and an assembly path. The connection path extends through a portion of the second link between the second guide path and the retention pocket. A wall of the second link surrounds a portion of the connection path. A connection path centerline and a centerline of the second guide path define a first plane within the second link. The assembly path extends through a portion of the second link into the retention pocket. A centerline of the assembly path is nonparallel to the connection path centerline within a second plane that is nonparallel to the first plane. The tension member has a first tension member portion, a second tension member portion, and a retention member coupled to the second tension member portion. The first tension member portion is configured to be: A) inserted through the assembly path along the assembly path centerline, and B) rotated until the first tension member portion is within the second guide path. The retention member is retained within the retention pocket after the first tension member portion is rotated such that movement of the tension member relative to the second link is limited. The second link is further configured to rotate relative to the first link about the first axis when the first tension member portion is moved within the second guide path.

In some embodiments, the tension member is a cable and the retention member is a cable crimp. In some embodiments, the cable crimp is configured to have an angular twist from a relaxed state with respect to a longitudinal axis of the tension member at the cable crimp during installation. In some embodiments, the first tension member portion is rotated through an installation angle of about ninety degrees. In some embodiments, an elongate slot is defined within the second link, and the cable crimp is configured to slide through the elongate slot and into the retention pocket when the tension member portion is rotated. In some embodiments, the cable crimp is configured to return to the relaxed state of no angular twist after installation. In some embodiments, a size of the retention pocket is greater than a size of the connection path. In some embodiments, the second plane is transverse to the first plane. In some embodiments, the assembly path centerline and the connection path centerline form an insertion angle of between 5 degrees and 45 degrees. In some embodiments, the retention member includes a swage connector attached to the tension member.

In some embodiments, a medical device includes a first link, a second link, and a tension member. The first link is coupled to an instrument shaft and defines therein a first guide path. The second link is rotatably coupled a first link to rotate relative to the first link about a first axis. The second link defines a second guide path, a retention pocket, a connection path, and an assembly path. The connection path extends through a portion of the second link between the second guide path and the retention pocket. A first wall of the second link defining an elongate slot opening into the retention pocket. A second wall of the second link defines a distal boundary of the retention pocket. A connection path centerline and a centerline of the second guide path define a first plane within the second link. The assembly path extends through the portion of the second link into the retention pocket. An assembly path centerline of the assembly path is nonparallel to the connection path centerline within a second plane that is nonparallel to the first plane. The tension member has a first tension member portion, a second tension member portion, and a retention member coupled to the second tension member portion. The first tension member portion is configured to be A) inserted through the elongate slot and the assembly path along the assembly path center-line, and B) rotated until the first tension member portion is within the second guide path. The retention member is retained within the retention pocket after the first tension member portion is rotated such that movement of the tension member relative to the second link is limited. The second link is configured to rotate relative to the first link about the first axis when the first tension member portion is moved within the second guide path.

In some embodiments, a method of assembling a portion of a wrist assembly is provided, in which the wrist assembly includes a first link and a second link. The first link defines a first guide path, and the second link is rotatably coupled to the first link to rotate relative to the first link about a first axis. The method includes inserting a first end portion of a tension member through an assembly path defined within the second link. The assembly path extends through a portion of the second link into a retention pocket defined by the second link. The tension member includes a second end portion and a retention member coupled to the second end portion. The method further includes rotating, after the inserting, a portion of the tension member about a rotation axis that is nonparallel to a longitudinal axis of the first end portion of the tension member. The rotating causing the first end portion of the tension member to be within a second guide path and a connection path defined by the second link. The connection path extends through a portion of the second link between the second guide path and the retention pocket. An assembly path centerline of the assembly path is nonparallel to a connection path centerline of the connection path.

In some embodiments, the method of assembling a portion of a wrist assembly further includes inserting the first end portion of the tension member into the first guide path. In some embodiments, the rotating includes rotating the tension member through an angle of between 5 degrees and 45 degrees.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California Examples of such surgical systems are the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations.

Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled instrument 1400 (also referred to as a "tool" or "tool assembly") through a minimally invasive incision in the body or natural orifice of the patient P while the surgeon S views the surgical site and controls movement of the instrument 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of instruments 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
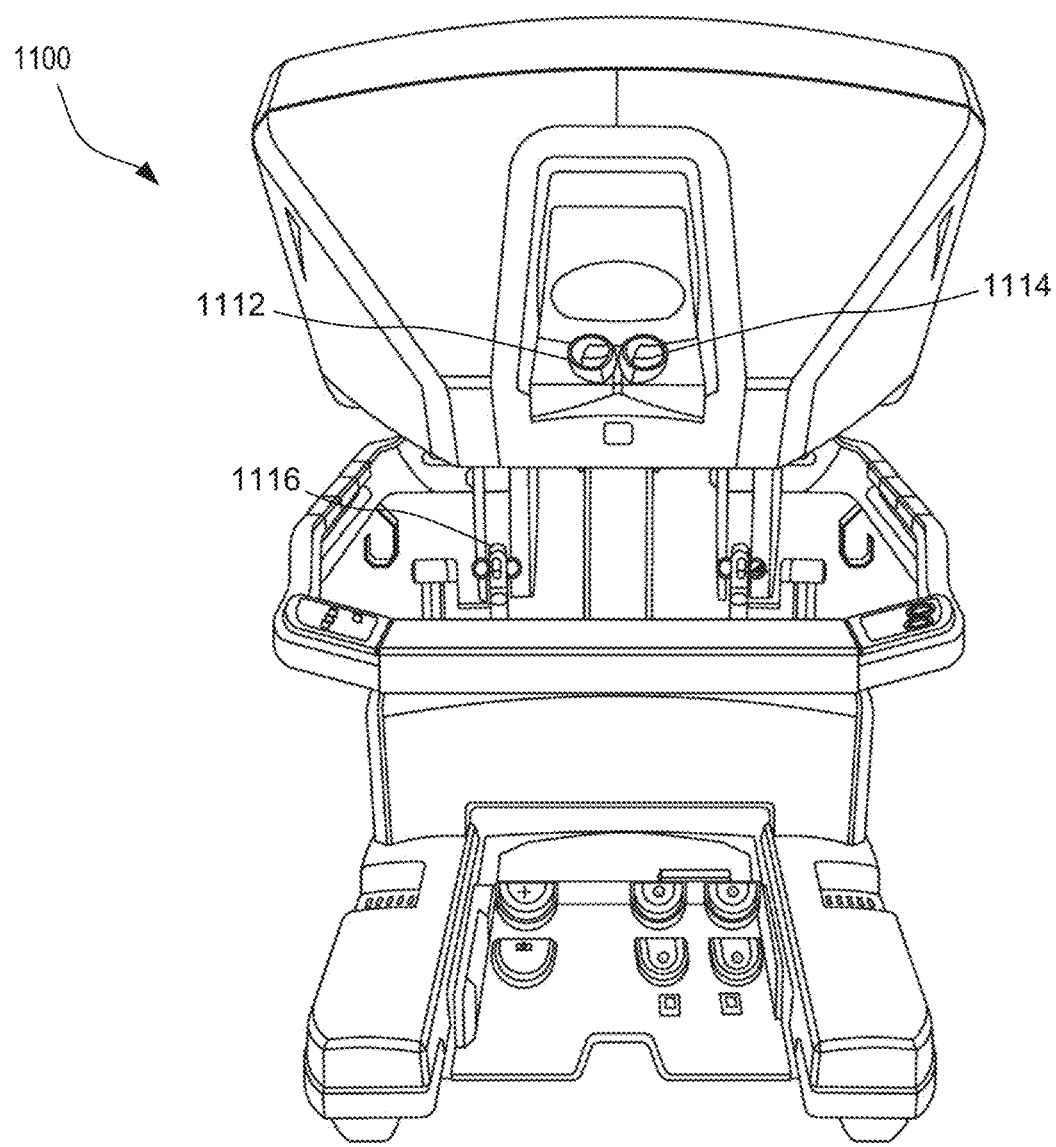
FIG. 2 is a perspective view of an optional auxiliary unit of the minimally invasive teleoperated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
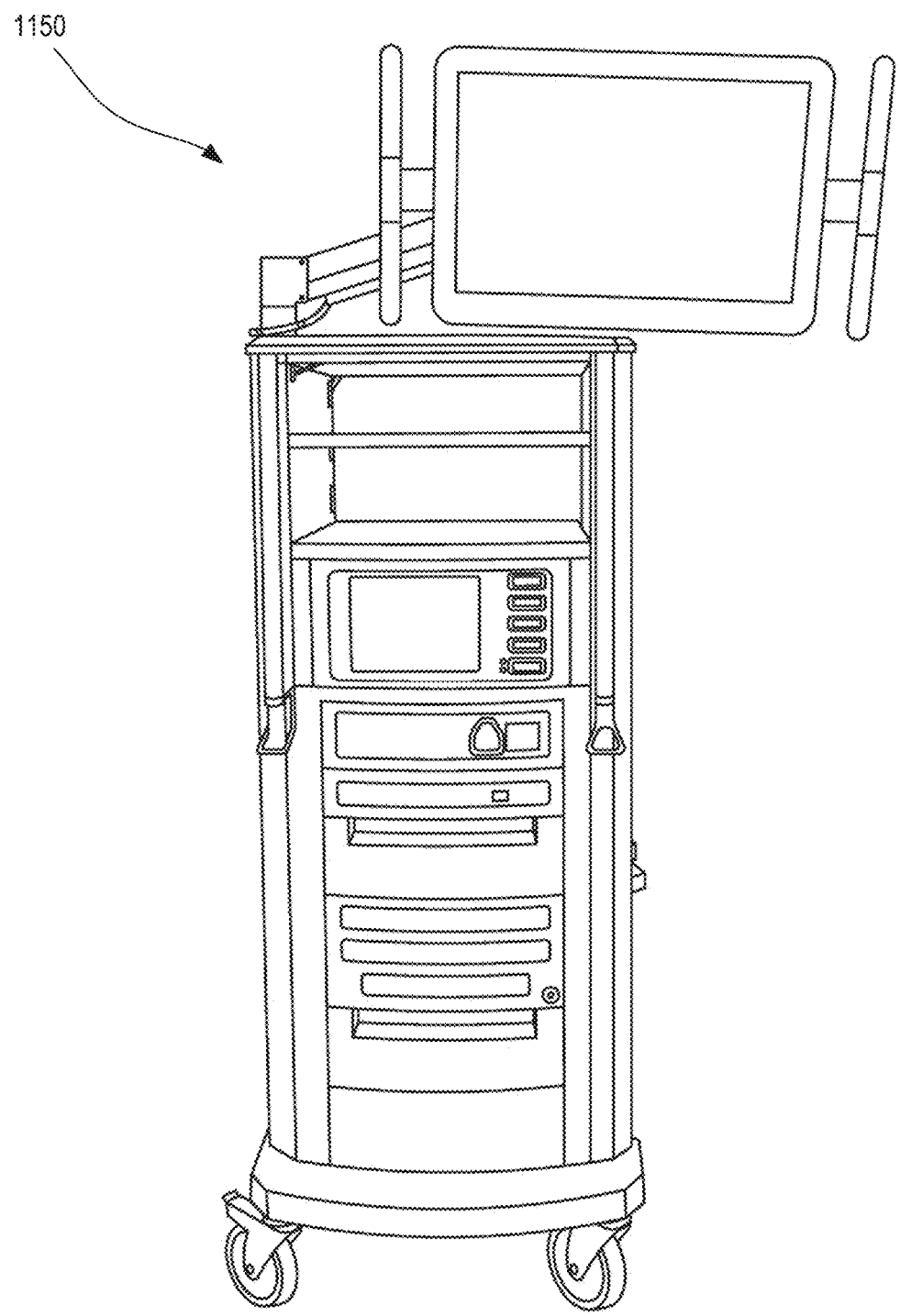
FIG. 3 is a perspective view of a user control console of the minimally invasive teleoperated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
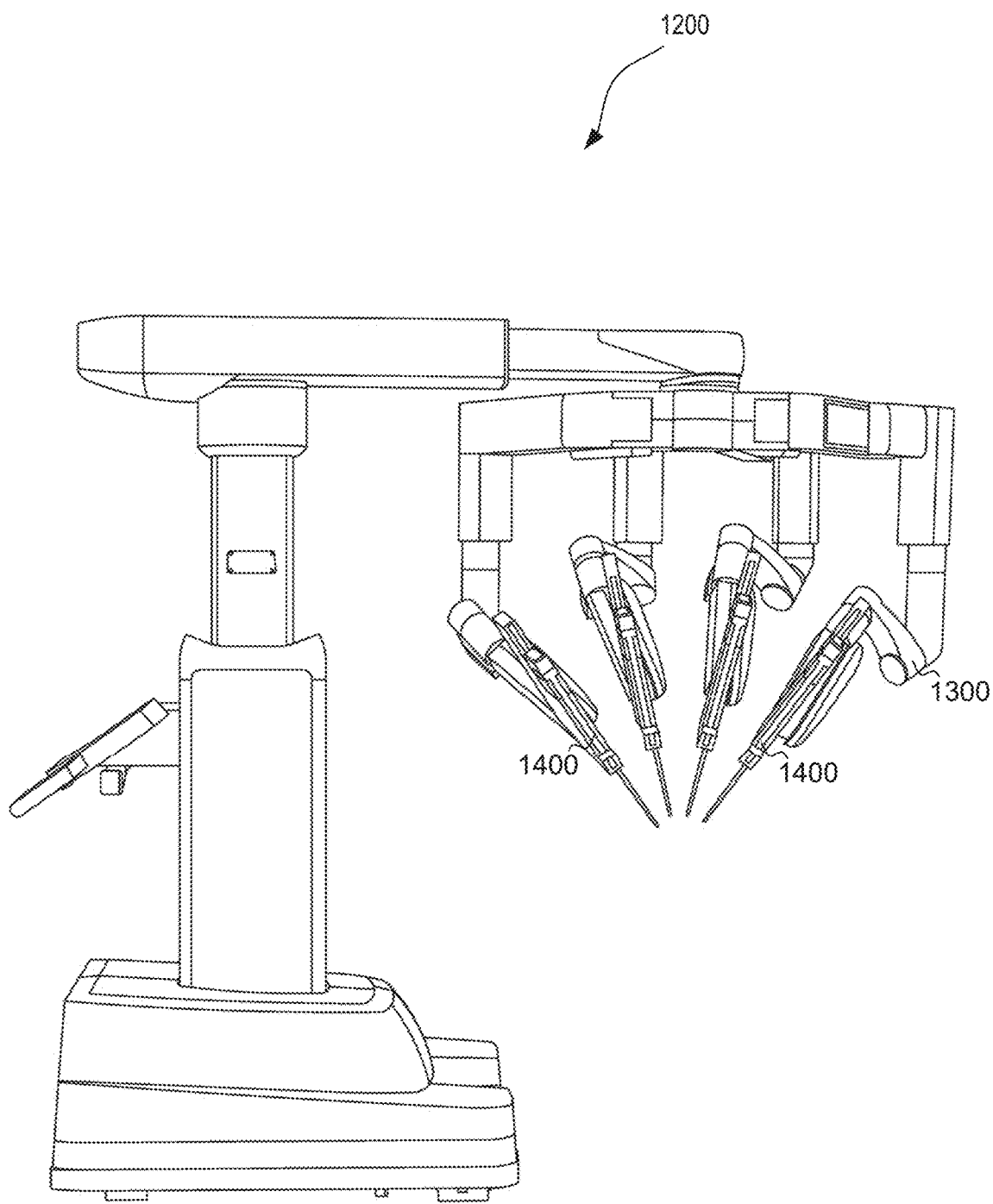
FIG. 4 is a front view of a manipulator unit, including a plurality of instruments, of the minimally invasive teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a kinematic remote center of motion is maintained at the incision or orifice. In this manner, the incision size can be minimized.

Figure 5:
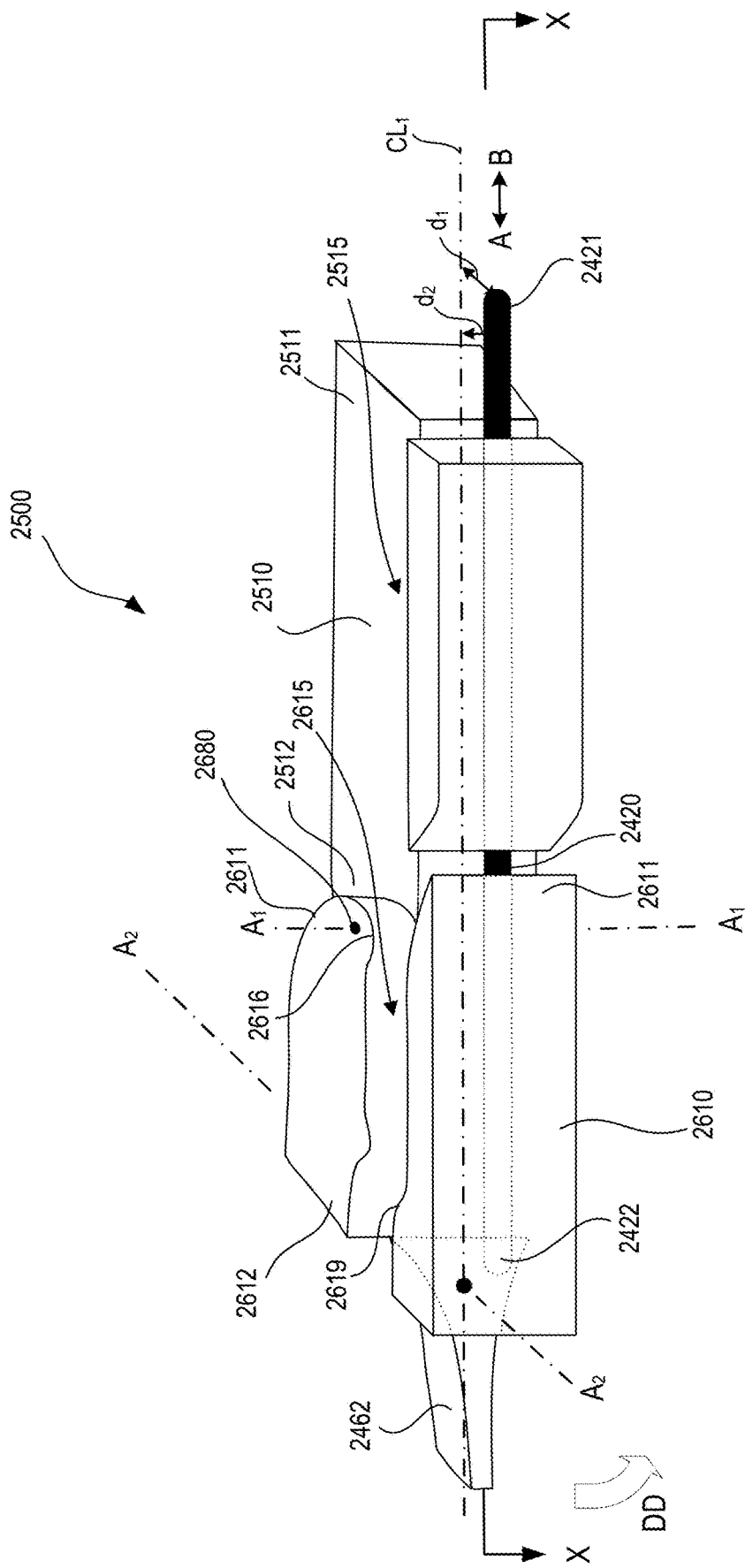
FIG. 5 is a diagrammatic perspective view of a portion of an instrument of a surgery system in a first position, according to an embodiment.
Figure 6A:
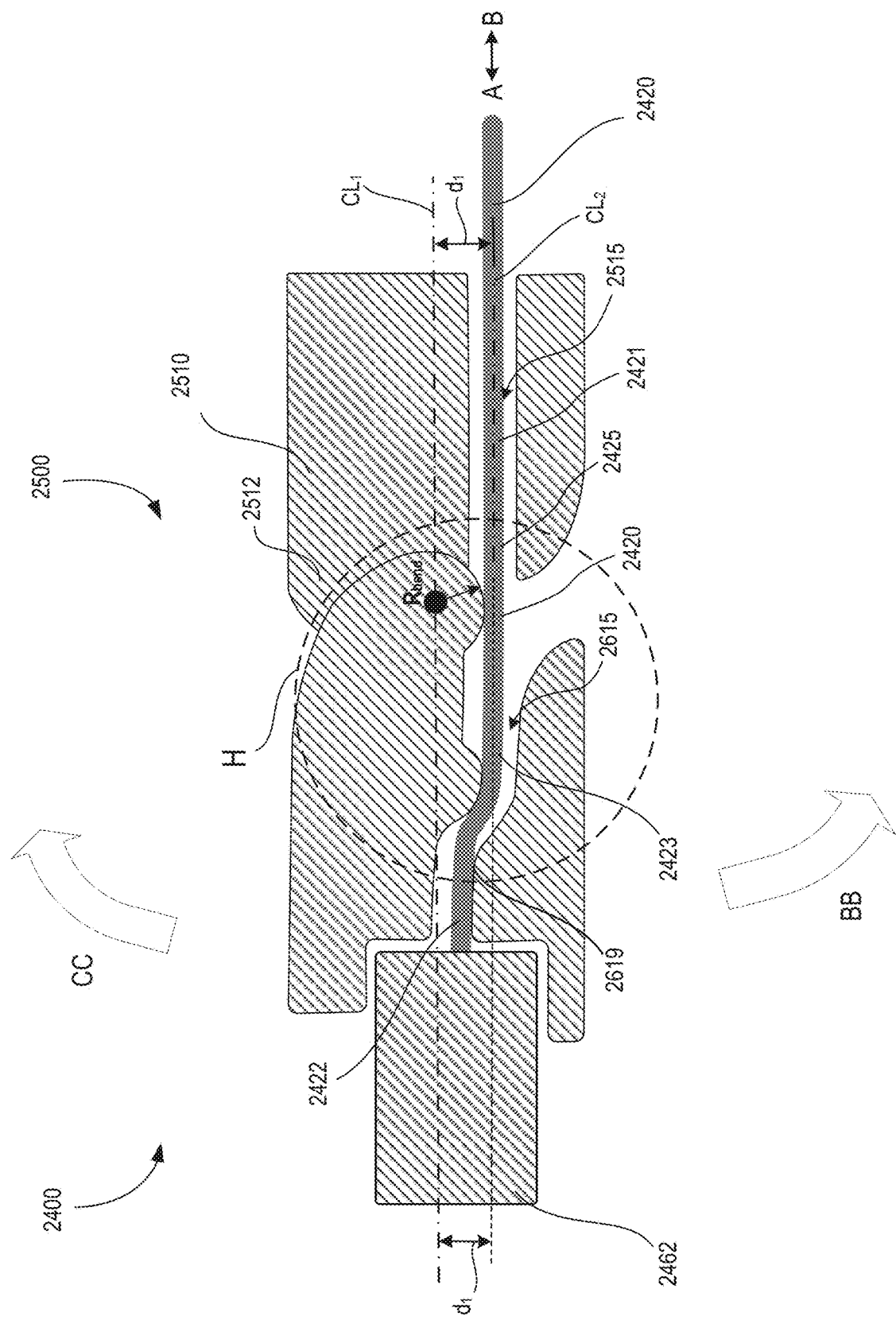
FIG. 6A is a diagrammatic top view of the portion of the instrument shown in FIG. 5 in the first orientation.
Figure 6B:
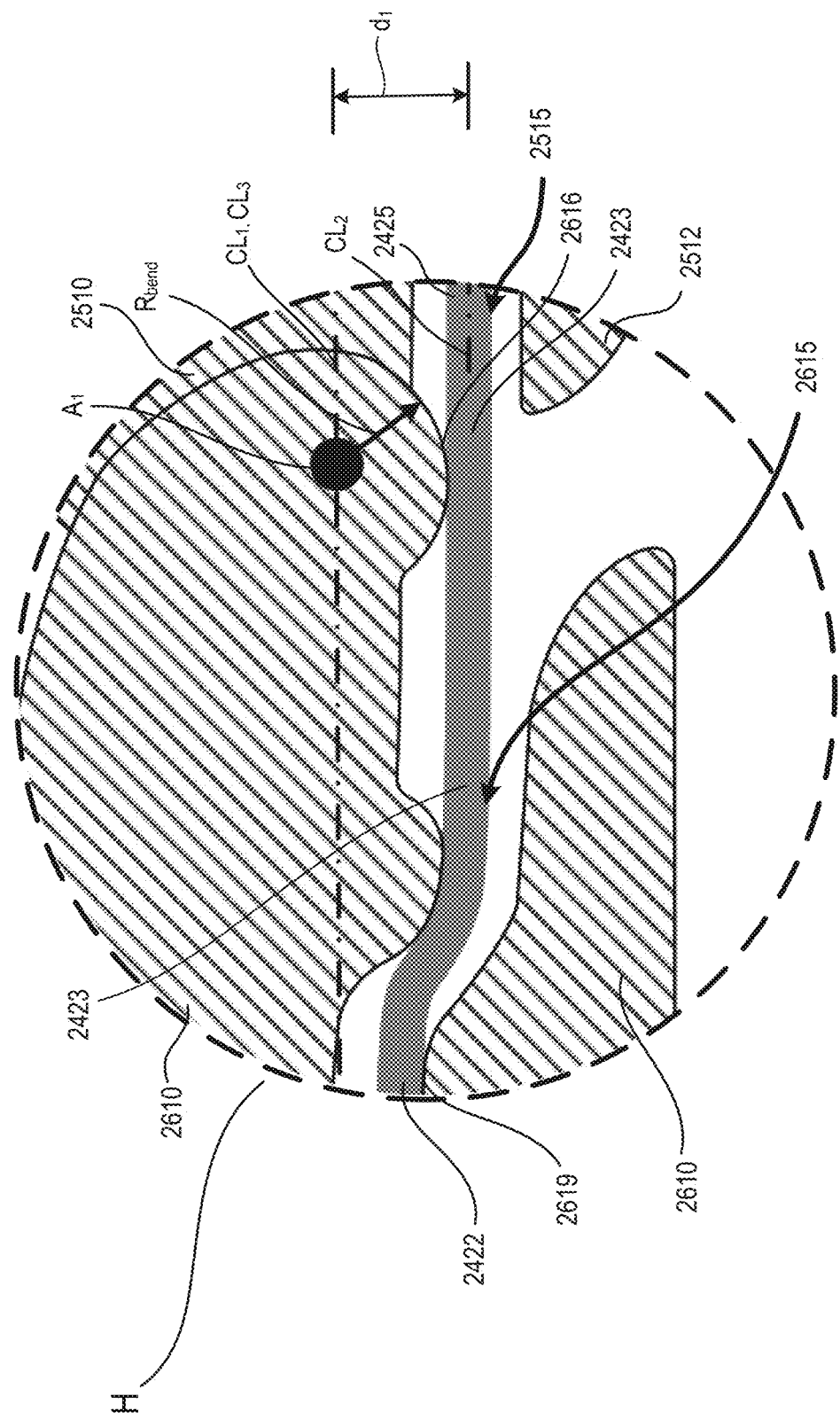
FIG. 6B is an enlarged view of a portion of the instrument shown in FIG. 5 by the region H shown in FIG. 6A.

FIGS. 5, 6A, 6B, and 7 are diagrammatic illustrations of various portions of an instrument 2400, according to an embodiment. In some embodiments, the instrument 2400 or any of the components therein are optionally parts of a surgical system that performs minimally invasive surgical procedures and which can include a manipulator unit, a series of kinematic linkages, a series of cannulas, or the like. The instrument 2400 (and any of the instruments described herein) can be used in any suitable surgical system, such as the MIRS system 1000 shown and described above. The instrument 2400 includes a wrist assembly 2500, at least one tension member 2420, and a tool member 2462. Although only one tension member 2420 is shown, one or more additional tension members or one or more additional tool members can be included. As described herein, the instrument 2400 is configured such that movement of the tension member 2420 produces movement of the wrist assembly 2500 (as shown in FIGS. 6A and 7), movement of the tool member 2462 (as illustrated in FIG. 5), or both movement of the wrist assembly 2500 and movement of the tool member 2462.

Figure 9:
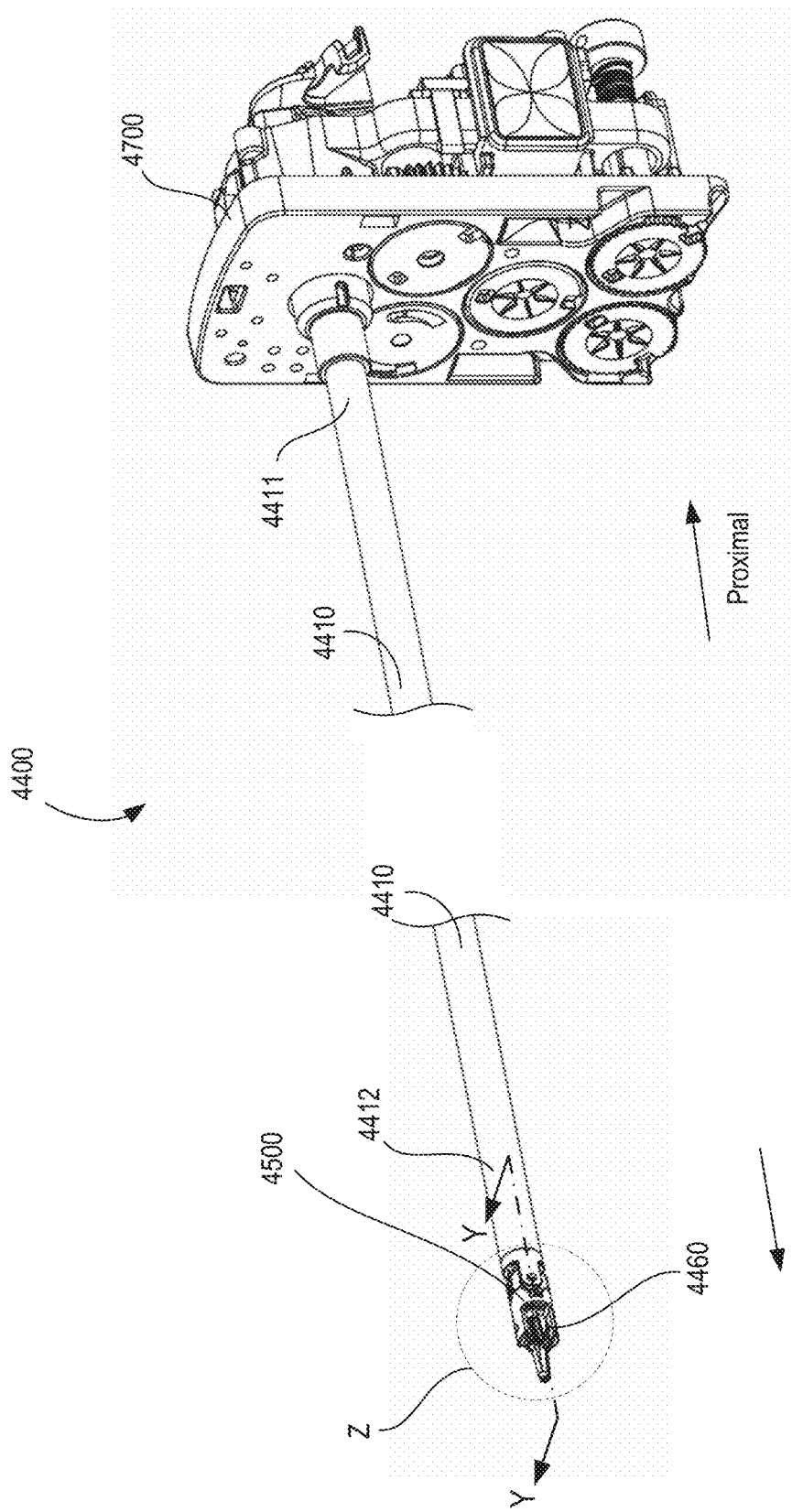
FIG. 9 is a perspective view of an instrument of a surgery system in a first orientation, according to an embodiment.

The wrist assembly 2500 includes a proximal first link 2510 and a distal second link 2610. The first link 2510 has a proximal end portion 2511 and a distal end portion 2512. The proximal end portion 2511 is coupled to an instrument shaft (not shown). Although the instrument shaft is not shown in FIGS. 5-7, the proximal end portion 2511 can be coupled to any suitable instrument shaft, such as the instrument shaft 4410 (FIG. 9) shown and described herein. Moreover, the proximal end portion 2511 of the first link 2510 can be coupled to the instrument shaft via any suitable mechanism, such as welding, interference fit, adhesive, etc. As described below, the distal end portion 2512 is rotatably coupled to the second link 2610. In this manner, the first link 2510 and the second link 2610 form the wrist assembly 2500 having a first axis of rotation $A_1$ (which functions as a pitch axis; the term pitch is arbitrary) about which the second link can rotate relative to the first link through an angular range of the wrist assembly. The proximal first link 2510 defines a first guide path 2515 within and through the first link, which extends from its proximal end portion 2511 to its distal end portion 2512. At least a portion of the first guide path 2515 is parallel with the centerline $CL_1$ of the shaft (not shown) but is offset from the centerline of the shaft as discussed further below. As such, a centerline $CL_2$ of the first guide path 2515 is offset from the centerline $CL_1$ of the shaft by a first distance $d_1$. In some embodiments, the centerline $CL_1$ of the shaft is coaxial with a centerline of the first link 2510 and intersects the first axis of rotation $A_1$. Thus, in such embodiments the centerline $CL_2$ of the first guide path 2515 is offset from the first axis of rotation $A_1$ of the shaft by a first distance $d_1$.

The second link 2610 has a proximal end portion 2611 and a distal end portion 2612. As described above, the proximal end portion 2611 is rotatably coupled to the distal end portion 2512 of the first link 2510 to form a wrist joint. The axis of rotation $A_1$ is located on the centerline $CL_1$ of the shaft (and in some embodiments, the first link 2510) and along a centerline $CL_3$ of the second link 2610 (see FIG. 7). In a first orientation shown in FIGS. 5, 6A and 6B, the shaft centerline $CL_1$ (also centerline of the first link 2510) and the centerline $CL_3$ of the second link are collinear. In a second orientation shown in FIG. 7, the shaft centerline $CL_1$ of the first link 2510 and the centerline $CL_3$ of the second link form an angle (i.e., a pitch angle). In some embodiments, the proximal end portion 2611 can be coupled to the distal end portion 2512 via a pinned joint, such as the pinned joint between the proximal clevis 220 and the distal clevis 230 shown and described in U.S. Pat. No. 8,821,480 B2 (filed Jul. 16, 2008), entitled "Four-Cable Wrist with Solid Surface Cable Channels," which is incorporated herein by reference in its entirety. In other embodiments the proximal end portion 2611 can be coupled to the distal end portion 2512 via mating disc surfaces, such as the types shown and described in U.S. Patent Application Pub. No. US 2017/0120457 A1 (filed Feb. 20, 2015), entitled "Mechanical Wrist Joints with Enhanced Range of Motion, and Related Devices and Methods," which is incorporated herein by reference in its entirety.

The distal end portion 2612 of the second link 2610 includes a connector 2680 that is coupled to the tool member 2462 such that the tool member 2462 can rotate relative to the wrist assembly 2500 about a second axis of rotation $A_2$ through an angular range. As shown in FIG. 5, the second axis of rotation $A_2$ (also referred to as the yaw axis or the grip axis) is non-parallel to the first axis of rotation $A_1$. As described herein, axis $A_2$ functions both as a yaw axis (the term yaw is arbitrary) as the tool member 2462 rotates together with another tool member (not shown, but a second tool member can optionally be included in the instrument 2400) and as a grip axis as the tool member rotates in opposition to another tool member (not shown). Thus, the instrument 2400 provides for up to three degrees of freedom (i.e., a pitch rotation about the first axis of rotation $A_1$, a yaw rotation about the second axis of rotation $A_2$, and a grip motion about the second axis of rotation $A_2$). Although the second axis of rotation $A_2$ is shown as being normal to the first axis of rotation $A_1$, in other embodiments the second axis of rotation $A_2$ can be offset from the first axis of rotation $A_1$ by any suitable angle. The connector can be any suitable connector to rotatably couple the tool member 2462 to the second link 2610 to form a tool joint. For example, in some embodiments, the connector 2680 can include a clevis and a pin, such as the pinned joints shown and described in U.S. Pat. No. 9,204,923 (filed Jul. 16, 2008), entitled "Medical Instrument Electronically Energized Using Drive Cables," which is incorporated herein by reference in its entirety. In other embodiments the connector 2680 can include a compliant mechanism, such as the compliant mechanisms shown and described in International Publication No. WO 2016/123139 A2 (filed Jan. 26, 2016), entitled "Rolling-Contact Joint Mechanisms and Methods," which is incorporated herein by reference in its entirety.

The second link 2610 defines a second guide path 2615 within and through the second link, which extends from the first guide path 2515 at its proximal end portion 2611 to the tool member 2462 at its distal end portion 2612. The second link includes an inner guide surface 2616 that defines a portion of the second guide path, and is located on an inner portion of the second guide path 2615 with respect to the second link 2610. Although the inner guide surface 2616 is shown as being located along the second guide path 2615 at the proximal end portion 2611 of the second link 2610, in other embodiments the inner guide surface 2616 can be at any suitable location of or define any suitable portion of the second guide path 2615. The inner guide surface 2616 is curved with respect to the first axis of rotation $A_1$ such that the inner guide surface has a radius of curvature $R_{bend}$ from the first axis of rotation $A_1$ that extends throughout the angular range of rotation of the wrist assembly 2500 about the first axis of rotation $A_1$ in the direction CC shown in FIGS. 6A and 7. Although the radius of curvature $R_{bend}$ is shown as being centered at the first axis of rotation $A_1$, in other embodiments the radius of curvature of the inner guide surface 2616 can be centered at any suitable location. As discussed further below, the inner guide surface 2616 and the radius of curvature $R_{bend}$ are configured to maintain a portion of the tension member 2420 located within the first guide path 2515 to be centered therein to reduce frictional contact of the tension member 2420 during movement of the second link 2610 with respect to the first link 2510, movement of the tool member 2462 with respect to the second link 2610, or both movement of the tool member 2462 and the second link 2610.

The second link further includes an outer guide surface 2619 that defines a portion of the second guide path 2615 and is located on an outer portion of the second guide path 2615 with respect to the second link 2610. Although the outer guide surface 2619 is shown as being located within the second guide path 2615 near the distal end portion 2612, in other embodiments the outer guide surface 2619 can be at any suitable location of, or define any suitable portion of, the second guide path 2615. As discussed further below, the outer guide surface 2619 biases the tension member 2420 into contact with the inner guide surface 2616. In addition, the distal outer guide surface is configured to align the tension member 2420 with the tool member 2462 for attachment thereto.

The tension member 2420 has a proximal end portion 2421, a distal end portion 2422 coupled to the tool member 2462, a distal central portion 2423, and a proximal central portion 2425. The proximal end portion 2421 is located within a portion of the first guide path 2515 of the first link 2510. The distal central portion 2423 is between the distal end portion and proximal central portion 2425 and is located within the second guide path 2615 of the second link 2610. The proximal central portion 2425 is between the distal central portion 2423 and the proximal end portion 2421. At least the inner guide surface 2616 of the second link 2610 contacts the distal central portion 2423 of the tension member 2420 when the second link 2610 is in the first orientation shown in FIGS. 5, 6A, and 6B. Similarly stated, the distal central portion 2423 of the tension member 2420 is in contact with the inner guide surface 2616 throughout a portion of the angular range of motion of the second link 2610 relative to the first link 2510. The inner guide surface 2616 guides the path of the tension member 2420 to transition within the second curved guide path 2615 while in the first orientation shown in FIG. 6A and also when the second link 2610 rotates relative to the first link 2510 in direction CC as shown. Specifically, the inner guide surface 2616 is sized and positioned such that the proximal end portion 2421, the proximal central portion 2425, or both the proximal end portion 2421 and the proximal central portion 2425 of the tension member are alignment with the centerline $CL_2$ of the first guide path 2515. Similarly stated, this arrangement causes the proximal end portion 2421, the proximal central portion 2425, or both the proximal end portion 2421 and the proximal central portion 2425 of the tension member to be parallel to the centerline $CL_2$. Moreover, the radius of curvature $R_{bend}$ of the inner guide surface 2616 is positioned and sized such that the proximal end portion 2421, the proximal central portion 2425, or both the proximal end portion 2421 and the proximal central portion 2425 of the tension member remain parallel to the centerline $CL_2$ for the range of motion of the second link 2610 with respect to the first link 2510 in the direction CC. As such, the tension member 2420 can move within the first guide path 2515 in the directions shown by arrow AB without contacting surfaces within the first guide path. In this manner, frictional contact is reduced for movements of the tension member 2420 for the angular range of motion in direction CC.

In some embodiments, the inner guide surface 2616 has a radius of curvature $R_{bend}$ about the first axis of rotation $A_1$ that is less than or equal to the distance $d_1$ such that the proximal end portion 2421, the proximal central portion 2425, or both the proximal end portion 2421 and the proximal central portion 2425 of the tension member remain parallel to the centerline $CL_2$ over the range of motion of the second link 2610. Although shown as being a single radius of curvature $R_{bend}$, in other embodiments the inner guide surface 2616 can be a curved surface that is characterized by multiple different radii of curvature.

As described below along with other embodiments herein, in some embodiments a second tension member (not shown) can be similarly offset in an opposite direction from the longitudinal centerline $CL_1$ of the first link 2510 and the first axis $A_1$ to impart rotation in direction CC.

The proximal end portion 2421 of the tension member 2420 extends proximally out of the wrist assembly 2500, through the instrument shaft (not shown), and is coupled to an actuator (not shown) at the proximal end of the instrument. The actuator (which functions as a transmission) can move the proximal end portion 2421 of the cable by any suitable mechanism to produce a resulting movement (or force) at the distal end portion 2422 of the cable (as shown by arrow AB in FIGS. 5 and 6A). In some embodiments the actuator of the instrument 2400 is motor driven and is thus suitable for a robotic or teleoperated surgical system. The proximal central portion 2425 and the distal central portion 2423 of the tension member 2420 are disposed within the second guide path 2615, and the distal end portion 2422 of the cable is coupled to the tool member 2462. In this manner, as described herein, movement of the tension member 2420 can produce rotation of the tool member 2462, rotation of the second link 2610, or rotation of both the tool member 2462 and the second link 2610. The distal end portion 2422 of the tension member 2420 (e.g., a cable) can be coupled to the tool member 2462 by any suitable mechanism. For example, in some embodiments, the distal end portion 2422 can be coupled to the tool member 2462 by a pin or protrusion that engages (or is received within) a connection portion of the tool member 2462. In other embodiments the distal end portion 2422 can be coupled to the tool member 2462 via an adhesive. In yet other embodiments the distal end portion 2422 of the tension member can be wrapped about a pulley portion of the tool member 2462.

Referring to FIG. 5, the tool member 2462 is coupled to the wrist assembly 2500 and rotates relative to the wrist assembly around the second axis of rotation $A_2$. Specifically, the first and second guide paths 2510, 2615 are offset from the second axis of rotation $A_2$ by a distance $d_2$. In this manner, application of a tension force on the tension member 2420 in the proximal direction (indicated as direction B by the arrow AB) produces a torque on the tool member 2462 about the second axis of rotation $A_2$, which results in rotation of the tool member 2462 relative to the second link 2610, as shown by the arrow DD in FIG. 5. In this manner, a distal portion (e.g., an engagement portion) of the tool member 2462 can engage or manipulate a target tissue during a surgical procedure. The tool member 2462 (or any of the tool members described herein) can be any suitable medical tool member. For example, in some embodiments the tool member 2462 (or any of the tool members described herein) can include an engagement surface that functions as a gripper, cutter, tissue manipulator, or the like. In other embodiments the tool member 2462 (or any of the tool members described herein) can be an energized tool member that is used for cauterization procedures. Although only one tool member 2462 is shown, in other embodiments the instrument 2400 includes two moving tool members that cooperatively perform gripping or shearing functions. In this manner, the tool member 2462 can form a portion of an end effector for the surgical instrument 2400.

As shown in FIG. 7, the second link 2610 defines a longitudinal centerline $CL_3$ that intersects the first axis of rotation $A_1$. When the wrist assembly 2500 is in the first orientation (FIGS. 5, 6A and 6B), the longitudinal centerline $CL_1$ of the first link 2510 and the longitudinal centerline $CL_3$ of the second link 2610 are collinear (and are collectively identified as $CL_1$ in FIG. 5). When the second link 2610 rotates relative to the first link 2510 (i.e., rotates in pitch), the longitudinal centerline $CL_1$ of the first link 2510 and the longitudinal centerline $CL_3$ of the second link form a pitch angle. Throughout the angular range of motion in direction CC, including at the high pitch angle shown in FIG. 7, the tension member 2420 is maintained in alignment with the centerline $CL_2$ of the first guide path 2515 without frictional contact with surfaces of the first link 2510 within the first guide path.

Referring again to FIG. 7, the reduced amount of frictional contact between the tension member 2420 and components of the wrist assembly 2500 when the instrument is in a high pitch orientation allows the tension member 2420 to be moved in the direction AA to move the tool member 2462 when in a high pitch orientation in an efficient manner and with a reduced likelihood that the tension member 2420 will become bound. This allows movement of the tool member 2462 throughout the range of pitch orientations (e.g., at pitch angles of between zero degrees (FIG. 6A) and 90 degrees (FIG. 7), at pitch angles of between zero degrees and 45 degrees, at pitch angles of between zero degrees and 60 degrees).

In some embodiments, the tension member 2420 (and any of the tension members described herein) can be formed as a cable made of Tungsten or stainless steel to provide sufficient strength, bendability and durability. In some embodiments, cables can be constructed from multiple braids of fine wire, to provide strength and resiliency. In some embodiments, cables can be made from 150 to 350 braids of 0.018 mm to 0.025 mm (0.0007-inch to 0.001-inch) diameter tungsten wire providing cables with outer diameters of 0.356 mm to 0457 mm (0.014 inches to 0.018 inches).

In some embodiments, the instrument 2400 can include any suitable tension member. For example, in some embodiments, the instrument 2400 (and any of the instruments described herein) can include a tension member having any suitable cross-sectional shape. For example, in some embodiments the instrument 2400 (and any of the instruments described herein) can include a tension band, of the types shown and described in U.S. Patent Application No. 62/598,620 (filed Dec. 14, 2017), entitled "Medical Tools Having Tension Bands," which is incorporated herein by reference in its entirety. In some embodiments, such bands (and any of the tension members described herein) can have a trapezoidal shape. In other embodiments such bands (and any of the tension members described herein) can include slightly curved surfaces. Moreover, such bands (and any of the tension members described herein) can be constructed from any suitable materials. For example, in some embodiments, such bands (and any of the tension members described herein) can be constructed from a series of laminates that are bonded together (e.g., via an adhesive). The laminates can be constructed from any suitable material, including tungsten, steel, or any suitable polymer.

Although the first link 2510 and the second link 2610 are shown as having a rectangular cross-sectional shape, in other embodiments either the first link 2510, the second link 2610, or both the first link 2510 and the second link 2610 can have any suitable cross-sectional shape. For example, in some embodiment, either the first link 2510, the second link 2610, or both the first link 2510 and the second link 2610 can have substantially circular cross-sectional shape (i.e., the wrist assembly 2500 can be substantially cylindrical).

Although the second link 2610 is shown and described as having an inner guide surface 2616 (i.e., a surface located on an inner portion of the second guide path 2615), in other embodiments the second link 2610 can have a curved surface in any suitable location within (or that defines any portion of) the second guide path 2615. For example, in some embodiments, the second link 2610 can include a curved surface located on an outer portion of the second guide path (i.e., an outer guide surface) that contacts a portion of the tension member 2420 such that the proximal end portion 2421, the proximal central portion 2425, or both the proximal end portion 2421 and the proximal central portion 2425 of the tension member remain parallel to the centerline $CL_2$.

In some embodiments, the inner guide surface 2616 (or any of the surfaces within the second guide path 2615 or the first guide path 2515) can be coated, treated or otherwise produced to have a low-friction surface. For example, in some embodiments, the inner guide surface 2616 (or any of the surfaces within the second guide path 2615 or the first guide path 2515) can be characterized by a coefficient of friction of less than 0.1. In some embodiments, the inner guide surface 2616 (or any of the surfaces within the second guide path 2615 or the first guide path 2515) can be coated with a friction-reducing composition, such as a nitride coating.

In some embodiments, the first link 2510, the second link 2610, or any of the links described herein can include rollers, bearings, or other friction-reducing mechanism within the first guide path 2515, the second guide path 2615, or any of the guide paths described herein. For example, in some embodiments, the inner guide surface 2616 can be an outer surface of a pulley coupled to the second link 2610. In other embodiments the first link 2510, the second link 2610, or any of the links described herein can include rollers of the types shown and described in the U.S. Provisional Patent Application Ser. No. 62/639,628 (filed Mar. 7, 2018), entitled "Low-Friction Medical Tools Having Roller-Assisted Tension Members," which is incorporated herein by reference in its entirety.

Figure 8A:
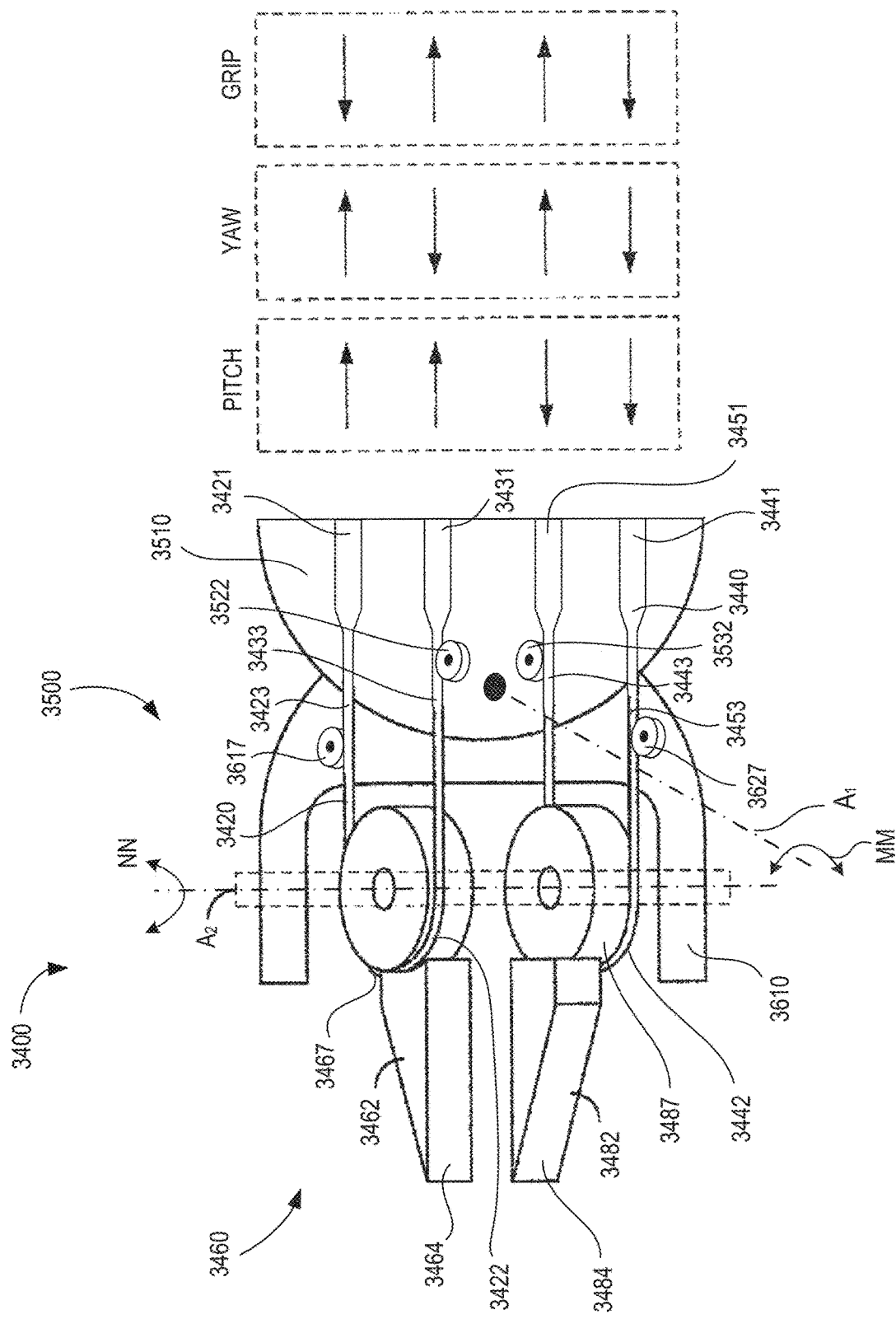
FIGS. 8A-8B are diagrammatic illustrations of a portion of an instrument system, according to embodiments.

Although the instrument 2400 is shown and described as including a single tool member 2462 and a single tension member (i.e., the tension member 2420), in other embodiments an instrument can include any suitable number of tension members or tool member. For example, in some embodiments, an instrument can include four tension members (or portions of tension members). FIG. 8A is a schematic illustration of a portion of an instrument 3400, according to an embodiment. The instrument 3400 includes a wrist assembly 3500, a first tension member 3420, a second tension member 3440, and an end effector 3460. The instrument 3400 is configured such that movement of various portions of the first tension member 3420 and the second tension member 3440 can produce movement of the wrist assembly 3500 about the pitch axis $A_1$, movement of the end effector 3460 about the yaw axis $A_2$, gripping motion of the end effector 3460, or any combination of these motions.

The wrist assembly 3500 (which functions as a joint assembly) includes a first link 3510 and a second link 3610. The first link 3510 is coupled to an instrument shaft (not shown) of the types shown and described herein. The second link 3610 has a proximal end portion and a distal end portion. The proximal end portion is rotatably coupled to the first link 3510 to form the wrist assembly 3500 having a first axis of rotation $A_1$ (which functions as the pitch axis, the term pitch is arbitrary) about which the second link 3610 can rotate relative to the first link 3510. The wrist assembly 3500 can include any suitable coupling mechanism. For example, in some embodiments, the second link 3610 can be coupled to the first link 3510 via a pinned joint of the types shown and described herein. In other embodiments the second link 3610 can be coupled to the first link 3510 via mating disc surfaces of the types shown and described herein.

The distal end portion of the second link 3610 is coupled to the end effector 3460. More specifically, the distal end portion of the second link 3610 is coupled to a pulley portion 3467 of a first tool member 3462 and a pulley portion 3487 of a second tool member 3482. This arrangement allows each of the tool member 3462 and the tool member 3482 to rotate relative to the wrist assembly 3500 about a second axis of rotation $A_2$. The second axis of rotation $A_2$ is non-parallel to the first axis of rotation $A_1$ and functions both as a yaw axis (the term yaw is arbitrary) as tool members rotate together and as a grip axis as tool members rotate in opposition to each other. Thus, the instrument 3400 provides for up to three degrees of freedom (i.e., a pitch motion about the first axis of rotation $A_1$, a yaw rotation about the second axis of rotation $A_2$, and a grip motion about the second axis of rotation $A_2$). Although the end effector 3460 is shown as being coupled to the second link 3610 via a pin connector, in other embodiments the end effector 3460 can be coupled to the wrist assembly 3500 by any suitable mechanism.

The end effector includes the first tool member 3462 and the second tool member 3482. The first tool member 3462 includes a contact portion 3464 and a pulley portion 3467, and the second tool member 3482 includes a contact portion 3484 and a pulley portion 3487. The contact portion 3464 and the contact portion 3484 are each configured to engage or manipulate a target tissue during a surgical procedure. For example, in some embodiments, the contact portions can include an engagement surfaces that function as a gripper, cutter, tissue manipulator, or the like. In other embodiments the contact portions can be an energized tool member that is used for cauterization procedures. As described above, the pulley portion 3467 and the pulley portion 3487 are each rotatably coupled to the second link 3610 such that the tool member 3462 can rotate relative to the wrist assembly 3500 via the second axis of rotation $A_2$. The pulley portions can include a contact surface about which the corresponding tension members (i.e., the first tension member 3420 and the second tension member 3440) are wrapped. The first tool member 3462 and the second tool member 3482 (or any of the tool members described herein) can be any suitable tool member of the types shown and described herein.

The first tension member 3420 (which can be a band or a cable) has a first proximal end portion 3421, a second proximal end portion 3431, and a distal end portion 3422. As shown, the distal end portion 3422 is wrapped about the pulley portion 3467 of the first tool member 3462. In this manner, the first proximal end portion 3421 and the second proximal end portion 3431 each extend through the first link 3510 and into the instrument shaft (not shown). Additionally, the first proximal end portion 3421 and the second proximal end portion 3431 are each coupled to an actuator (not shown) that can move each of the proximal end portions (as shown by the series of arrows labeled as PITCH, YAW, and GRIP). A first distal guide post 3617 is attached to the second link 3610 adjacent to a first intermediate portion 3423 of the first tension member 3420 that extends between the first proximal end portion 3421 and the distal end portion 3422 of the first tension member when the wrist assembly 3500 is in a first orientation shown in FIG. 8A. An outer surface of the first distal guide post 3617 contacts the first intermediate portion 3423 of the first tension member 3420 when the wrist assembly 3500 is in the first orientation. A first proximal guide post 3522 is attached to the first link 3510 adjacent to a second intermediate portion 3433 of the first tension member 3420 that extends between the second proximal end portion 3431 and the distal end portion 3422 of the first tension member when the wrist assembly 3500 is in the first orientation shown in FIG. 8A. An outer surface of the first proximal guide post 3522 contacts the second intermediate portion 3433 of the first tension member 3420 when the wrist assembly 3500 is in the first orientation.

The second tension member 3440 (which can be a band or a cable) has a third proximal end portion 3441, a fourth proximal end portion 3451, and a distal end portion 3442. As shown, the distal end portion 3442 is wrapped about the pulley portion 3487 of the second tool member 3482. In this manner, the third proximal end portion 3441 and the fourth proximal end portion 3451 each extend through the first link 3510 and into the instrument shaft (not shown). Additionally, the third proximal end portion 3441 and the fourth proximal end portion 3451 are each coupled to an actuator (not shown) that can move each of the proximal end portions (as shown by the series of arrows labeled as PITCH, YAW, and GRIP). A second proximal guide post 3532 is attached to the first link 3510 adjacent to a fourth intermediate portion 3443 of the second tension member 3440 that extends between the fourth proximal end portion 3451 and the distal end portion 3442 of the second tension member when the wrist assembly 3500 is in the first orientation shown in FIG. 8A. An outer surface of the second proximal guide post 3532 contacts the fourth intermediate portion 3443 of the second tension member 3440 when the wrist assembly 3500 is in the first orientation. A second distal guide post 3627 is attached to the second link 3610 adjacent to a third intermediate portion 3453 of the second tension member 3440 that extends between the third proximal end portion 3441 and the distal end portion 3442 of the second tension member when the wrist assembly 3500 is in a first orientation shown in FIG. 8A. An outer surface of the second distal guide post 3627 contacts the third intermediate portion 3453 of the second tension member 3440 when the wrist assembly 3500 is in the first orientation.

In some embodiments, the first tension member 3420 or the second tension member 3440 (or both) can be monolithically constructed such that the first proximal end portion, the second proximal end portion, and the distal end portion are all within a single element. In other embodiments however, the first tension member 3420 or the second tension member 3440 (or both) can include multiple separately constructed components (e.g., the first proximal end portion 3421 can be separately constructed from the second proximal end portion 3431). Moreover, the first tension member 3420 or the second tension member 3440 (or both) can have any suitable shape as described herein. In some embodiments, the first tension member 3420 or the second tension member 3440 (or both) can have varying cross-sectional areas. In some embodiments, the first tension member 3420 or the second tension member 3440 (or both) can be constructed from a series of laminates that are bonded together (e.g., via an adhesive). The laminates can be constructed from any suitable material, including tungsten, steel, or any suitable polymer. In some embodiments, the first tension member 3420 and the second tension member 3440 can be constructed as steel cables.

Changing the pitch, yaw, or grip of the instrument 3400 generally requires movements or actions respectively applied to each of the four proximal end portions (the first proximal end portion 3421, the second proximal end portion 3431, the third proximal end portion 3441, and the fourth proximal end portion 3451). The movement of the tension member portions can generally be performed one at a time or simultaneously in any desired combination to change the pitch, yaw, and grip of instrument 3400. For example, pitch axis rotations rotate the second link 3610 about the first axis of rotation $A_1$ (pitch axis), as shown by the arrow MM. For clockwise rotation about the pitch axis $A_1$, the actuators (not shown) pull in (i.e., move proximally) identical lengths of the first proximal end portion 3421 and the second proximal end portion 3431 while releasing (i.e., allowing to move distally) the same lengths of the third proximal end portion 3441 and the fourth proximal end portion 3451. This is illustrated by the arrows labeled as PITCH.

The first proximal end portion 3421 and the second proximal end portion 3431 apply forces to the second link 3610 at moment arms defined by the curved guide paths through the wrist assembly 3500. Similarly stated, the first link 3510 and the second link 3610 can define one or more curved guide paths that are offset from the pitch axis $A_1$ to produce a torque about the pitch axis $A_1$. The curved guide paths can be any of the curved guide paths described herein (e.g., the curved guide paths shown and described in connection with the wrist assembly 2500 or the wrist assembly 4500). Similarly, for counterclockwise rotation of the second link 3610 about the pitch axis $A_1$, the actuators pull in (i.e., move proximally) identical lengths of the third proximal end portion 3441 and the fourth proximal end portion 3451 while releasing (i.e., allowing to move distally) the same lengths of the first proximal end portion 3421 and the second proximal end portion 3431.

Yaw rotations are the rotation of the first tool member 3462 and the second tool member 3482 about the second axis of rotation $A_2$ (yaw axis) in the same direction and through the same angle. In particular, when the actuators pull in (i.e., move proximally) a length of the first proximal end portion 3421 and release (i.e., allow to move distally) an equal length of the second proximal end portion 3431, the first tool member 3462 will rotate in a clockwise direction about the yaw axis $A_2$ (see the arrow NN). For this rotation, the curved guide path or pulley surface of the pulley portion 3467 defines the moment arm at which force transmitted via the first tension member 3420 is applied. The resulting torque causes the first tool member 3462 to rotate clockwise. During this movement, the first proximal end portion 3421 and the second proximal end portion 3431 each slide within the curved guide paths of the second link 3610. If, at the same time, the actuators pull in a length of the fourth proximal end portion 3451 and release the same length of the third proximal end portion 3441, the second tool member 3482 will rotate clockwise through an angle that is the same as the angle through which the first tool member 3462 rotates. Accordingly, the first tool member 3462 and the second tool member 3482 maintain their positions relative to each other and rotate as a unit through a yaw angle. Counterclockwise rotation of the end effector 3460 is similarly accomplished when the actuators pull in equal lengths of the second proximal end portion 3431 and the third proximal end portion 3441 while releasing the same lengths of the first proximal end portion 3421 and the fourth proximal end portion 3451. This is illustrated by the arrows labeled as YAW.

Grip rotations are rotations of the first tool member 3462 and the second tool member 3482 about the yaw axis $A_2$ in opposite directions and through the same angle. To open the grip of the end effector 3460, the actuators pull in equal lengths of the first proximal end portion 3421 and the third proximal end portion 3441 while releasing the same lengths of the second proximal end portion 3431 and the fourth proximal end portion 3451. This causes the first tool member 3562 to rotate in an opposite direction from the second tool member 3482. To close the grip of the end effector, the actuators pull in equal lengths of the second proximal end portion 3431 and the fourth proximal end portion 3451 while releasing the same lengths of the first proximal end portion 3421 and the third proximal end portion 3441. This causes the first tool member 3562 to rotate towards the second tool member 3482. When contact portion of the tool members come into contact, the tension in the second proximal end portion 3431 and the fourth proximal end portion 3451 can be kept greater than the tension in the first proximal end portion 3421 and the third proximal end portion 3441 to maintain the desired gripping forces.

The proximal guide posts (first proximal guide post 3522 and second proximal guide post 3532) are each coupled to the first link 3510 on opposite sides of the pitch axis $A_1$ between the first tension member 3420 and the second tension member 3440. The outer surface of the first proximal guide post 3522 contacts the second intermediate portion 3433 of the first tension member while in the orientation shown in FIG. 8A. Likewise, the outer surface of the second proximal guide post 3532 contacts the fourth intermediate portion 3443 of the second tension member while in the orientation shown in FIG. 8A. As such, the outer surfaces of the proximal guide posts 3522, 3532 guide the position and orientation of the first tension member 3420 and the second tension member 3440 as the tension members move. As such, the proximal guide posts 3522, 3532 maintain the inner intermediate portions (second intermediate portion 3433 and fourth intermediate portion 3443) of the first and second tension members 3420, 3440 in parallel alignment with the instrument shaft regardless of the pitch, yaw and grip movements of the wrist assembly 3500. Maintaining this parallel alignment prevents interfering contact between the first and second tension members 3420, 3440 and other objects from occurring during movements of the wrist assembly that can cause the tension members to bind or become entangled. In addition, maintaining this parallel alignment reduces friction during operations of the wrist assembly 3500 by avoiding rubbing or other frictional contact from occurring between the first and second tension members 3420, 3440 and other portions of the wrist assembly 3500 and its components.

Further, first and second proximal guide posts 3522, 3532 advantageously reduce friction at high tensile stress positions along the tension members 3420, 3440. In particular, each of the first and second proximal guide posts 3522, 3532 is located on the first link 3510 on opposite sides of the pitch pivot $A_1$, about which second link 3610 rotates for pitch movements. When high pitch movements are made, high tensile stresses are applied to the first and second tension members 3420, 3440 located on the side opposite the direction of pitch rotation. The first and second proximal guide posts 3522, 3532 can reduce friction at the high tensile stress locations proximate the pitch pivot $A_1$, which can reduce wear on the first and second tension members 3420, 3440 and enhance operation of the wrist assembly 3500.

The distal guide posts (first distal guide post 3617 and second distal guide post 3627) are each coupled to the second link 3610 on opposite, outer portions of the second link 3610. The outer surface of the first distal guide post 3617 contacts the first intermediate portion 3423 of the first tension member while in the orientation shown in FIG. 8A. Likewise, the outer surface of the second distal guide post 3627 contacts the third intermediate portion 3453 of the second tension member while in the orientation shown in FIG. 8A. As such, the outer surface of each of the distal guide posts 3617, 3627 guide the position and orientation of the first tension member 3420 and the second tension member 3440. The distal guide posts 3617, 3627 are coupled to the second link 3610 that rotates during pitch movements of the wrist assembly 3500. As such, the distal guide posts 3617, 3627 guide the outer intermediate portions (third intermediate portion 3453 and first intermediate portion 3423) of the first and second tension members 3420, 3440 during pitch rotation movements to keep the first and second tension members 3420, 3440 properly positioned to avoid them catching on objects during movements of the wrist assembly and binding or becoming tangled. Further, distal guide posts 3617, 3627 advantageously guide the paths of the first and second tension members 3420, 3440 throughout the range of motion for pitch movements with low friction.

The first and second proximal guide posts 3522, 3532 and the first and second distal guide posts 3617, 3627 can be any suitable guide post of the types shown and described herein. For example, in some embodiments, any of the first and second proximal guide posts 3522, 3532 and the first and second distal guide posts 3617, 3627 can have a radius that is less than a radius of curvature of any of the guide paths defined within the wrist assembly 3500. Moreover, although the first and second proximal guide posts 3522, 3532 and the first and second distal guide posts, 3617, 3627 are shown and described as being in contact with their respective portions of the first tension member 3420 and the second tension member 3440, when the wrist assembly is in a second configuration, any of the first and second proximal guide posts 3522, 3532 and the first and second distal guide posts 3617, 3627 can be spaced apart from their respective portions of the first tension member 3420 and the second tension member 3440.

Figure 8B:
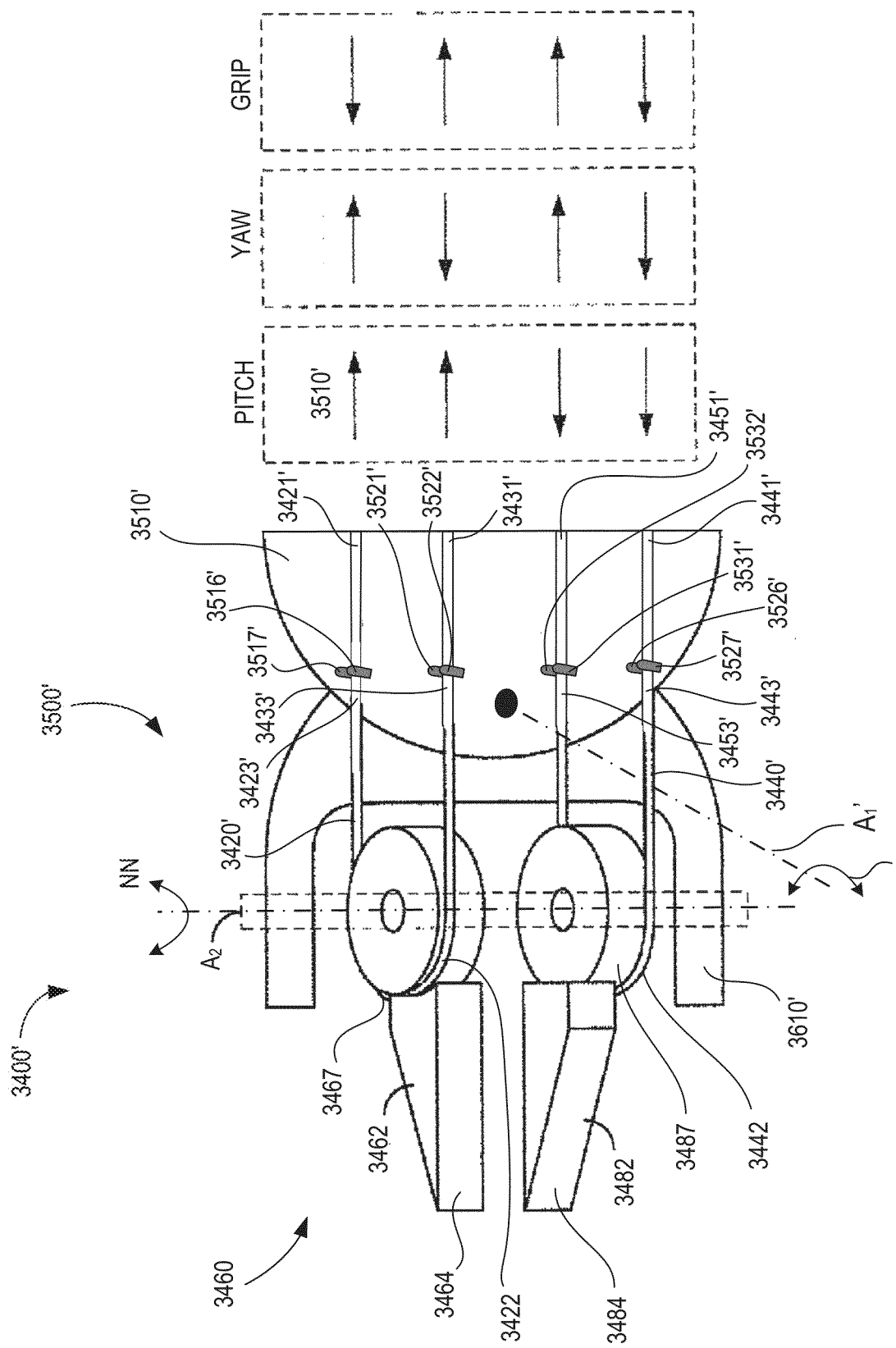

The wrist assembly 3500 (and any of the wrist assemblies described herein) can include any suitable structure to define any suitable guide paths within which the tension members move including using multiple guide posts to maintain the proximal end portions of the tension members in parallel alignment with their connections in the shaft throughout various movements of the wrist assembly. For example, referring to FIG. 8B, in some embodiments, a first link 3510' includes pairs of inner and outer guide posts that together maintain the proximal end portions of each tension member in parallel alignment with the shaft, which can avoid frictional contact of the tension members with portions of the wrist assembly during movements.

A first pair of guide posts includes a first inner guide post 3516' and a first outer guide post 3517' located along the first intermediate portion 3423' of the first tension member 3420' between the first proximal end portion 3421' and the second proximal end portion 3431'. The first inner guide post 3516' is located on an inner side of the first intermediate portion 3423' and first outer guide post 3517' is located on an outer side of the first intermediate portion 3423'. In a similar manner, a second pair of guide posts includes a second inner guide post 3521' located on an inner side of the second intermediate portion 3433' of the first tension member 3420', and a second outer guide post 3522' located on an outer side of the second intermediate portion 3433'. Further, a third pair of guide posts includes a third inner guide post 3526' located on an inner side of the third intermediate portion 3453' of the second tension member 3440', and third outer guide post 3527' located on an outer side of the third intermediate portion 3453'. Likewise, a fourth pair of guide posts includes a fourth inner guide post 3531' located on an inner side of the fourth intermediate portion 3443' of the second tension member 3420', and a fourth outer guide post 3532' located on an outer side of the fourth intermediate portion 3443'.

The guide posts of each of the pairs are co-located along a corresponding intermediate portion of the tension members such that each pair forms a goal-post type guide along, and on each side of, the corresponding intermediate portion (3423', 3433', 3443', 3453') that maintains the corresponding first tension member portion (3421', 3431', 3441', and 3451') in parallel alignment with the corresponding actuator (not shown). The guide post pairs maintain this parallel alignment while the wrist assembly 3500' is in the first orientation shown in FIG. 8B and in other orientations, as well as during movements of the wrist assembly 3500'. Each of the inner guide posts (3516', 3521', 3526' and 3531') in each of the pairs can be spaced apart from the corresponding outer guide post (3517', 3522', 3527' and 3532') such that the corresponding intermediate portion (3523', 3233', 3443' and 3553') disposed therebetween does not contact the guide posts while in the first orientation shown in FIG. 8B and, thus, can move freely in the longitudinal direction of the tension member 3220' and 3420' without frictional contact with the guide posts. As such, the tension members 3420' and 3440' can move longitudinally in-line with their longitudinal axis while in the first orientation with reduced friction. Further, when the second link 3610' rotates with respect to the first link 3510' about the first axis $A_1'$, the pairs of guide posts can maintain the portions of the first and second tension members 3420' and 3440' disposed between the pairs of guide posts and the corresponding actuator (not shown) in parallel alignment with the corresponding actuator, which can avoid frictional contact with portions of the wrist assembly 3500 and reduce the likelihood of the tension members binding.

FIGS. 9-17 are various views of an instrument 4400, according to an embodiment. In some embodiments, the instrument 4400 or any of the components therein is optionally parts of a surgical assembly that performs minimally invasive surgical procedures, and which can include a manipulator unit, a series of kinematic linkages, a series of cannulas, or the like. The instrument 4400 (and any of the instruments described herein) can be used in any suitable surgical system, such as the MIRS system 1000 shown and described above. The instrument 4400 includes a transmission mechanism 4700 (e.g., transmission assembly) (that can function as an actuator mechanism), an instrument shaft 4410, a wrist assembly 4500, and an end effector 4460.

Figure 10:
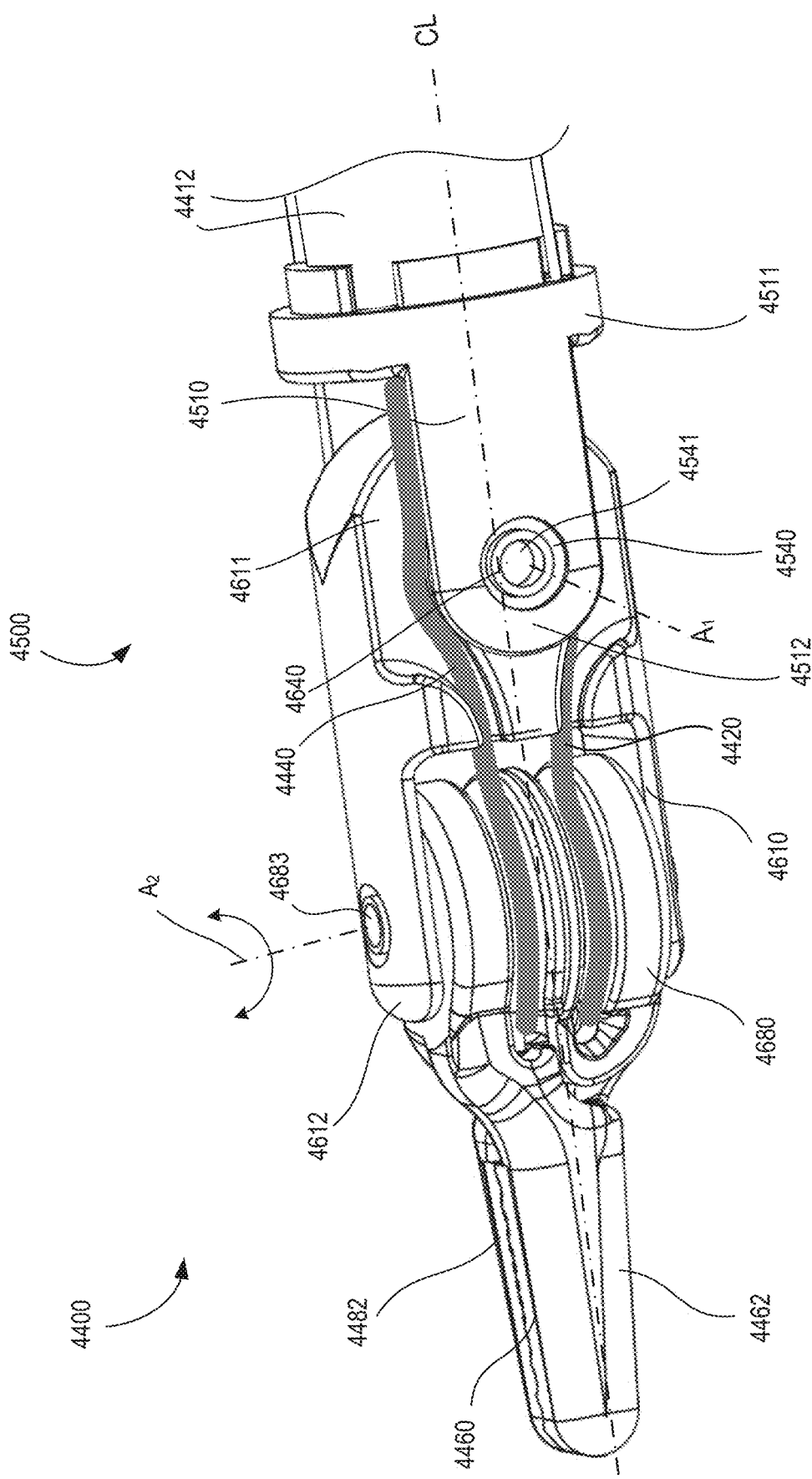
FIG. 10 is an enlarged perspective view of a distal end portion of the instrument indicated by the region Z shown in FIG. 9.

Referring to FIG. 10, the instrument 4400 also includes a first tension member 4420 and a second tension member 4440 that couple the transmission mechanism 4700 to the wrist assembly 4500. The instrument 4400 is configured such that movement of the tension members can produce rotation of the wrist assembly 4500 (i.e., pitch rotation) about a first axis of rotation $A_1$, yaw rotation of the end effector 4460 about a second axis of rotation $A_2$, grip rotation of the tool members of the end effector 4460 about the yaw axis, or any combination of these movements. Changing the pitch, yaw, or grip of the instrument 4400 can be performed by manipulating the four tension members in similar manner as that described above for the instrument 3400. Thus, the specific movement of each of the four tension members to accomplish the desired motion is not described below. Although shown and described as including two tension members that are wrapped about the end effector 4460 resulting in four proximal end tension member portions (i.e., the four-tension member arrangement), in other embodiments the instrument 4400 can include additional tension members that separately change the pitch of the instrument 4400.

The transmission mechanism 4700 produces movement of each of the first tension member 4420 and the second tension member to produce the desired movement (pitch, yaw, or grip) at the wrist assembly 4500. Specifically, the transmission mechanism 4700 includes components and controls to move some of the tension members in a proximal direction (i.e., to pull in certain tension members) while simultaneously allowing the distal movement (i.e., releasing or "paying out") of other of the tension members in equal lengths. In this manner, the transmission mechanism 4700 can maintain the desired tension within the tension members, and can ensure that the lengths of the tension members are conserved (i.e., moved in equal amounts) during the entire range of motion of the wrist assembly 4500. In some embodiments, for example, the transmission mechanism 4700 can be any of the transmission assemblies shown and described in International Patent Application No. PCT/US2017/062258, (filed Nov. 14, 2017), entitled "Cable Length Conserving Medical Instrument," which is incorporated herein by reference in its entirety. In other embodiments however, conservation of the lengths of the tension members is not required.

In some embodiments, the transmission mechanism 4700 can include one or more linear actuators that produce translation (linear motion) of a portion of the tension members. Such transmission mechanisms can include, for example, a gimbal, a lever, or any other suitable mechanism to directly pull (or release) an end portion of any of the tension members. For example, in some embodiments, the transmission mechanism 4700 can include any of the transmission assemblies or components described in U.S. Patent Application Pub. No. US 2015/0047454 A1 (filed Aug. 15, 2014), entitled "Lever Actuated Gimbal Plate," or U.S. Pat. No. 6,817,974 B2 (filed Jun. 28, 2001), entitled "Surgical Tool Having Positively Positionable Tendon-Actuated Multi-Disk Wrist Joint," each of which is incorporated herein by reference in its entirety. In other embodiments however, the transmission mechanism 4700 can include a capstan or other motor-driven roller that rotates or "winds" a portion of any of the tension members to produce the desired tension member movement. For example, in some embodiments, the transmission mechanism 4700 can include any of the backend assemblies or components described in U.S. Pat. No. 9,204,923 B2 (filed Jul. 16, 2008), entitled "Medical Instrument Electronically Energized Using Drive Cables," which is incorporated herein by reference in its entirety.

The instrument shaft 4410 can be any suitable elongated shaft that couples the wrist assembly 4500 to the transmission mechanism 4700. Specifically, the instrument shaft 4410 includes a proximal end portion 4411 that is coupled to a housing of the transmission mechanism 4700, and a distal end portion 4412 that is coupled to the wrist assembly 4500. The instrument shaft 4410 defines a passageway or series of passageways through which the tension members and other components (e.g., electrical wires, ground wires, or the like) can be routed from the transmission mechanism 4700 to the wrist assembly 4500. Although shown as being cylindrical, in other embodiments the instrument shaft 4410 can have any suitable shape.

Referring to FIG. 10-13, the wrist assembly 4500 includes a proximal first link 4510 and a distal second link 4610. The first link 4510 has a proximal end portion 4511 and a distal end portion 4512. The proximal end portion 4511 is coupled to the distal end portion 4412 of the instrument shaft 4410. The proximal end portion 4511 can be coupled to the instrument shaft 4410 via any suitable mechanism. For example, in some embodiments, the proximal end portion 4511 can be matingly disposed within a portion of the instrument shaft (e.g., via an interference fit). As shown, the proximal end portion 4511 can include one or more protrusions, recesses, openings, or connectors that couple the proximal end portion 4511 to the instrument shaft. The proximal end portion 4511 can be fixedly coupled to the instrument shaft 4410 via an adhesive bond, a weld, or any other permanent coupling mechanism (i.e., a coupling mechanism that is not intended to be removed during normal use).

The distal end portion 4512 includes a joint portion 4540 that is rotatably coupled to a mating joint portion 4640 of the second link 4610. In this manner, the first link 4510 and the second link 4610 form the wrist assembly 4500 having a first axis of rotation $A_1$ (also referred to as the pitch axis) about which the second link 4610 can rotate relative to the first link 4510. A pin 4541 extends through the joint portion 4540 of the distal end portion 4512 and the joint portion 4640 of the second link 4610 to rotatably couple the second link 4610 to the first link 4510. As shown in FIG. 10, the first link 4510 and the second link 4610 define a longitudinal centerline CL that intersects the pitch axis $A_1$ when the instrument is in an initial (or "straight") configuration.

Figure 11:
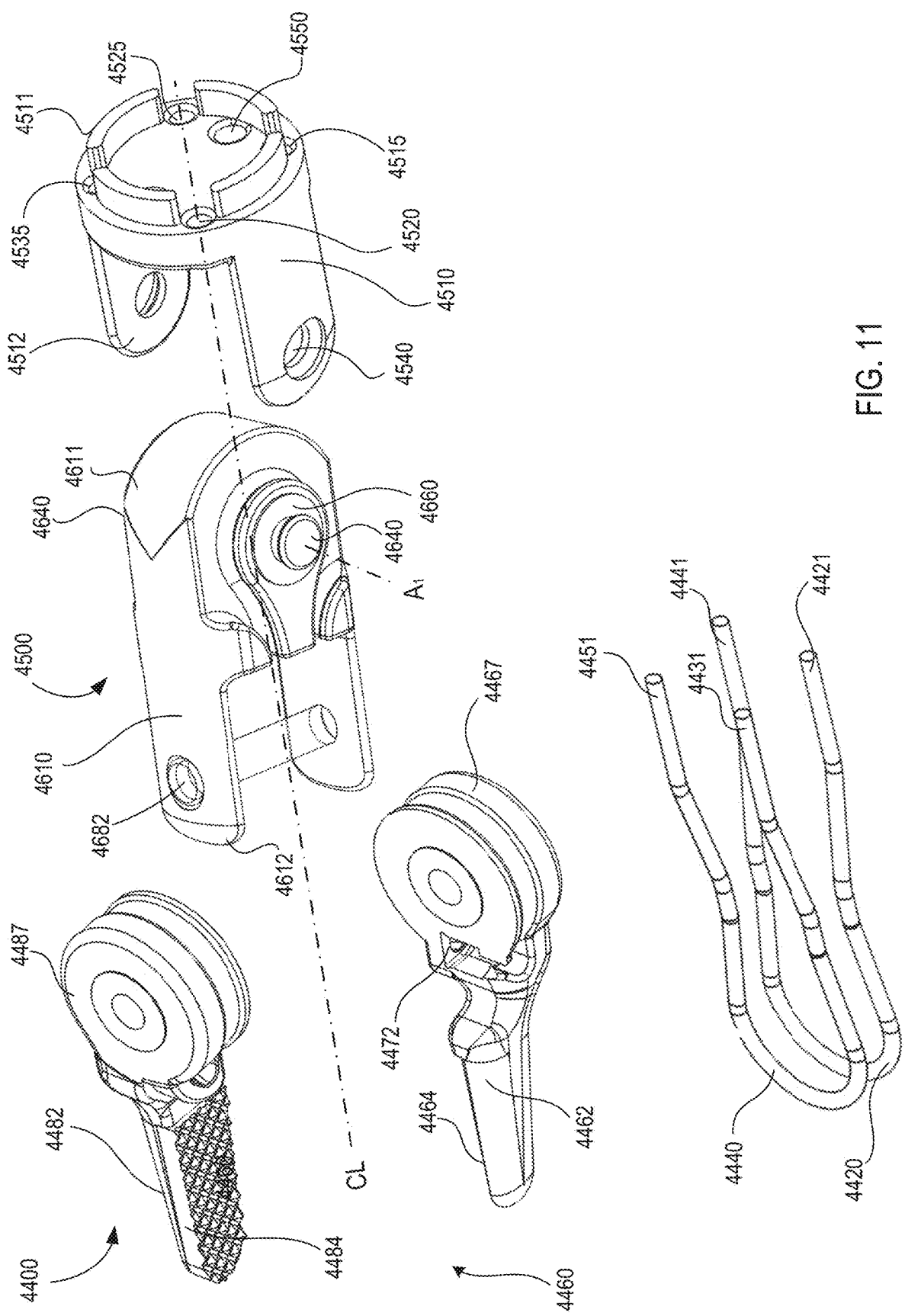
FIG. 11 is a perspective view of the distal end portion of the instrument of FIG. 10 shown in an exploded view.

Referring to FIG. 11, a first guide path 4515, a second guide path 4520, a third guide path 4525, and a fourth guide path 4535 are defined in the first link 4510. A first proximal end portion 4421 of the first tension member 4420 is movably disposed within the first guide path 4515. A first proximal end portion 4431 of the second tension member 4440 is movably disposed within the second guide path 4520. A second proximal end portion 4441 of the first tension member 4420 is movably disposed within the third guide channel 4525. A second proximal end portion 4451 of the second tension member 4440 is movably disposed within the fourth guide channel 4535. In this manner, the portions of the first tension member 4420 coupled to the first tool member 4462 are within guide channels that are separated. In some embodiments, however, the first guide path 4515 can be combined with the third guide channel 4525 to form a single channel within which the first proximal end portion 4421 and the second proximal end portion 4441 of the first tension member 4420 are disposed. In this manner, the portions of the second tension member 4440 coupled to the second tool member 4482 are within guide channels that are separated. In some embodiments, however, the second guide path 4520 can be combined with the fourth guide channel 4535 to form a single channel within which the first proximal end portion 4431 and the second proximal end portion 4451 of the second tension member 4440 are disposed.

The first link 4510 also defines additional bores or guide channels 4550. The additional guide channels 4550 can contain (or allow passage of) various components of the wrist assembly, such as, for example, electrical wires. In some embodiments, the guide channels 4550 can contain additional tension members (not shown) that are coupled to the second link 4610 and that cause the second link 4610 to rotate relative to the first link 4510 (i.e., a pitch rotation) when the tension members are moved. In this manner, the wrist assembly 4500 can be a six-tension member configuration (two tension members or portions of tension members controlling the pitch rotation and four tension members or portions of tension members controlling the yaw and grip rotations).

The distal second link 4610 has a proximal end portion 4611 and a distal end portion 4612. As described above, the proximal end portion 4611 includes a joint portion 4640 that is rotatably coupled to the joint portion 4540 of the first link 4510. The distal end portion 4612 of the second link 4610 includes a connector 4680 that is coupled to the end effector 4460. In this manner, the first tool member 4462 and the second tool member 4482 can rotate relative to the second link 4610 about a second axis of rotation (also referred to as the yaw axis) $A_2$. The connector 4680 is a pin-type connector and includes the pin 4683 which is supported by (and placed within) the pin openings 4682. In some embodiments, the connector 4680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIG. 10, the second axis of rotation $A_2$ (also referred to as the yaw axis) is non-parallel to the pitch axis $A_1$. Thus, the instrument 4400 provides for up to three degrees of freedom (i.e., a pitch motion about the first axis of rotation $A_1$, a yaw rotation about the second axis of rotation $A_2$, and a grip motion about the second axis of rotation $A_2$).

Referring to FIGS. 11, 14A, 14B, 15A-C, the second link 4610 defines a first thimble structure 4660, and a second thimble structure 4665. The first thimble structure 4660 and the second thimble structure 4665 are each formed as raised structures disposed on opposite side portions of the second link 4610 that each extend laterally outward from a longitudinal centerline CL of the second link 4610 (see FIG. 15A). Each of the first and second thimble structures 4660, 4665 includes a smooth, contoured outer side surface 4661, 4662 that substantially extends around a perimeter of the corresponding first and second thimble structure 4660, 4665 (see FIG. 14A). The first and second thimble structures 4660, 4665 are disposed on opposite side portions of the second link 4610 such that the contoured outer side surfaces 4661, 4662 each extend around an opposite end of the joint portion 4640 that connects with the joint portion 4540 of the first link, and each of the outer side surfaces extends around the first axis of rotation $A_1$.

The contoured outer side surfaces 4661, 4662 of the first and second thimble structures 4660, 4665 are configured to act as support surfaces for the tension members 4420, 4440 that can protect the tension members from bending or kinking at high load-bearing regions within the second link 4610. As discussed below, the contoured outer side surfaces 4661, 4662 are also configured to help guide the tension members 4420, 4440 through curved guide paths 4615, 4620 that are defined in one side of the second link 4610 of the wrist assembly 4500 (see FIG. 14B), as well as through similar curved guide paths (not shown) on the opposite side of the second link. Referring to FIGS. 15B and 15C, each of the contoured outer side surfaces 4661, 4662 are shaped to include a groove that can enhance retention of portions of the tension members 4420, 4440 that are in contact with the contoured outer side surfaces. The radius of curvature for any point of contact along the contoured outer side surfaces 4661, 4662 with a portion of one of the tension member 4420, 4440 can be determined as an effective radius of curvature, $R_{bend}$. As shown in FIGS. 15A and 15B, the effective radius of curvature, $R_{bend}$, at any point along the contoured outer side surfaces 4661, 4662 is the sum of the instant radius of curvature within the groove at the point along the contoured outer side surfaces plus half the thickness (i.e., the radius) of the tension member.

Figure 15A:
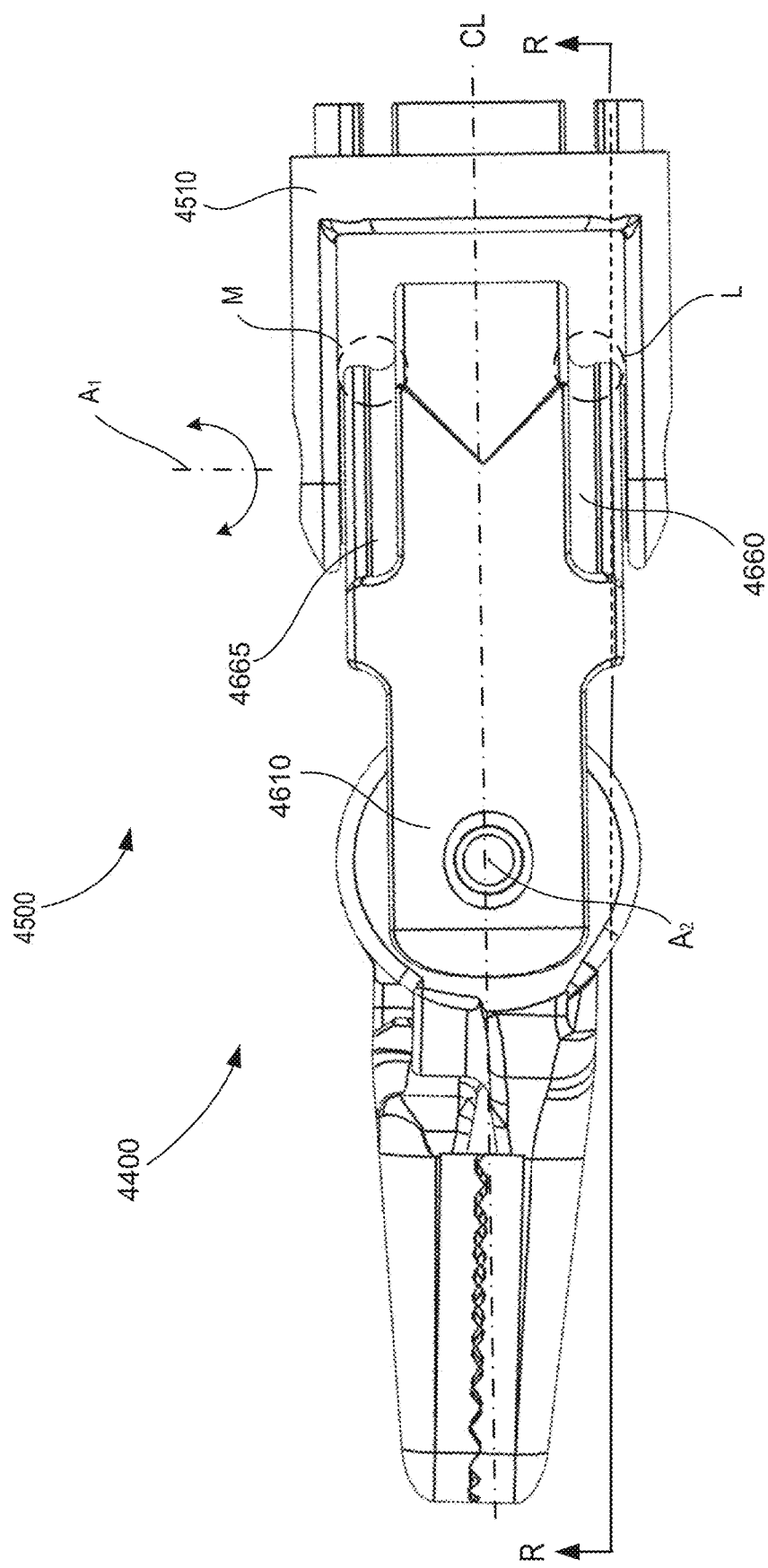
FIG. 15A is a top view of the distal end portion of the instrument of FIG. 10 in a first orientation.
Figure 15B:
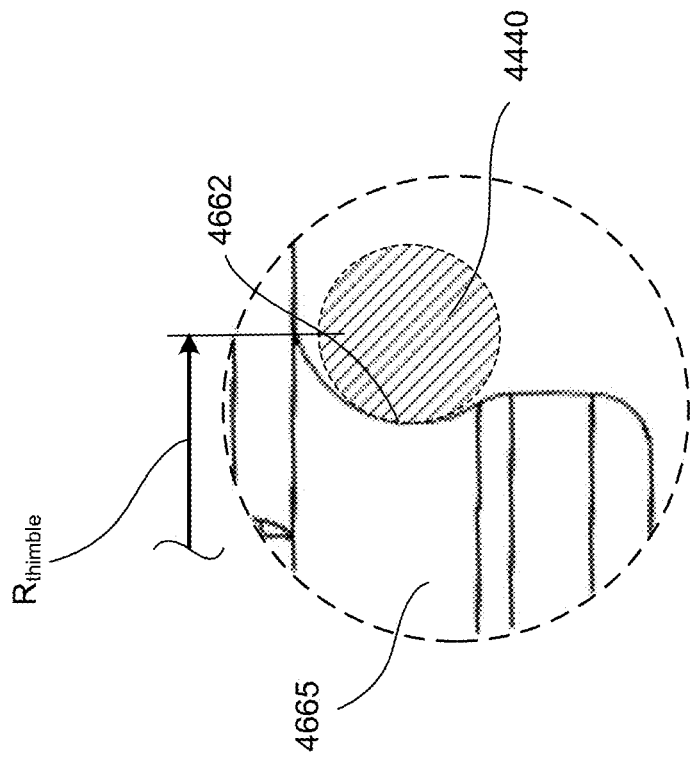
FIGS. 15B and 15C are enlarged top views of the portions indicated by the regions L and M shown in FIG. 15A, showing a thimble structure of the second link of the instrument of FIG. 10.
Figure 16A:
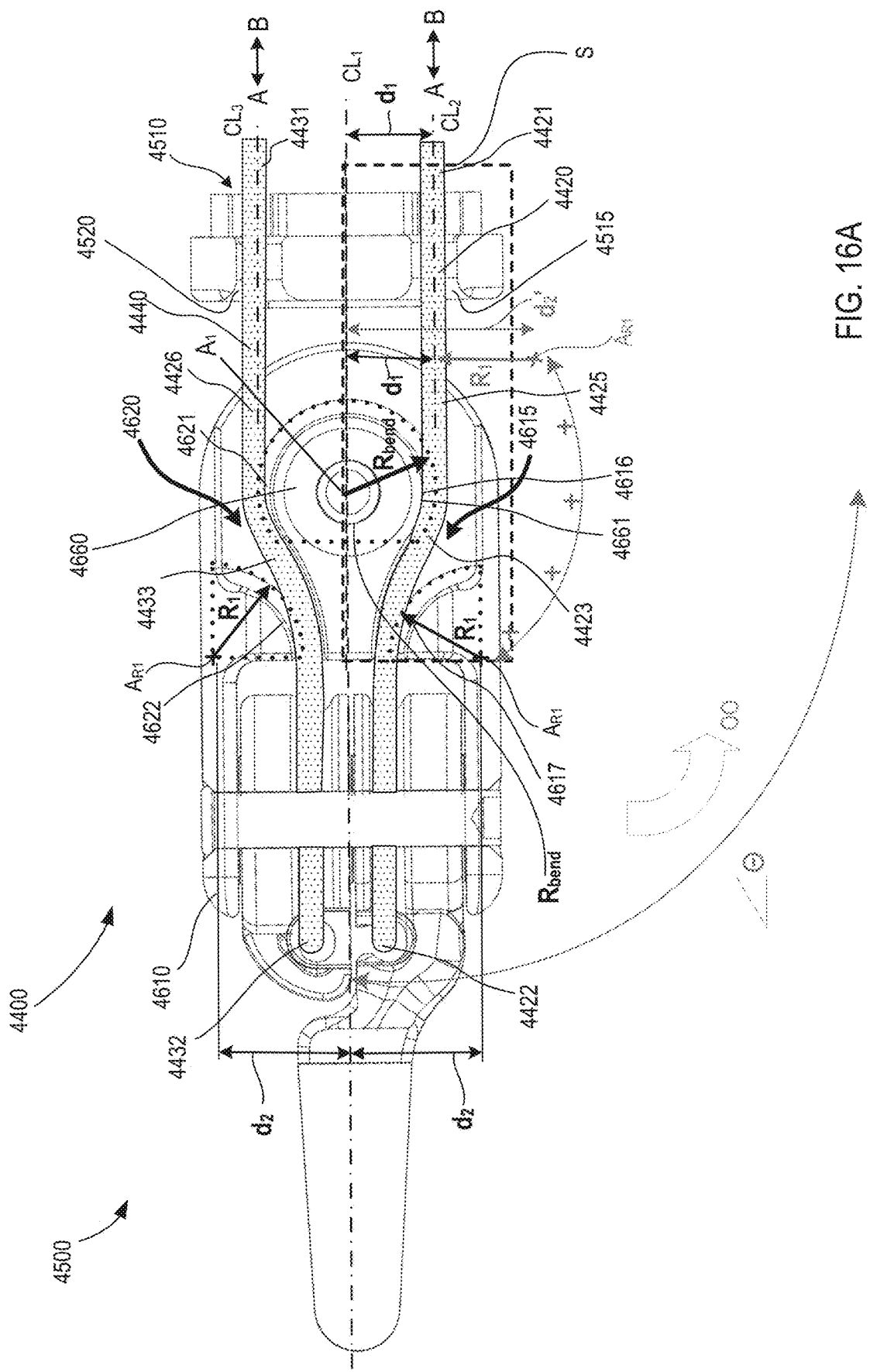
FIG. 16A is a cross-sectional view of the distal end portion of the instrument of FIG. 10, taken along line R-R shown in FIG. 15A.
Figure 16B:
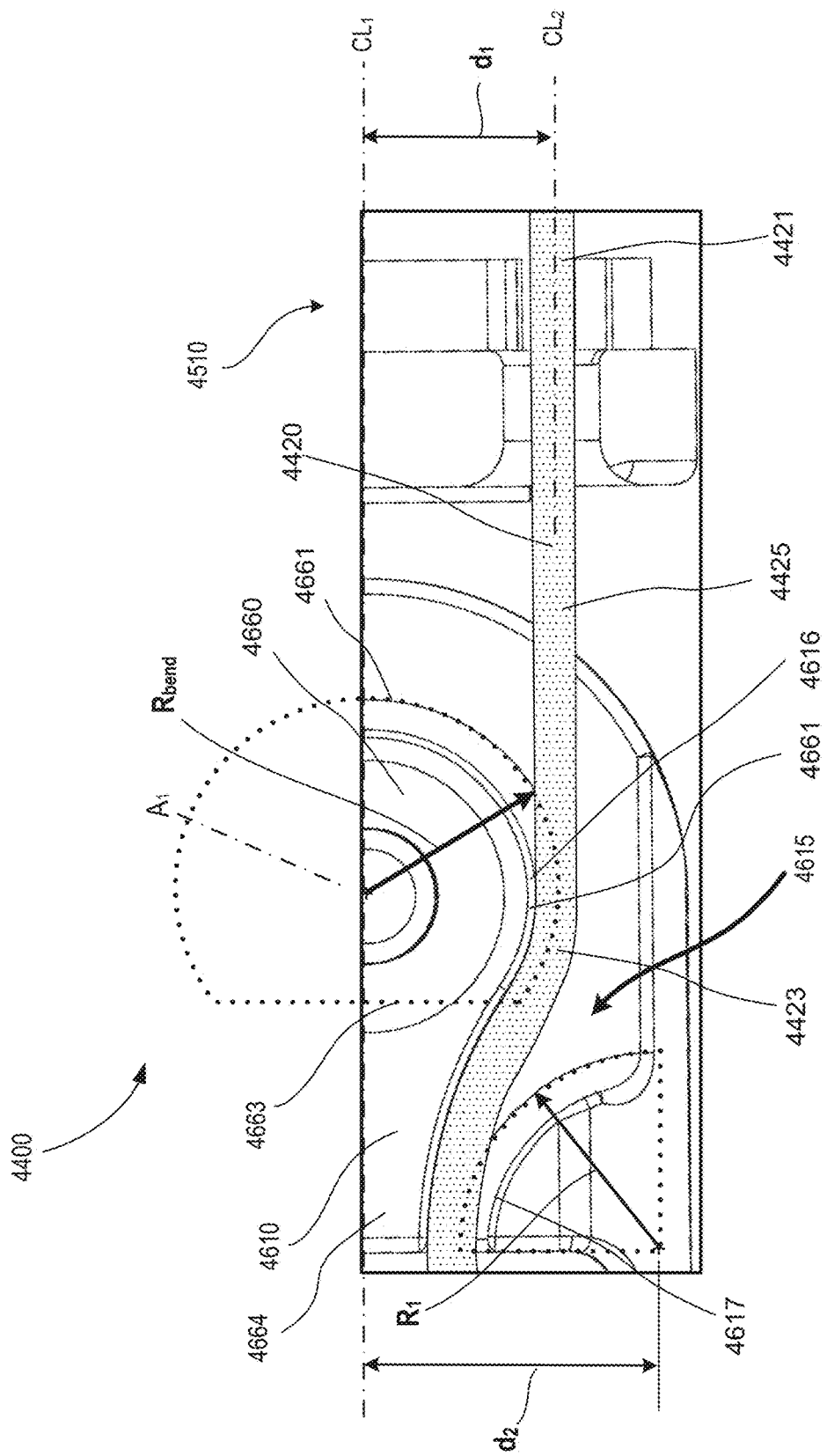
FIG. 16B is an enlarged cross-sectional view of the distal end portion of the instrument indicated by region S shown in FIG. 16A.

Referring to FIGS. 16A and 16B, this arrangement of the first and second thimble structures 4660, 4665 allows a first distal central portion 4423 of the first tension member 4420 and a first distal central portion 4433 of the second tension member 4440 to each contact a portion of the outer side surface 4661 of the first thimble structure, depending on the orientation of the wrist assembly 4500. Although not shown, a second central portion 4443 of the first tension member 4420 and a second central portion 4443 of the second tension member 4440 can similarly contact the outer side surface 4662 of the second thimble structure 4665 located on the opposite side of the second link 4610. Thus, this arrangement provides one thimble structure that functions to engage and define a portion of a guide path for two distinct tension member portions. As shown in FIGS. 15B and 15B, the effective radius of a proximal end of the contoured outer side surfaces 4661, 4662 of the first and second thimble structures 4660, 4665 is identified as $R_{bend}$, and is selected to produce the desired guide path, as described further below.

Figure 14A:
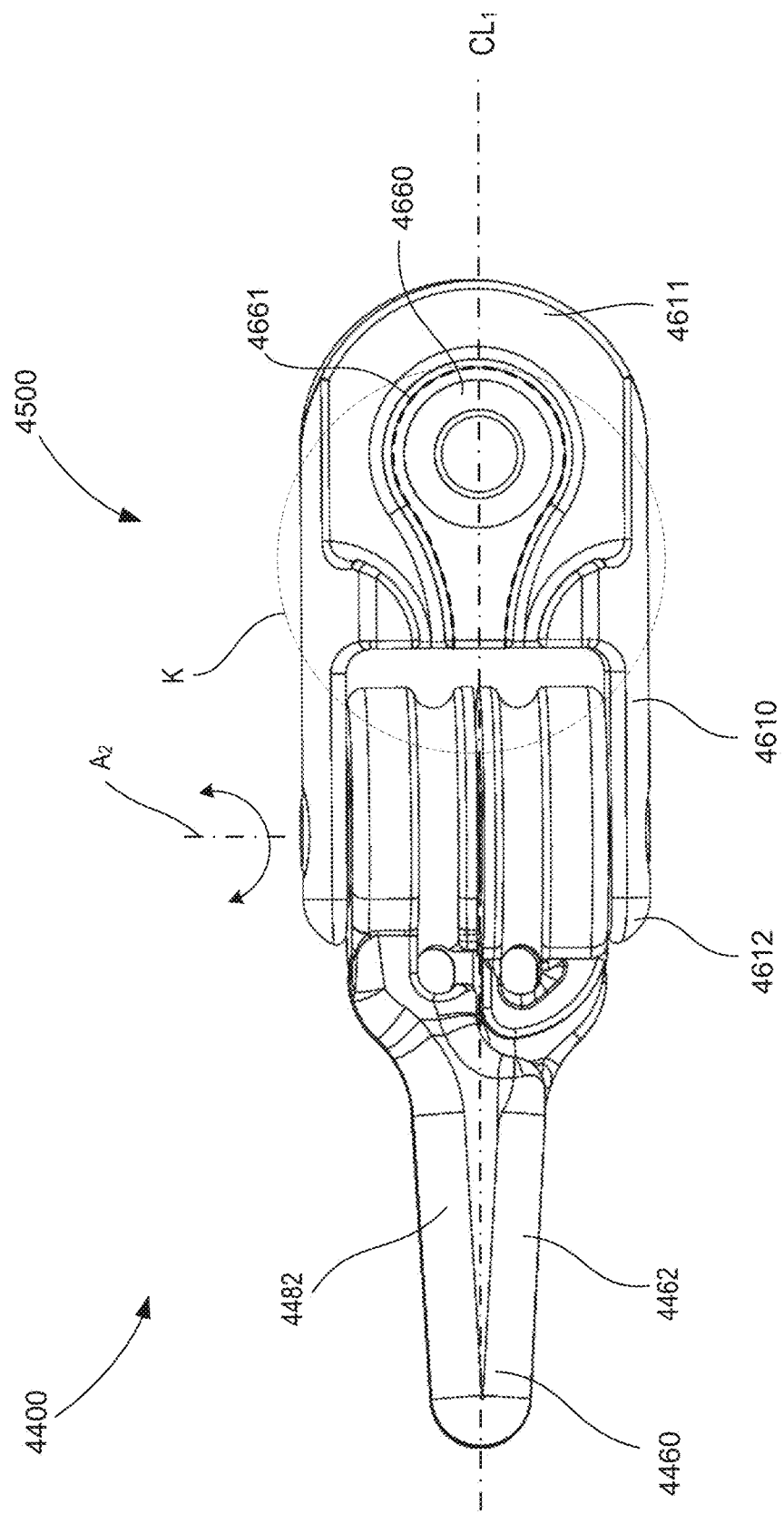
FIG. 14A is a side view of the distal end portion of the instrument of FIG. 10 in a first orientation, taken along line Y-Y shown in FIG. 9, and shown with the first link and the tension members removed to expose portions of the guide paths.
Figure 14B:
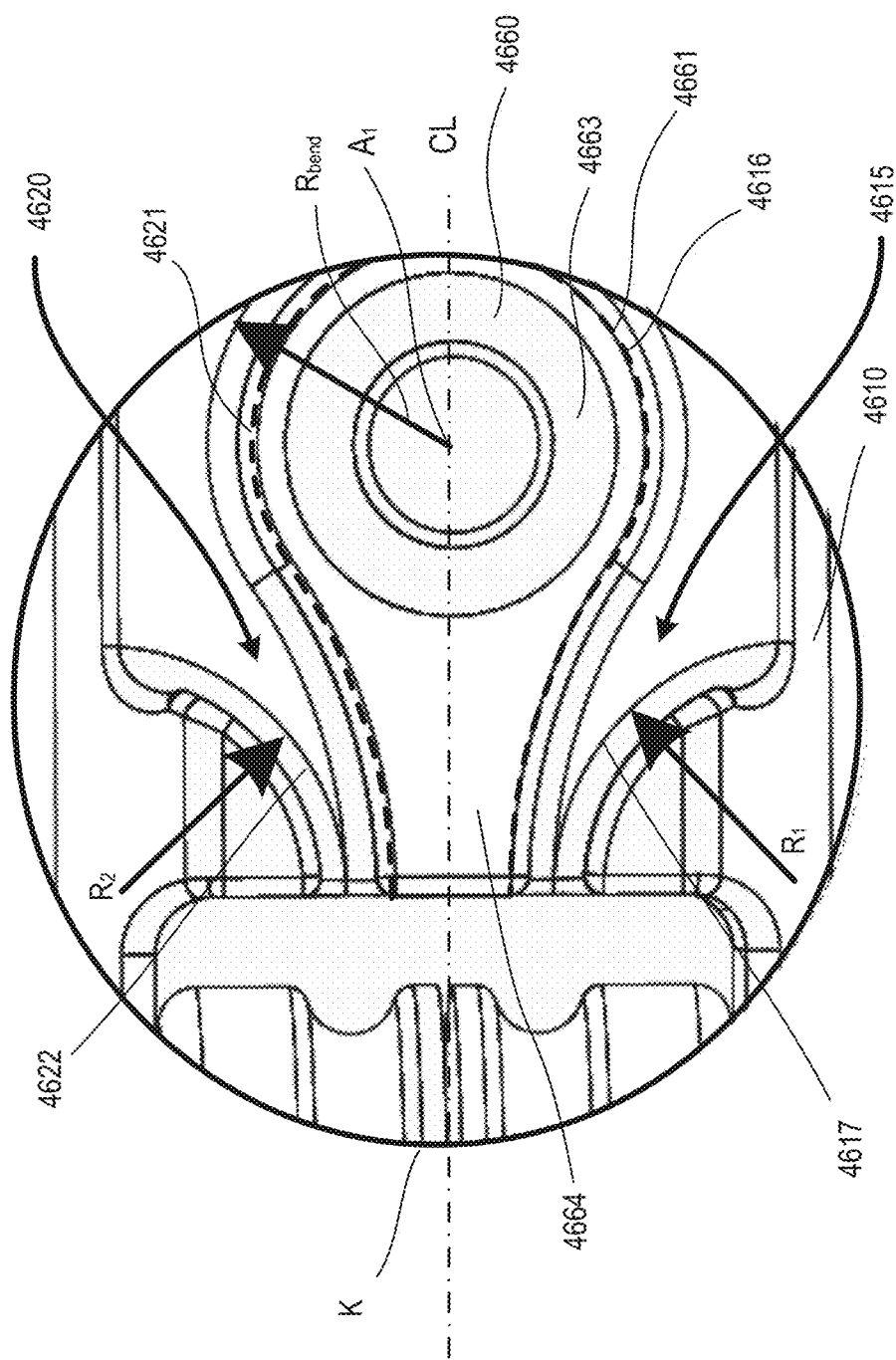
FIG. 14B is an enlarged side view of a distal end portion of the instrument of FIG. 10 in the first orientation, indicated by the region K shown in FIG. 14A.
Figure 15C:
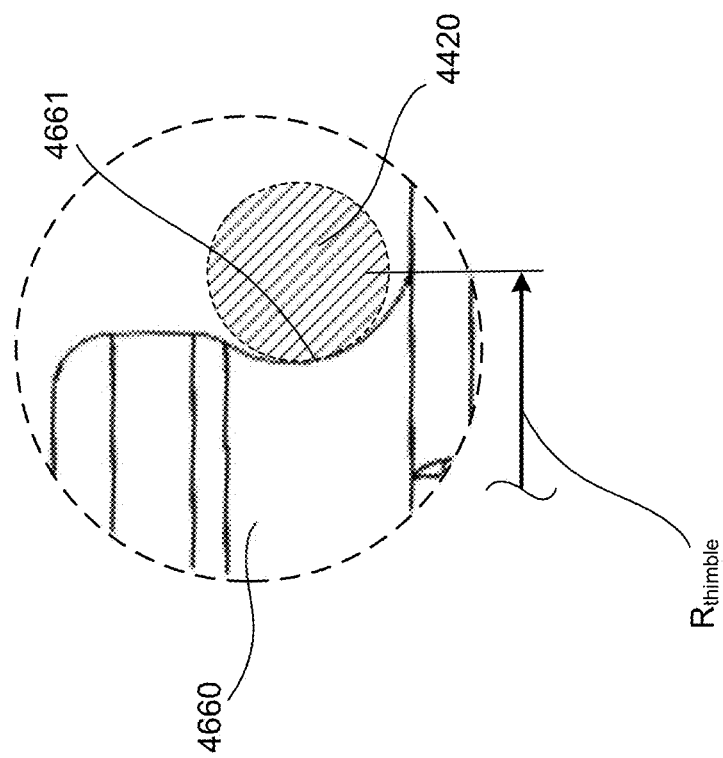

Referring to FIG. 14B, the second link 4610 defines a first curved guide path 4615 and a second curved guide path 4620. The second link 4610 also includes a first guide surface 4616 and a second guide surface 4621 that are portions of the contoured outer side surface 4661 of the first thimble structure 4660. The second link 4610 also includes a third guide surface 4617 that is aligned with a portion of the first curved guide path 4615, and a fourth guide surface 4622 that is aligned with a portion of the second curved guide path 4620. The first and second curved guide paths 4615, 4620 (and therefore the portions of the first tension member 4420 and the second tension member 4440 therein) are each offset from the longitudinal centerline CL and the first axis of rotation $A_1$. In this manner, application of a force via the first tension member 4420 or the second tension member 4440 produces a torque about the first axis of rotation $A_1$. This can result in rotation of the second link 4610 relative to the first link 4510 (i.e., pitch), as shown by the arrow OO in FIG. 17A for application of a force via the first tension member 4420 or as shown by arrow NN in FIG. 17B for application of a force via the second tension member 4440. The amount of tension member offset from the longitudinal centerline CL is also based in part on the size of the thimble structure 4660. As shown in FIGS. 16A and 16B, the outer surface 4661 of the thimble structure 4660 contacts the first central portion 4423 of the first tension member 4420 and the third central portion 4433 of the second tension member 4440 when the instrument 4400 is in certain orientations. Thus, the effective radius $R_{bend}$ of the thimble structure 4660 defines the amount of offset.

Figure 13:
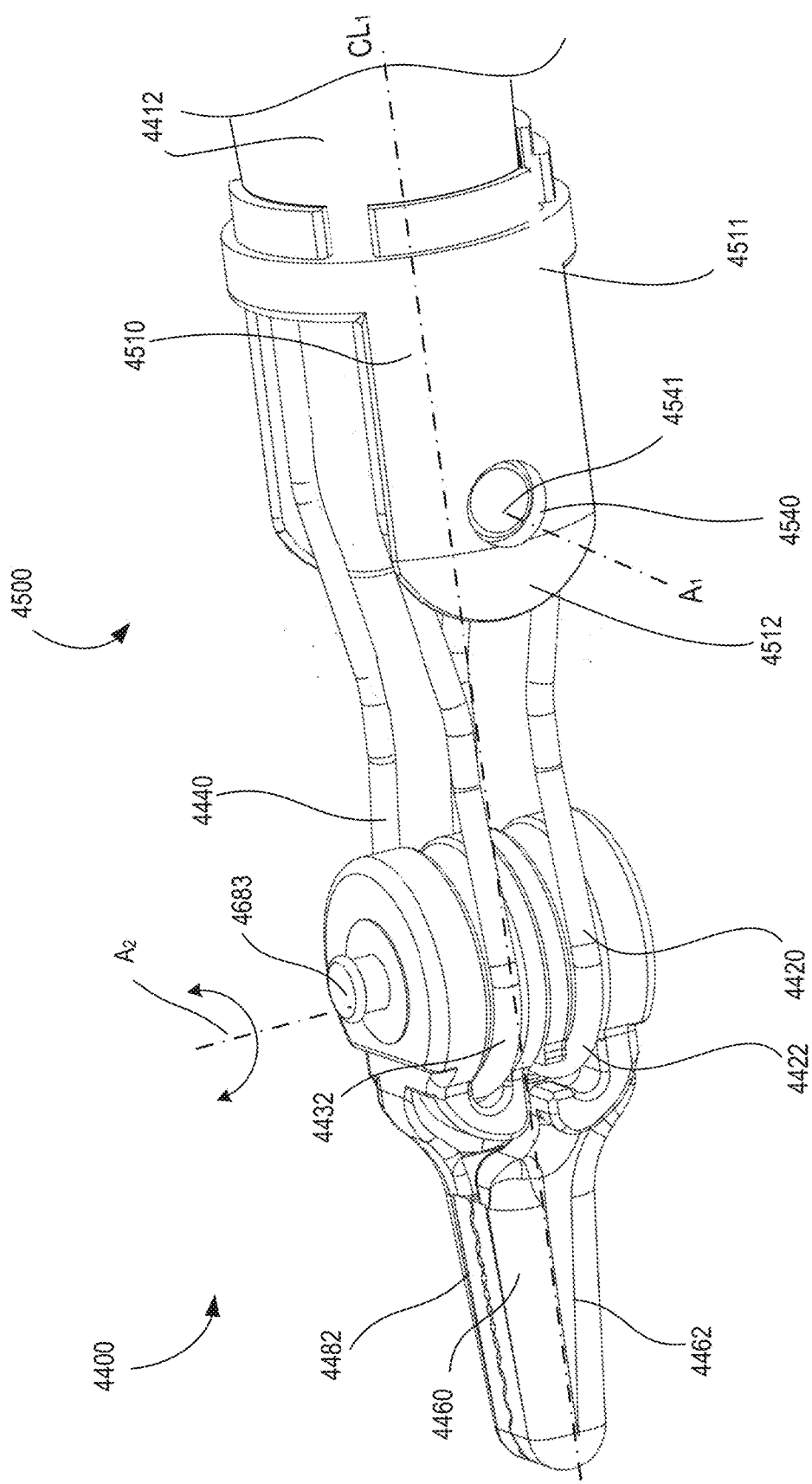
FIG. 13 is a perspective view of the distal end portion of the instrument of FIG. 10 shown with the second link removed to expose portions of the tension members.

As shown in FIG. 13, the end effector 4460 includes a first tool member 4462 and a second tool member 4482. The first tool member 4462 includes a contact portion 4464 and a pulley portion 4467. The contact portion 4464 is configured engage or manipulate a target tissue during a surgical procedure. Although shown as being a gripping surface, in other embodiments the contact portion 4464 can be any suitable surface of the types shown and described herein (e.g., a cutter, a tissue manipulator, a cauterizing surface, or the like). As shown in FIGS. 10 and 11, the pulley portion 4467 is rotatably coupled to the second link 4610 via the pin 4683. In this manner, the first tool member 4462 can rotate about the pin 4683 and relative to the second link 4610 via the second axis of rotation $A_2$. Moreover, the pulley portion 4467 defines the coupling openings 4472 within which the first distal end portion 4422 of the first tension member 4420 is coupled. The outer surface of the pulley portion 4467 is offset from the yaw axis $A_2$. In this manner, application of a force by the first tension member 4420 on the pulley portion 4467 produces a torque on the first tool member 4462 about the yaw axis $A_2$, which can result in rotation of the first tool member 4462 or the application of a gripping force.

As shown in FIG. 13, the second tool member 4482 includes a contact portion 4484 and a pulley portion 4487. The contact portion 4484 is configured engage or manipulate a target tissue during a surgical procedure. Although shown as being a gripping surface, in other embodiments the contact portion 4484 can be any suitable surface of the types shown and described herein (e.g., a cutter, a tissue manipulator, a cauterizing surface, or the like). As shown in FIGS. 10 and 11, the pulley portion 4487 is rotatably coupled to the second link 4610 via the pin 4683. In this manner, the second tool member 4482 can rotate about the pin 4683 and relative to the second link 4610 via the second axis of rotation $A_2$. As shown in FIG. 11, the pulley portion 4487 defines the coupling openings 4472 within which the distal end portion 4432 of the second tension member 4440 is coupled. The outer surface of the pulley portion 4487 is offset from the yaw axis $A_2$. In this manner, application of a force by the second tension member 4440 on the pulley portion 4487 produces a torque on the second tool member 4482 about the yaw axis $A_2$, which can result in rotation of the second tool member 4482 or the application of a gripping force.

Figure 12:
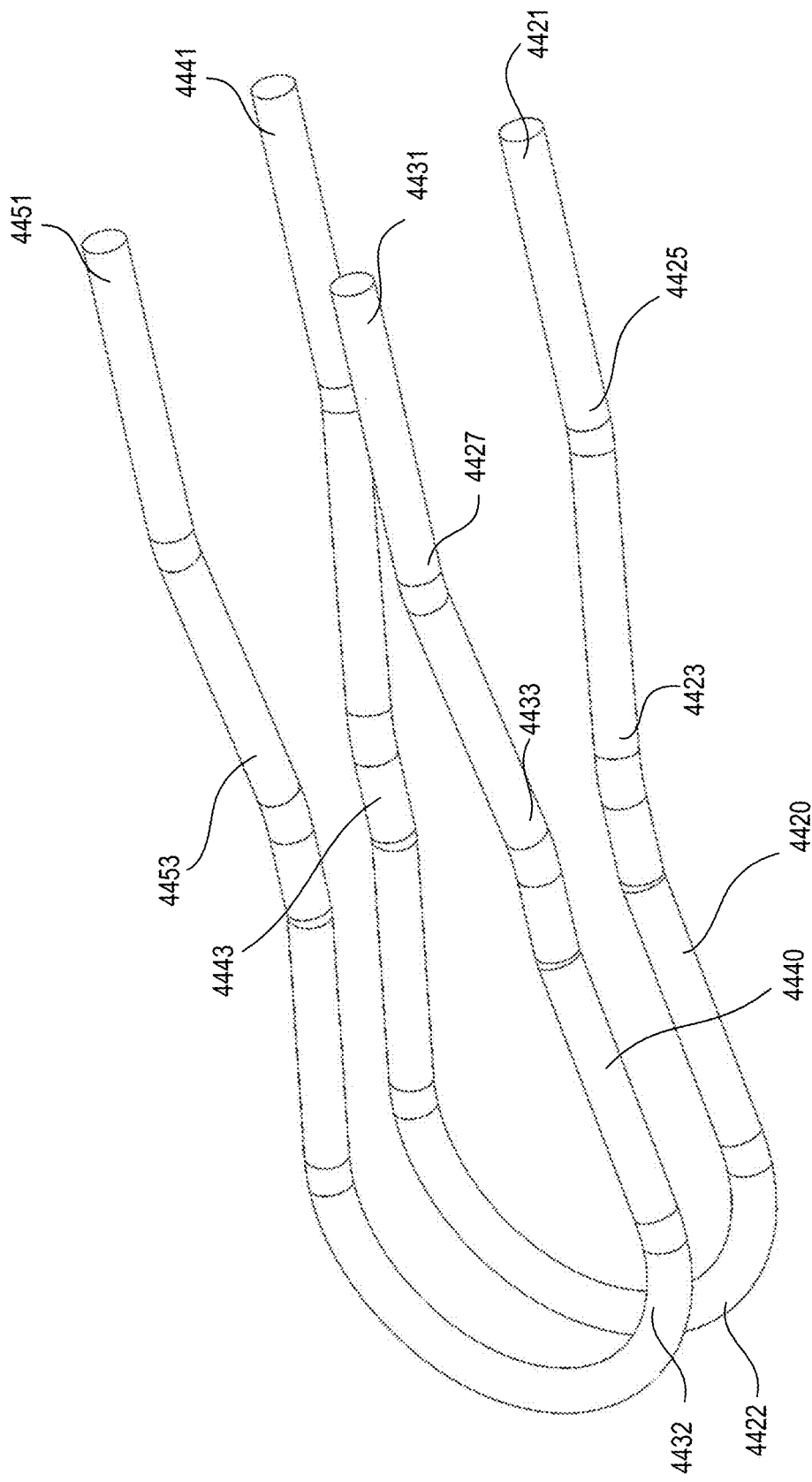
FIG. 12 is an enlarged perspective of portions of the tension members shown in FIG. 11.

As shown in FIG. 12, the first tension member 4420 has a first proximal end portion 4421, a first proximal central portion 4425, a first distal central portion 4423, and a first distal end portion 4422 on one side of a first tension member loop, as well as a second central portion 4443 and a second proximal end portion 4441 along with the first distal end portion 4422 on the other side of the first tension member loop. The second tension member 4440 has a third proximal end portion 4431, a third proximal central portion 4427, a third distal central portion 4433, and a third distal end portion 4432 on one side of a second tension member loop, as well as a fourth central portion 4453 and a fourth proximal end portion 4451 along with the fourth distal end portion on the other side of the second tension member loop. The proximal end portions 4421, 4441, 4431, 4451 each extend outside of the wrist assembly 4500, through the instrument shaft 4410, and into the transmission mechanism 4700. As described above, the transmission mechanism 4700 can move the proximal end portions 4421, 4441, 4431, 4451 to produce a resulting movement (or force) at the respective distal end portions 4422, 4432 of the tension members. The first and second tension members 4420 and 4440 can have any suitable shape. The use of the tension members can provide for a low-cost, disposable instrument that is suitable for minimally-invasive surgical procedures. In use, the distal end portion of the instrument 4400 provides for up to three degrees of freedom, and can be moved between multiple different configurations to perform a variety of surgical operations.

Referring to FIG. 16A, the first proximal central portion 4425 of the first tension member 4420 and the third proximal central portion 4427 of the second tension member 4440 are retained within the first and second curved guide paths 4615, 4620 on one side of the second link 4610, as described above along with FIG. 14B. The shape of the first and second curved guide paths 4615, 4620 are such that the first tension member 4420 and the second tension member 4440 are routed through the wrist assembly 4500 in a manner that maintains the desired bend geometry, tension member tension, and the like therein during actuation of the instrument 4400. This includes routing the first and second tension members 4420, 4440 in a low-friction, parallel-alignment manner with respect to the first and second curved guide paths 4615, 4620 as described below along with FIGS. 16B, 17A and 17B. Similarly, the second central portion 4443 of the first tension member 4420 and the fourth central portion 4453 of the second tension member 4440 are retained within corresponding third and fourth curved guide paths (not shown), as described above for the first and second curved guide paths 4615, 4620. The shape of the third and fourth curved guide paths (not shown) are such that the first tension member 4420 and the second tension member 4440 are routed through the wrist assembly 4500 in a manner that maintains the desired bend geometry, tension member tension, and the like during actuation of the instrument 4400. This likewise includes routing the first and second tension members 4420, 4440 in a low-friction manner as described below along with FIGS. 16B, 17A and 17B for the first and second curved guide paths 4615, 4620. As described above, the first distal end portion 4422 is coupled to the first tool member 4462 and the third distal end portion 4432 is coupled to the second tool member 4482 via a pin or swage coupling (i.e., within the coupling openings 4472, 4472). In this manner, as described herein, movement of (or a force applied to) the tension members can produce pitch, yaw, grip or any combination of these motions.

Referring to FIGS. 16A and 16B, the third guide surface 4617 is formed along a distal portion of the first curved guide path 4615 and is curved inward with respect to the first curved guide path 4615 such that first guide surface 4616 and the third guide surface 4617 are convex with respect to each other and with respect to the first curved guide path 4615. Further, the third guide surface 4617 has an effective radius of curvature $R_1$ that includes the radius of curvature of the third guide surface 4617 plus the thickness (i.e., radius for a circular tension member) of the first tension member 4420. The third guide surface 4617 is configured to guide the first distal central portion 4423 of the first tension member 4420 through the first curved guide path 4615 such that the portion of the first tension member 4420 disposed between the first distal end portion 4422 and first distal central portion 4423 are in parallel alignment with the pulley portion 4467 of the end effector 4460 while in the first orientation shown in FIG. 16A, as well as when in the second orientation shown in FIG. 17A, the third orientation shown in FIG. 17B, and orientations therebetween. As such, the third guide surface can reduce frictional contact between the first tension member 4420 and the end effector 4460 including the pulley portion 4467 during movements of the wrist assembly 4500 by maintaining parallel alignment of the first tension member between the second link 4610 and the end effector 4460. In addition, as discussed further below along with FIG. 17A, the third guide surface is configured to guide the first distal central portion 4423 of the first tension member 4420 while in the second orientation shown in FIG. 17A, such that the first proximal central portion 4425 is retained in parallel alignment with the first guide path 4515 of the first link 4510. The fourth guide surface 4622 is likewise configured to guide portions of the second tension member 4440 in a similar manner with respect to the second guide path 4620.

Figure 17A:
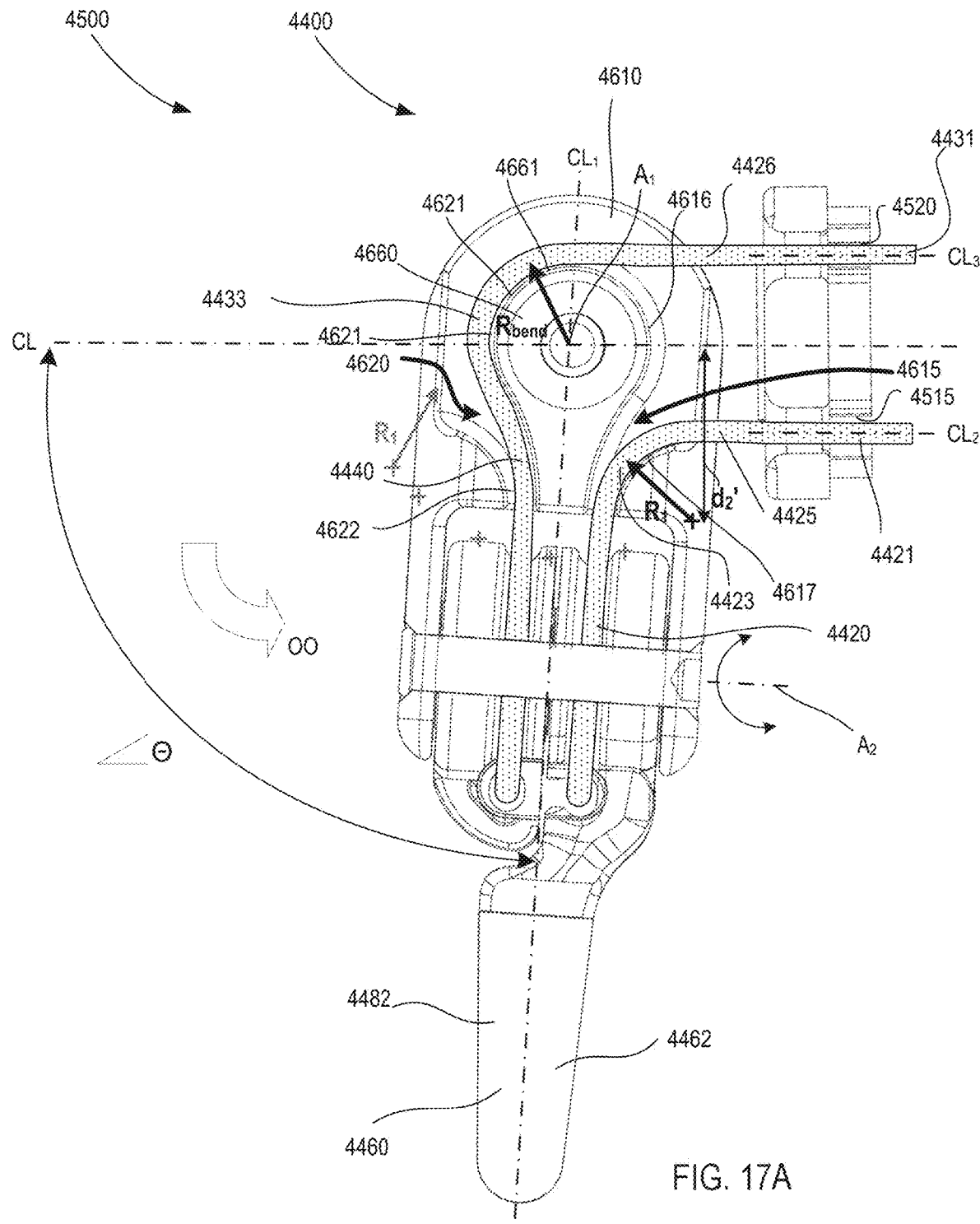
FIG. 17A is a cross-sectional view of the distal end portion of the instrument of FIG. 10 taken along line R-R shown in FIG. 15A, which is shown in a second orientation.
Figure 17B:
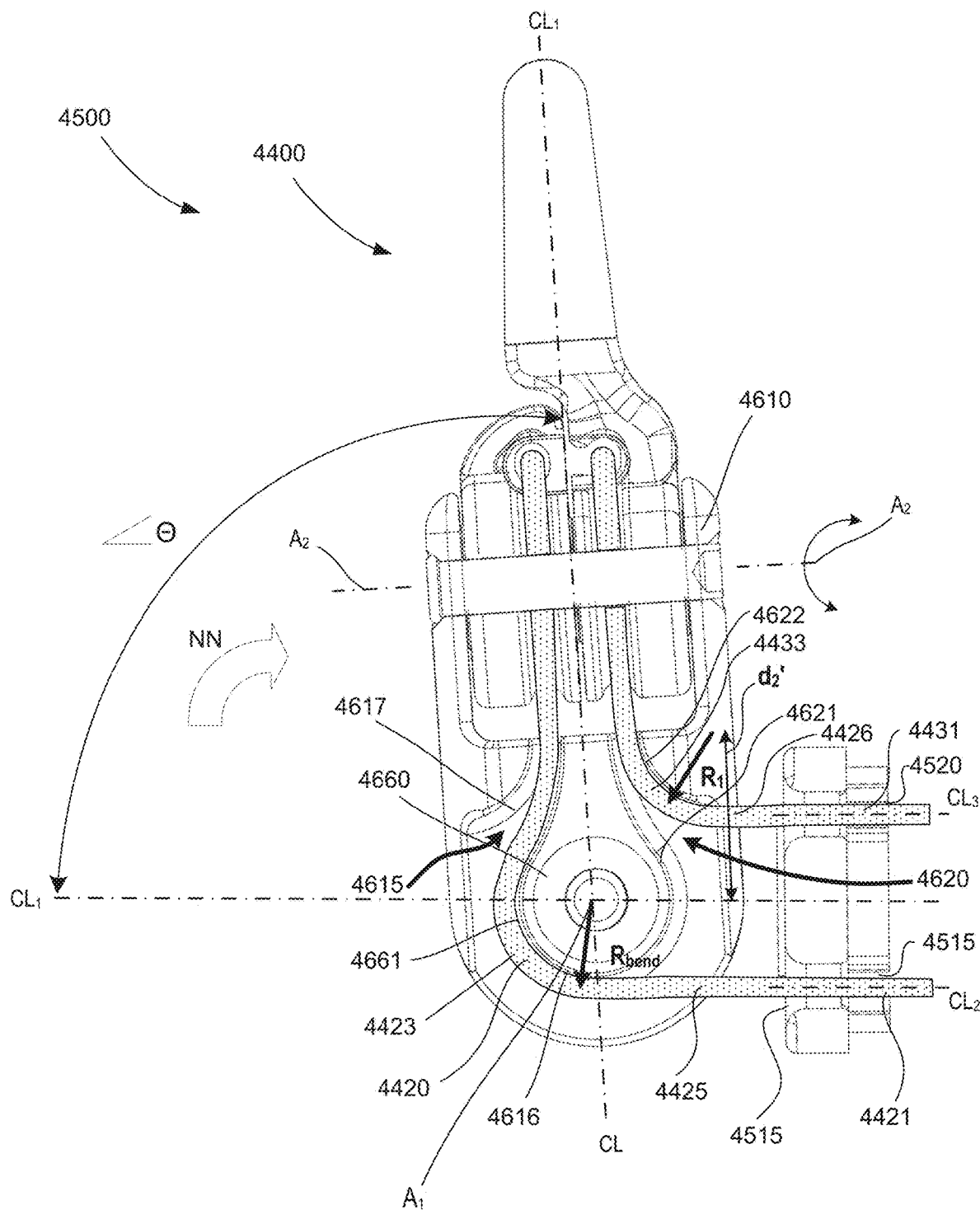
FIG. 17B is a cross-sectional view of the distal end portion of the instrument of FIG. 10 taken along line R-R shown in FIG. 15A, which is shown in a third orientation.

Referring to FIGS. 16A, 16B, and 17B, at least the first guide surface 4616 of the second link 4610 contacts the first distal central portion 4423 of the first tension member 4420 when the second link 4610 is in the first orientation shown in FIGS. 10, 16A and 16B and when the second link 4610 is in other orientations, such as the third orientation shown in FIG. 17B. Similarly stated, the first distal central portion 4423 of the tension member 4420 is in contact with the first guide surface 4616 throughout a portion of the angular range of motion of the second link 4610 relative to the first link 4510. The first guide surface 4616 guides the path of the first tension member 4420 to transition within the second curved guide path 4620 while in the first orientation shown in FIG. 16A and also when the second link 4610 rotates relative to the first link 4510 in direction NN shown in FIG. 17B. Further, the first guide surface 4616 is configured to do so while also maintaining the first proximal central portion 4425 and the first proximal end portion 4421 of the first tension member 4420 in parallel alignment with the centerline $CL_2$ of the first guide path 4515 of the first link 4510.

In particular, the first guide surface 4616 is sized and positioned such that the first proximal end portion 4421, the first proximal central portion 4425, or both the first proximal end portion 4421 and the first proximal central portion 4425 of the first tension member 4420 are retained in parallel alignment with the centerline $CL_2$ of the first guide path 4515 of the first link 4510 throughout a portion of the angular range of motion of the second link 4610 relative to the first link 4510. As such, the first tension member 4420 can move within the first curved guide path 4615 in the directions shown by arrow A-B of FIG. 16A without contacting surfaces within the first guide path 4515 of the first link. In this manner, frictional contact is reduced for movements of the first tension member 4420 for at least the angular range of motion in direction NN. In some embodiments, the first guide surface 4616 has an effective radius of curvature $R_{bend}$ about the first axis of rotation $A_1$ that is equal to the distance $d_1$ shown in FIG. 16A, such that the first proximal end portion 4421, the first proximal central portion 4425, or both the first proximal end portion 4421 and the first proximal central portion 4425 of the first tension member remain parallel to the centerline $CL_2$ over a portion of the range of motion of the second link 4610. Although shown as being a single radius of curvature $R_{bend}$, in other embodiments the first guide surface 4616 can be a curved surface that is characterized by multiple different radii of curvature.

Referring to FIGS. 16A and 17A, at least the second guide surface 4621 of the second link 4610 contacts the third distal central portion 4433 of the second tension member 4440 when the second link 4610 is in the first orientation shown in FIGS. 10 and 16A, as well as when the second link 4610 is in other orientations, such as in the second orientation shown in FIG. 17A. Similarly stated, the third distal central portion 4433 of the second tension member 4440 is in contact with (e.g., wraps around as shown in FIG. 17A) the second guide surface 4621 throughout a portion of the angular range of motion of the second link 4610 relative to the first link 4510. The second guide surface 4621 guides the path of the second tension member 4440 to transition within the second curved guide path 4620 while in the first orientation shown in FIG. 16A, as well as when the second link 4610 rotates relative to the first link 4510 in direction OO shown in FIG. 17A. Further, the second guide surface 4621 is configured to do so while also maintaining the second proximal central portion 4426 and the second proximal end portion 4431 of the second tension member 4440 in parallel alignment with the centerline $CL_3$ of the second guide path 4520 of the first link 4510.

In particular, the second guide surface 4621 is sized and positioned such that the second proximal end portion 4431, the second proximal central portion 4426, or both the second proximal end portion 4431 and the second proximal central portion 4426 of the second tension member 4440 are retained in parallel alignment with the centerline $CL_3$ of the second guide path 4520 throughout a portion of the angular range of motion. As such, the second tension member 4440 can move within the second guide path 4520 of the first link in the directions shown by arrow AB of FIG. 16A without contacting surfaces within the second guide path. In this manner, frictional contact is reduced for movements of the second tension member 4440 for at least the angular range of motion in direction OO. In some embodiments, the second guide surface 4621 has an effective radius of curvature $R_{bend}$ about the first axis of rotation $A_1$ that is equal to the distance $d_1$ shown in FIG. 16A, such that the second proximal end portion 4431, the second proximal central portion 4426, or both the second proximal end portion 4431 and the second proximal central portion 4426 of the second tension member remain parallel to the centerline $CL_3$ over a portion of the range of motion of the second link 4610. Although shown as being a single radius of curvature $R_{bend}$, in other embodiments the second guide surface 4621 can be a curved surface that is characterized by multiple different radii of curvature.

In use, the wrist assembly 4500 can be moved between various orientations. As shown by the arrow OO in FIG. 17A, the wrist assembly 4500 can be moved between a first (or straight) orientation and a second orientation by rotating the second link 4610 relative to the first link 4510 about the first axis of rotation $A_1$. Similarly, the second link 4610 can be rotated in an opposite direction as shown by the arrow NN in FIG. 17B about the first axis of rotation $A_1$ to a third orientation shown in FIG. 17B. When the wrist assembly 4500 is in the first orientation shown in FIG. 16A, the first tension member 4420 is within the first curved guide path 4615 and the second tension member 4440 is within the second curved guide path 4620. More particularly, the first distal central portion 4423 is in contact with the first guide surface 4616 of the second link 4610 and the outer side surface 4661 of the thimble structure 4660. The third distal central portion 4433 is in contact with the second guide surface 4621 of the second link 4610 and the outer side surface 4661 of the thimble structure 4660. When the first tension member 4420 and the second tension member 4440 are moved in the same direction (e.g., to produce a yaw motion of the end effector 4460), the first distal central portion 4423 and the third distal central portion 4433 will slide against the outer side surface 4661, which maintains the first proximal central portion 4425 and the second proximal central portion 4426 of the first and second tension members 4420, 4440 in parallel alignment with the centerlines $CL_2$, $CL_3$ of the first and second guide paths 4515, 4520 of the first link 4510.

When the wrist assembly 4500 is in the second orientation (FIG. 17A), the first distal central portion 4423 of the first tension member 4420 remains within the first curved guide path 4615, but is spaced apart from the first guide surface 4616 and wrapped around and in contact with the third guide surface 4617. Moreover, the first distal central portion 4423 is spaced apart from the thimble structure 4660 and the outer side surface 4661 thereof along with the first guide surface 4616, such that the first distal central portion 4423 is guided within the first curved guide path 4615 primarily by the third curved guide surface 4617.

The third guide surface 4617 has an effective radius of curvature $R_1$ that includes the radius of curvature of the third guide surface 4617 plus half the thickness (i.e., radius for a circular tension member) of the first tension member 4420. The effective radius of curvature $R_1$ is configured to guide the first proximal central portion 4425 of the first tension member 4420 to be in parallel alignment with the centerline $CL_2$ of the first guide path 4515 of the first link 4510 while the wrist assembly 4500 is in the second orientation shown in FIG. 17A. Thus, the first proximal central portion 4425 and the first proximal end portion 4421 of the first tension member 4420 can be maintained in parallel alignment within the first guide path 4515 of the first link 4510 throughout the angular range of motion of the second link 4610 between the second orientation shown in FIG. 17A, through the first orientation shown in FIGS. 16A and 16B as discussed above, and to the third orientation shown in FIG. 17B as discussed below. Thus, frictional contact between the first tension member 4420 within the first guide path 4515 of the first link can be avoided through an angular range of motion of the wrist assembly 4500, which reduces the overall friction for movements thereof.

When the wrist assembly 4500 is in the third orientation (FIG. 17B), the third distal central portion 4433 of the second tension member 4440 remains within the second curved guide path 4620, but is spaced apart from the second guide surface 4621. As such, the third distal central portion 4433 is wrapped around and in contact with the fourth guide surface 4622, which thereby guides the distal central portion to maintain the second proximal central portion 4426 in parallel alignment with the centerline $CL_3$ of the second guide path 4520 of the first link 4510. Moreover, the third distal central portion 4433 is spaced apart from the thimble structure 4660, such that the second distal central portion is guided within the second curved guide path 4620 primarily by the fourth guide surface 4622.

The fourth guide surface 4622 has an effective radius of curvature $R_1$ that includes the radius of curvature of the fourth guide surface 4622 plus half the thickness (i.e., radius for a circular tension member) of the second tension member 4440. The effective radius of curvature $R_1$ is configured to guide the second proximal central portion 4426 of the second tension member 4440 to be in parallel alignment with the centerline $CL_3$ of the second guide path 4520 of the second link 4610 while the wrist assembly 4500 is in the third orientation shown in FIG. 17B. Thus, the second proximal central portion 4426 and the second proximal end 4431 of the second tension member 4440 can be maintained in parallel alignment within the second guide path 4520 of the first link 4510 throughout the angular range of motion of the second link 4610 between the second orientation shown in FIG. 17A, through the first orientation shown in FIGS. 16A and 16B as discussed above, and to the third orientation shown in FIG. 17B. Thus, frictional contact between the second tension member 4440 within the second guide path 4520 of the first link can be avoided through an angular range of motion of the wrist assembly 4500, which reduces the overall friction for movements thereof.

Referring again to FIGS. 16A and 16B, the first tension member 4420 and the second tension member 4440 are configured for low-friction axial movements when the first and second proximal end portions 4421 and 4431 are moved in accordance with the actuator (not shown) as described above, which moves the first proximal end portion in the direction of arrows A-B shown in FIG. 16A. As such, the effective radius, Rh end, of the outer side surface 4661 of the thimble structure 4660 at the proximal end of the thimble structure, which includes the first and second guide surfaces 4616, 4621, is configured to be the same as the distance, $d_1$, that the centerlines, $CL_2$ and $CL_3$, of the first and second guide paths 4515, 4520 of the first link 4510 are offset from the centerline $CL_1$ of the shaft. Stated differently, the effective radius of the first and second guide surfaces, 4616, 4621 (i.e., $R_{bend}$) are configured to be equal to the offset distance (i.e., $d_1$) of the first link guide surfaces 4616, 4621, such that $R_{bend}=d_1$. This relationship maintains the first and second proximal central portions 4425, 4426 and the first and second proximal end portions 4421, 4431 of the first and second tension members 4420, 4440 in parallel alignment within and through the first and second guide paths 4515, 4520 of the first link 4510 while the wrist assembly is in the first orientation shown in FIGS. 16A and 16B.

The relationship of $R_{bend}=d_1$ further maintains this parallel alignment through a portion of the angular rotation for the second link 4610 with respect to the first link 4510 about the first axis of rotation $A_1$ while the first distal central portion 4423 is in contact with the first guide surface 4616 (FIG. 17B), and while the third distal center portion 4433 is in contact with the second guide surface 4621 (FIG. 17A). This is because the first and/or second guide surface 4616, 4621 are formed as portions of the outer side surfaces 4661 of the thimble structure 4660, which have as their effective radius of curvature, $R_{bend}$, that is equal to $d_1$ with respect to the first axis of rotation $A_1$ located along the shaft centerline $CL_1$. As such, the first and/or second proximal central portions 4425, 4426 are retained in parallel alignment with the first and second guide path centerlines $CL_2$ and $CL_3$ in the first link 4510 that are also offset from the shaft centerline by the same distance $d_1$ while in the second orientation (FIG. 17A) and in the third orientation (FIG. 17B). For example, FIG. 17A shows the second tension member 4440 wrapping around a portion of the thimble structure 4660 for the second orientation such that the third distal portion 4433 is in contact with the second guide surface 4621 having an effective radius $R_{bend}$ that is equal to $d_1$ with respect to axis $A_1$ and shaft centerline $CL_1$, which thereby retains the second proximal central portion 4426 in parallel alignment with the second guide path 4520 through the first link 4510. Likewise, FIG. 17B shows the second tension member 4420 wrapping around a portion of the thimble structure 4660 for the third orientation such that the first distal central portion 4423 is in contact with the first surface 4616 having an effective radius $R_{bend}$ that is equal to $d_1$ with respect to axis $A_1$ and shaft centerline $CL_1$, which thereby retains the first proximal central portion 4425 in parallel alignment with the first guide path 4515 through the first link 4510.

With further reference to FIGS. 16A and 16B, the first tension member 4420 and the second tension member 4440 are additionally configured to provide low-friction axial movements while in the first orientation based on: (i) the effective radius of curvature $R_1$, of the third and fourth guide surfaces 4617, 4622; (ii) the effective radius of curvature $R_{bend}$ for the first and second guide surfaces 4616, 4621; and (iii) the perpendicular offset distance of the axis, $A_{R1}$, for $R_1$ from the shaft centerline, $CL_1$. As shown in FIG. 16A, the effective radii of curvature $R_1$, of the third and fourth guide surfaces 4617, 4622 each have an axis, $A_{R1}$, for the radius of curvature that is perpendicularly offset from the shaft centerline, $CL_1$, of the wrist by an offset distance $d_2$ on opposite sides of the shaft centerline. A relationship is provided between the perpendicular offset distance $d_2$, the effective radii of curvatures $R_1$, and the radius of curvature $R_{bend}$, for the first orientation shown in FIG. 16A, such that the perpendicular offset distance $d_2$, is less than the sum of the effective radius of curvature $R_1$ plus the radius of curvature $R_{bend}$, (i.e., $d_2<R_{bend}+R_1$). Such a relationship for the first orientation ensures that the first and third distal central portions 4423, 4433 of the first and second tension members 4420, 4440 are each guided inward toward the centerline CL of the wrist assembly 4500 through guide first and second curved guide paths 4615, 4620, which is concurrent with the shaft centerline $CL_1$ in the first orientation shown in FIG. 16A. The first and third distal central portions 4423, 4433 are guided inward within the corresponding first or second curved guide paths 4615, 4620 from a point of contact with the first or second guide surface 4616, 4621 to a point of contact with the corresponding third or fourth guide surface 4617, 4622. As such, each of the first and third distal central portions 4423, 4433 is biased into contact with the corresponding first or second guide surface 4616, 4621 and with the corresponding third or fourth guide surface 4617, 4622 for the respective first or second curved guide paths 4615, 4620 while in the first orientation, which aligns the first and second proximal central portions 4425, 4426 in parallel alignment with the corresponding first and second first guide paths 4515, 4420 of the first link 4510.

As shown in FIG. 16A, the second link 4610 is configured to rotate with respect to the first link 4510 about the first axis of rotation, $A_1$. The second link 4610 rotates in the indicated direction OO for angular rotation $\Theta$ to rotate from the first orientation to the second orientation shown in FIG. 17A. In some embodiments, the angular rotation, $\Theta$, from the first to the second orientation can be a maximum angular rotation $\Theta$ for the second link 4610 with respect to the first link 4510. As the second link 4610 rotates from the first orientation to the second orientation, the third and fourth guide surfaces 4617, 4622, the corresponding effective radii of curvature, $R_1$, and the curvature axis, $A_{R1}$, also rotate by angular rotation $\Theta$ about the first axis, $A_1$. The rotation changes the location of the curvature axis, $A_{R1}$, for the third guide surface 4617 and its perpendicular offset distance, $d_2$, from the shaft centerline CL in the first orientation to a rotated position for the second orientation as shown in FIG. 17A, which is offset by a perpendicular distance $d_2'$ from the shaft centerline CL.

In embodiments in which the second link 4610 is rotated at a maximum angular rotation, $\Theta$, for the second orientation, the perpendicular offset distance $d_2'$ from the shaft centerline CL to the axis, $A_{R1}$, for the third guide surface 4617 is equal to the shaft offset distance $d_1$ of the centerline $CL_2$ of the first guide path 4515 in the first link 4510 plus the corresponding radius of curvature, $R_1$, of the third guide surface 4617. Stated differently, $d_2'$ (curvature axis perpendicular offset at maximum rotation) is equal to the sum of $d_1$ (first guide path perpendicular offset) and $R_1$ (radius of distal third guide surface) (i.e., $d_2'=d_1+R_1$), which maintains parallel alignment of the first proximal central portion 4425 with the first guide path 4515 at maximum angular rotation in direction OO. Whereas, for the first orientation of FIG. 16A, $d_2$ (curvature axis perpendicular offset in first orientation), is less than the sum of $d_1$ and $R_1$ (i.e., $d_2<d_1+R_1$), which maintains parallel alignment of the first proximal central portion 4425 with the first guide path 4515 at that orientation. This is due to the first distal central portion 4423 of the first tension member 4420 being retained against the third guide surface 4617 in the second orientation at the maximum angular rotation, $\Theta$, such that the first proximal central portion 4425 and the first proximal end portion 4421 are in parallel alignment with the first guide path 4515. Thus, the first tension member 4420 can move freely in the longitudinal direction within the first guide path 4515 in the second orientation at its maximum angular rotation without frictional contact with surfaces within the first guide path.

Referring to FIGS. 14B and 16B, the thimble structure 4660 includes a proximal region 4663 and a distal region 4664. The outer side surface 4661 of the proximal region 4663 includes the first guide surface 4616 on one side of the centerline CL of the shaft and the second guide surface 4621 on the opposite second side of the centerline. In addition, the proximal region 4663 is curved according to the radius of curvature $R_{bend}$ about the axis of rotation $A_1$. In contrast, the outer side surface 4661 within the distal region 4664 is not curved according the radius of curvature $R_{bend}$. Rather, the outer side surface 4661 within the distal region 4664 is configured to have a contour that generally follows the contour of the portions of the first and second tension members 4420, 4440 proximate to the outer side wall therein while in the first orientation shown in FIG. 16B. Such contour portions of the outer side surface 4661 can provide additional guide surfaces along the first and second curved guide paths 4615 and 4620 for guiding the first and second tension members 4420, 4440 during movements within the guide paths.

In some embodiments, the thimble structure can be configured to include the proximal region 4663 of the thimble structure 4660 without including the distal region 4664. As such, the thimble structure 4660 shown in FIGS. 14B and 16B can be configured to include the portions of the outer side surface 4661 that form the first guide surface 4616 and the second guide surface 4621, which are curved to have the radius of curvature $R_{bend}$, without including remaining portions of the outer side surface 4661 that are not curved according to the radius of curvature $R_{bend}$ (and corresponding portions of the thimble structure 4660). In other words, the thimble structure can be configured to have a round pulley-like shape, which can be fixed with respect to the second link 4610 or mounted as a pulley for rotation with respect to the second link 4610. Such embodiments can further avoid potential frictional contact between the first and second tension members 4420, 4440 and surfaces disposed along the first and second curved guide paths 4615, 4620 from distal portions of the thimble during longitudinal movements of the tension members therein. For example, FIGS. 18-25 show various views of an instrument 5400, according to an embodiment, in which the thimble structure is configured as a pulley that lacks a distal portion and corresponding surfaces, and that rotates relative to the second link 5610. The instrument 5400 generally includes the aspects and features of instrument 4400 discussed above along with FIGS. 10-17B, except as discussed below along with FIGS. 18-25.

Figure 18:
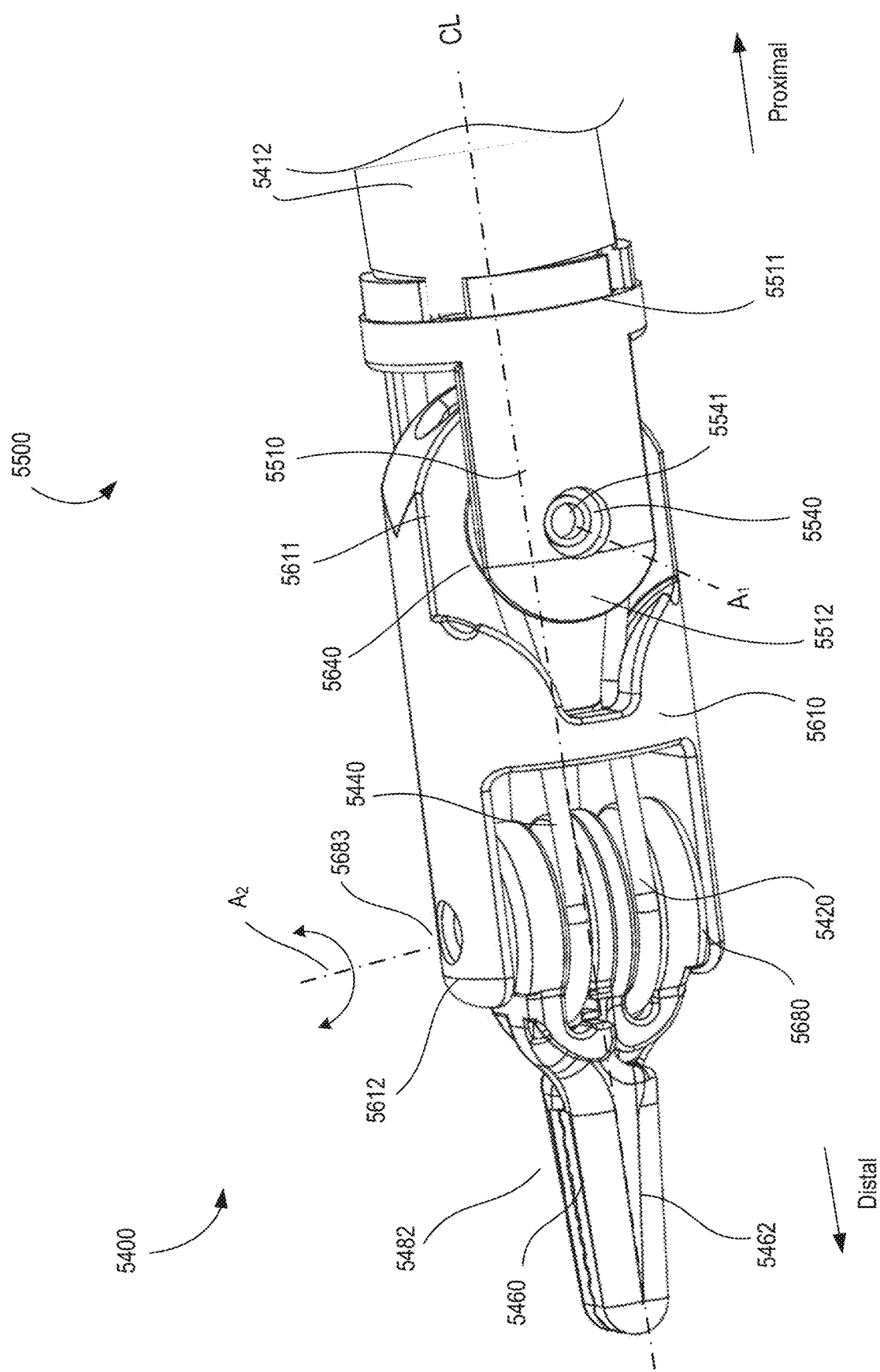
FIG. 18 is an enlarged perspective view of a distal end portion of another instrument indicated by the region Z shown in FIG. 9, according to an embodiment.

Similar to instrument 4400, the instrument 5400 includes a transmission mechanism (that can function as an actuator mechanism), an instrument shaft 5410, a wrist assembly 5500, and an end effector 5460. Referring to FIG. 18, the instrument 5400 also includes a first tension member 5420 and a second tension member 5440 that couple the transmission mechanism to the wrist assembly 5500. The instrument 5400 is configured such that movement of the cables can produce rotation of the wrist assembly 5500 (i.e., pitch rotation) about a first axis of rotation $A_1$, yaw rotation of the end effector 5460 about a second axis of rotation $A_2$, grip rotation of the tool members of the end effector 5460 about the yaw axis, or any combination of these movements. Changing the pitch, yaw, or grip of the instrument 5400 can be performed by manipulating the four cables in similar manner as that described above for the instruments 3400 and 4400. Thus, the specific movement of each of the four cables to accomplish the desired motion is not described below. Although shown and described as including two cables that are wrapped about the end effector 5460 resulting in four proximal end cable portions (i.e., the four-cable arrangement), in other embodiments the instrument 5400 can include additional cables that separately change the pitch of the instrument 5400.

Figure 19:
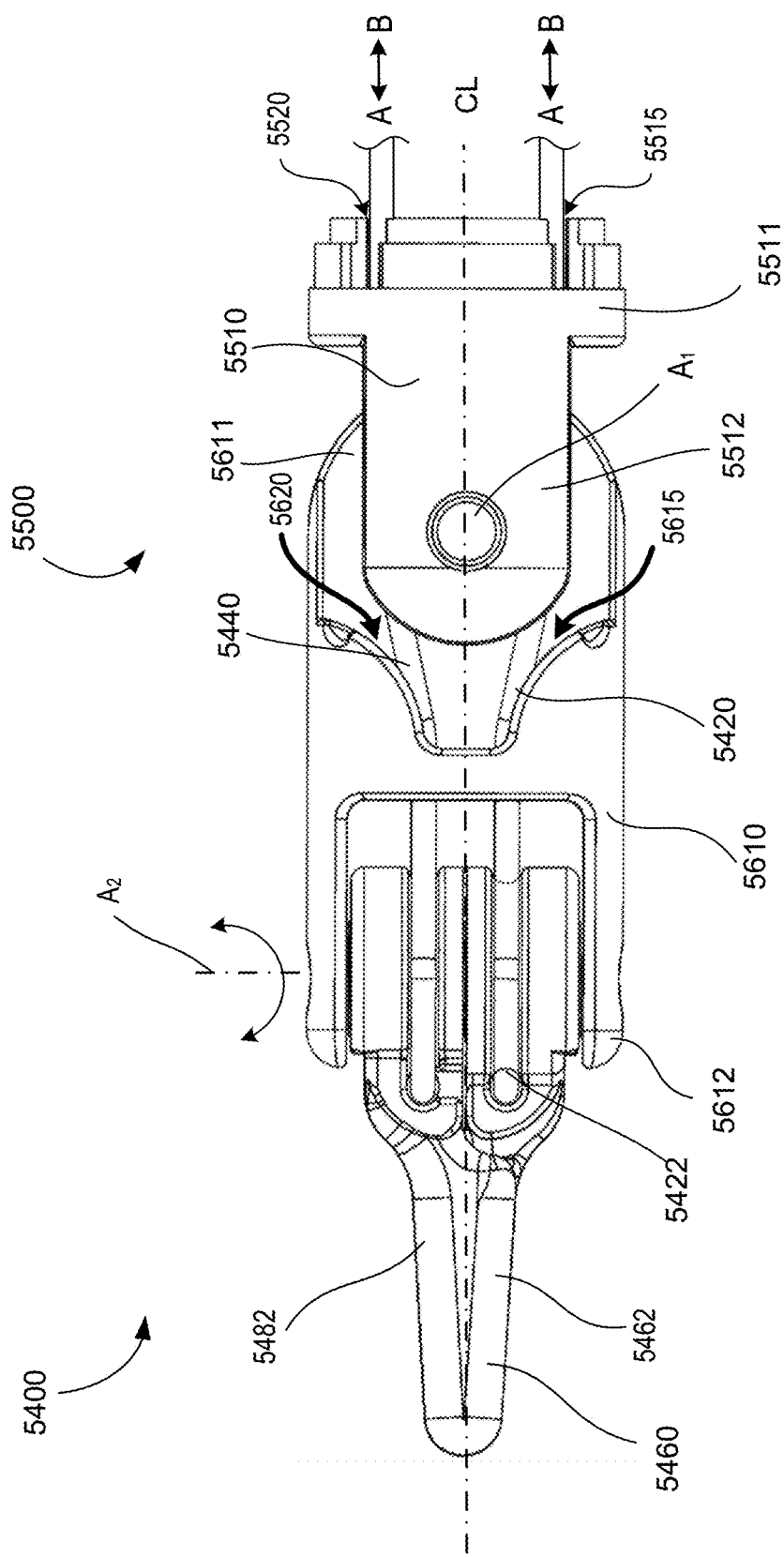
FIG. 19 is a side view of the distal end portion of the instrument of FIG. 18 in a first orientation, taken along line Y-Y shown in FIG. 9.

Referring to FIGS. 18 and 19, the wrist assembly 5500 includes a first link 5510 and a second link 5610. The first link 5510 has a proximal end portion 5511 and a distal end portion 5512. The proximal end portion 5511 is coupled to the distal end portion 5412 of the instrument shaft 5410. The proximal end portion 5511 can be coupled to the instrument shaft 5410 via any suitable mechanism. For example, in some embodiments, the proximal end portion 5511 can be matingly disposed within a portion of the instrument shaft (e.g., via an interference fit). As shown, the proximal end portion 5511 can include one or more protrusions, recesses, openings, or connectors that couple the proximal end portion 5511 to the instrument shaft. The proximal end portion 5511 can be fixedly coupled to the instrument shaft 5410 via an adhesive bond, a weld, or any other permanent coupling mechanism (i.e., a coupling mechanism that is not intended to be removed during normal use).

The distal end portion 5512 includes a joint portion 5540 that is rotatably coupled to a mating joint portion 5640 of the second link 5610. In this manner, the first link 5510 and the second link 5610 form the wrist assembly 5500 having a first axis of rotation $A_1$ (also referred to as the pitch axis) about which the second link 5610 can rotate relative to the first link 5510. A pin 5541 extends through joint portion 5540 of the distal end 5512 and the joint portion 5640 of the second link 5610 to rotatably couple the second link 5610 to the first link 5510. As shown in FIG. 18, the first link 5510 and the second link 5610 define a longitudinal centerline CL that intersects the pitch axis $A_1$ when the instrument is in an initial (or "straight" configuration).

The second link 5610 has a proximal end portion 5611 and a distal end portion 5612. As described above, the proximal end portion 5611 includes a joint portion 5640 that is rotatably coupled to the joint portion 5540 of the first link 5510. The distal end portion 5612 of the second link 5610 includes a connector 5680 that is coupled to the end effector 5460. In this manner, the first tool member 5462 and the second tool member 5482 can rotate relative to the second link 5610 about a second axis of rotation (also referred to as the yaw axis) $A_2$. The connector 5680 is a pin-type connector and includes the pin 5683 which is supported by (and placed within) the pin openings. In some embodiments, the connector 5680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIG. 10, the second axis of rotation $A_2$ (also referred to as the yaw axis) is non-parallel to the pitch axis $A_1$. Thus, the instrument 5400 provides for up to three degrees of freedom (i.e., a pitch motion about the first axis of rotation $A_1$, a yaw rotation about the second axis of rotation $A_2$, and a grip motion about the second axis of rotation $A_2$).

Figure 20:
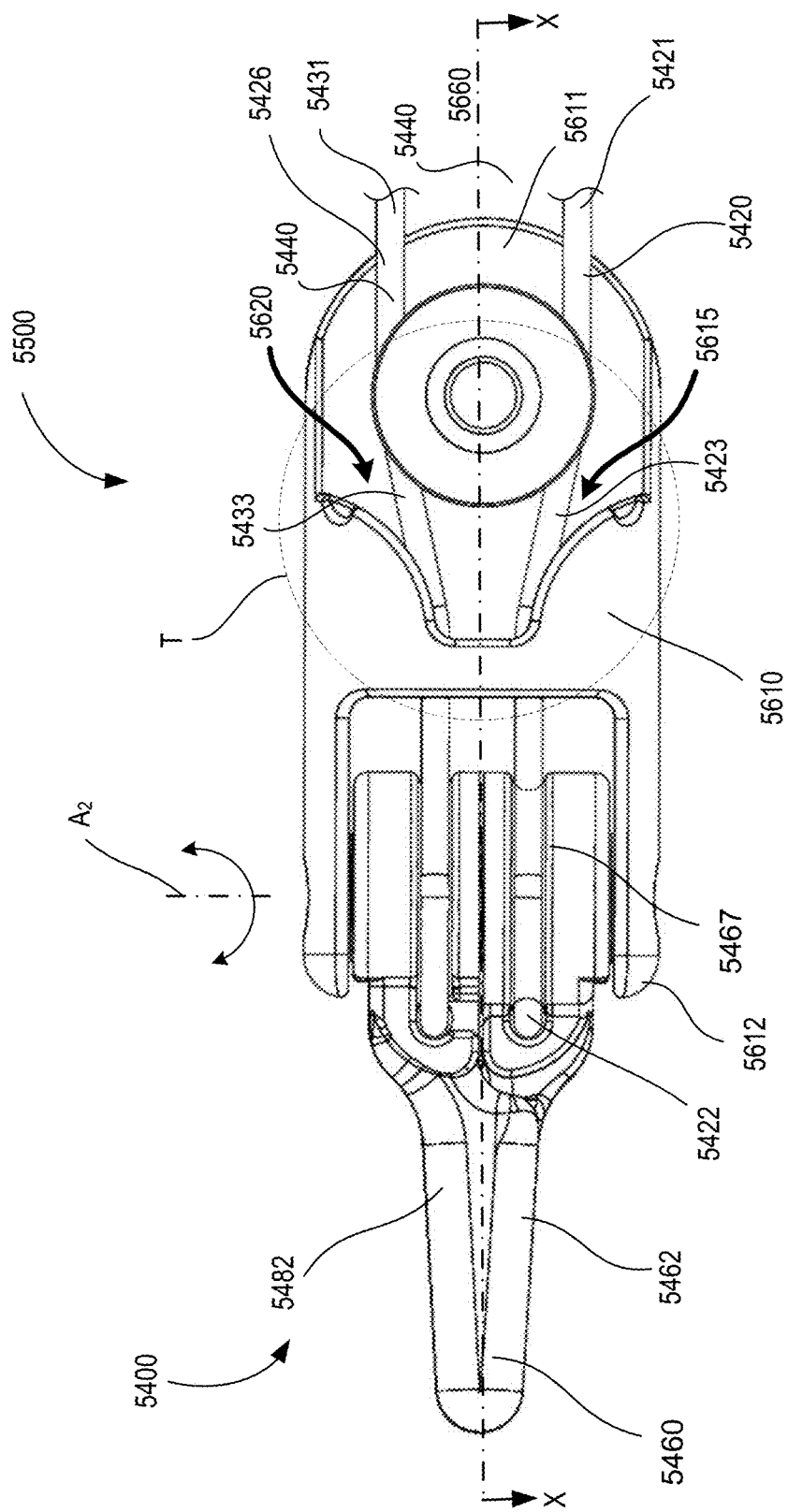
FIG. 20 is a side view of the distal end portion of the instrument of FIG. 18 in a first orientation and shown with the first link removed to expose portions of the tension members.
Figure 23:
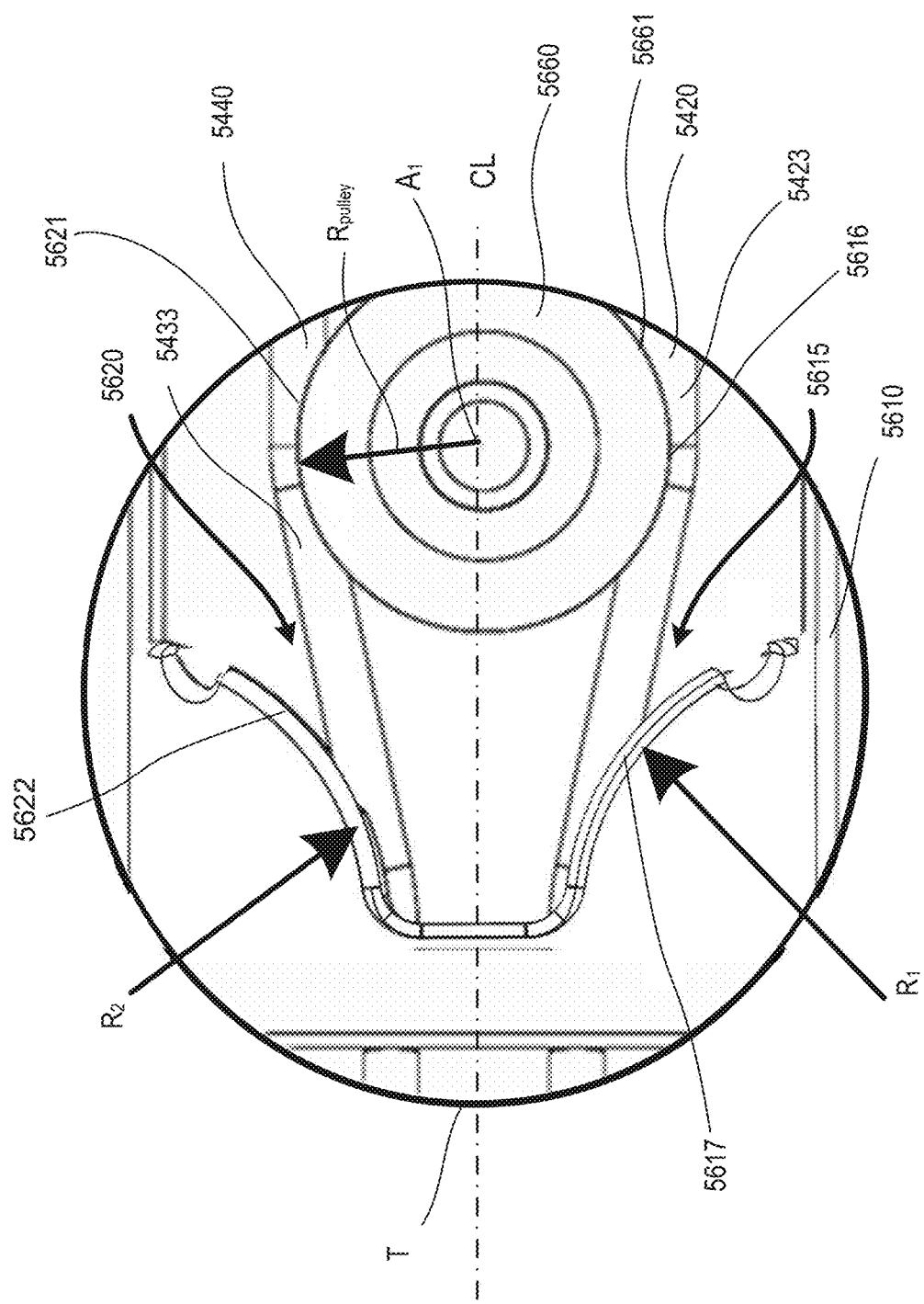
FIG. 23 is an enlarged side view of a distal end portion of the instrument of FIG. 18 in the first orientation indicated by the region T shown in FIG. 20.
Figure 24:
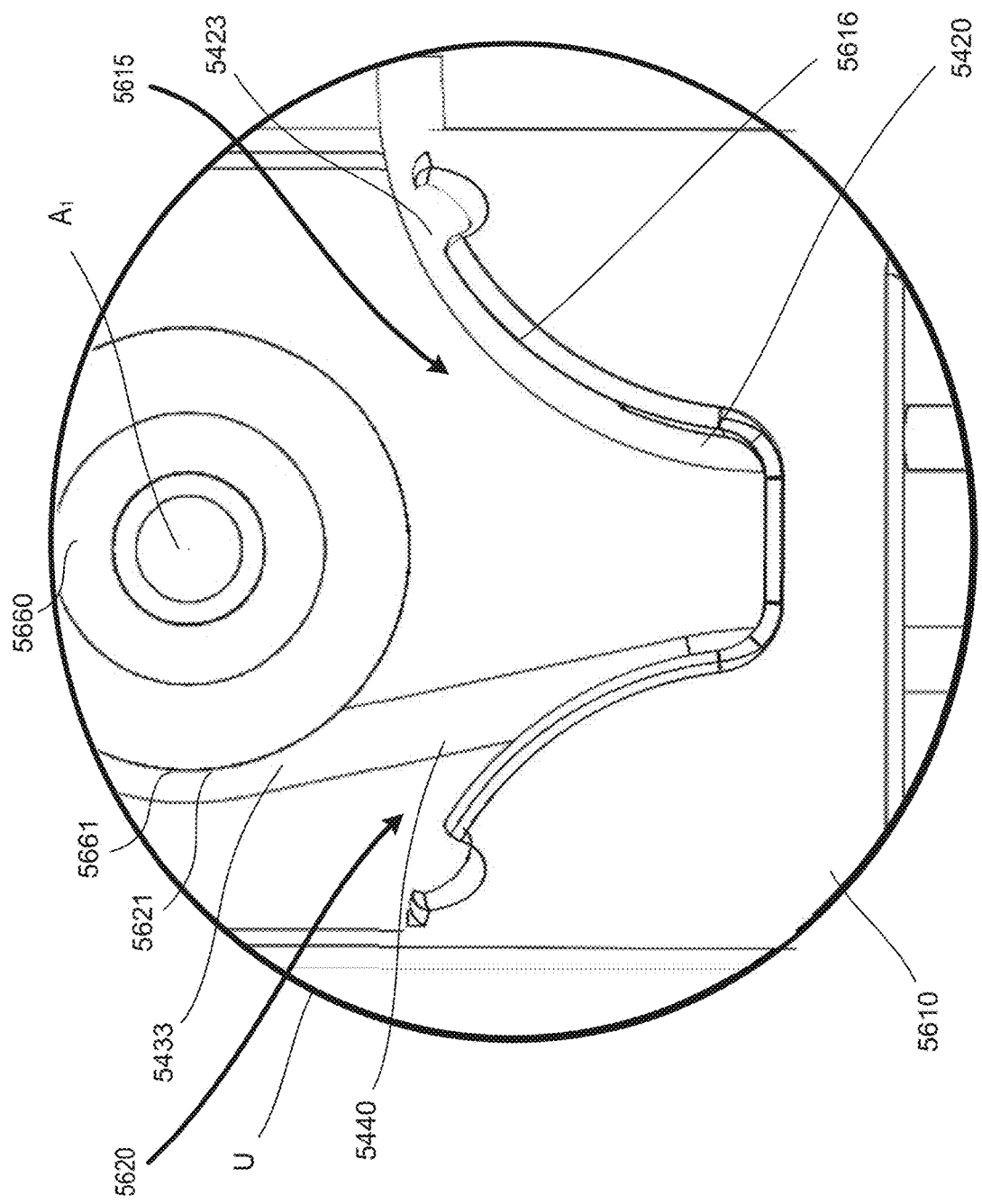
FIG. 24 is an enlarged side view of a distal end portion of the instrument of FIG. 18 in the second orientation indicated by the region U shown in FIG. 21.
Figure 25:
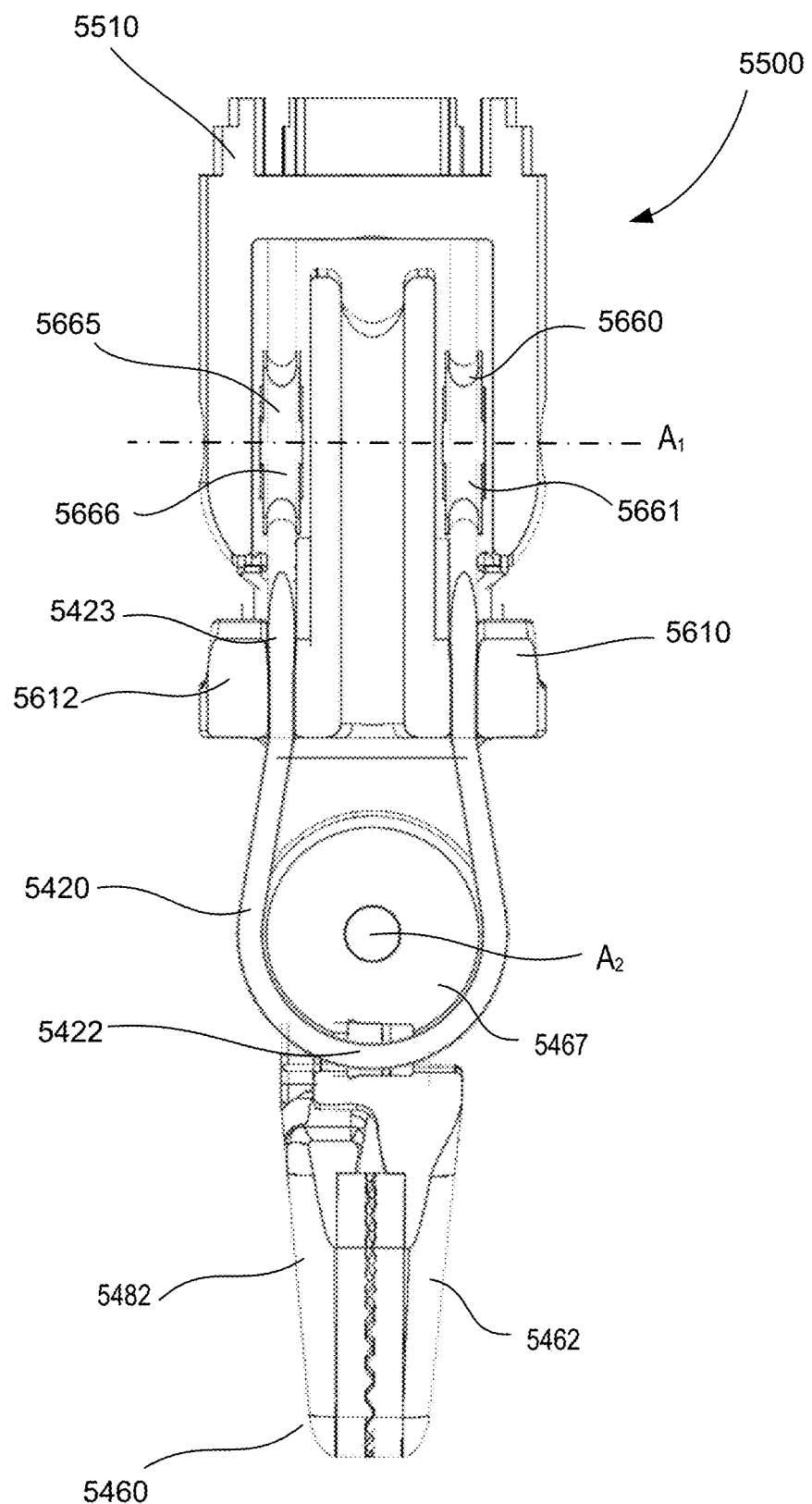
FIG. 25 is a cross-sectional view of the distal end portion of the instrument of FIG. 18 in a first orientation, taken along line X-X shown in FIG. 20.

Referring to FIGS. 20, 23 and 25, the second link 5610 includes a first pulley 5660 (which functions as a first thimble member), and a second pulley 5665 (which functions as a second thimble member). The first pulley 5660 and the second pulley 5665 are each rotatably coupled to the second link 5610 via the pin 5541. In this manner, the first pulley 5660 and the second pulley 5665 can each rotate relative to the second link 5610 about the first axis of rotation $A_1$. In other embodiments (not shown), the first pulley 5660 and the second pulley 5665 can be fixedly attached to the second link 5610. The first pulley 5660 includes an outer surface 5661 within a grooved channel (see FIG. 25), and the second pulley 5665 includes an outer surface 5666 within a grooved channel (see FIG. 25). This arrangement allows the first distal central portion 5423 of the first tension member 5420 and second distal central portion 5433 of the second tension member 5440 to each contact the outer surface 5661 of the first pulley (see FIGS. 23 and 24), depending on the orientation of the wrist assembly 5500. Although not shown, the third central portion of the first tension member 5420 and the fourth central portion of the second tension member 5440 can similarly contact the outer surface 5666 of the second pulley 5665. Thus, this arrangement provides one pulley that functions to engage and define a portion of a guide path for two distinct cable portions. As shown in FIG. 23, the radius of the first pulley 5660 and the second pulley 5665 is identified as $R_{pulley}$, and is selected to produce the desired guide path, as described below.

As shown in FIG. 23, the second link 5610 defines a first curved guide path 5615 and a second curved guide path 5620. The second link 5610 also includes a first guide surface 5616 and a third guide surface 5617 that are aligned with a portion of the first curved guide path 5615. The second link 5610 also includes a second guide surface 5621 and a fourth guide surface 5622 that are aligned with a portion of the second curved guide path 5620. The first and second curved guide paths 5615, 5620 (and therefore the portions of the first tension member 5420 and the second tension member 5440 therein) are each offset from the longitudinal centerline CL and the first axis of rotation $A_1$. In this manner, application of a force via the first tension member 5420 or the second tension member 5440 produces a torque about the first axis of rotation $A_1$. This can result in rotation of the second link 5610 relative to the first link 5510 (i.e., pitch), as shown by the arrow OO in FIG. 22 for application of a force via the first tension member 5420. The amount of tension member offset from the longitudinal centerline CL is also based in part on the size of the pulley 5660. As shown in FIG. 23, the outer surface 5661 of the pulley 5660 contacts the first distal central portion 5423 of the first tension member 5420 and the second distal central portion 5433 of the second tension member 5440 when the instrument 5400 is in certain orientations. Thus, the radius $R_{pulley}$ of the pulley 5660 defines the amount of offset.

In use, the wrist assembly 5500 can be moved between various orientations. As shown by the arrow OO in FIG. 22, the wrist assembly 5500 can be moved between a first (or straight) orientation and a second orientation by rotating the second link 5610 relative to the first link 5510 about the first axis of rotation $A_1$. Similarly, the second link 5610 can be rotated in an opposite direction about the first axis of rotation $A_1$ to a third orientation (not shown). When the wrist assembly 5500 is in the first orientation, the first tension member 5420 is within the first curved guide path 5615 (e.g., a first tension member path) and the second tension member 5440 is within the second curved guide path 5620 (e.g., a second tension member path). More particularly, the first distal central portion 5423 is in contact with the first guide surface 5616 of the second link 5610 and the outer surface 5661 of the pulley 5660. The second distal central portion 5433 is in contact with the third guide surface 5617 of the second link 5610 and the outer surface 5661 of the pulley 5660.

As discussed above along with wrist assembly 4500 and as shown in FIGS. 19, 20 and 23, the first and second tension members 5420, 5440 are routed through the first and second curved guide paths 5615, 5620 in a low-friction, parallel-alignment manner with respect to the first and second guide paths 5515, 5520 in the first link 5510. Similarly, the second central portion of the first tension member 5420 and the fourth central portion of the second tension member 5440 are retained within corresponding third and fourth curved guide paths (not shown), as described herein for the first and second curved guide paths 5615, 5620. The shape of the third and fourth curved guide paths (not shown) are such that the first tension member 5420 and the second tension member 5440 are routed through the wrist assembly 5500 in a manner that maintains the desired bend geometry, tension member tension, and the like during actuation of the instrument 5400. This likewise includes routing the first and second tension members 5420, 5440 in a similar parallel, low-friction manner.

Referring to FIGS. 20 and 23, the third guide surface 5617 is formed along a distal portion of the first curved guide path 5615 and is curved inward with respect to the first curved guide path 5615 such that first guide surface 5616 and the third guide surface 5617 are convex with respect to each other and with respect to the first curved guide path 5615. Further, the third guide surface 5617 has an effective radius of curvature $R_1$ that includes the radius of curvature of the third guide surface 5617 plus the thickness (i.e., radius for a circular tension member) of the first tension member 5420. The third guide surface 5617 is configured to guide the first distal central portion 5423 of the first tension member 5420 through the first curved guide path 5615 such that the portion of the first tension member 5420 disposed between the first distal end portion 5422 and first distal central portion 5423 are in parallel alignment with the pulley portion 5467 of the end effector 5460 while in the first orientation shown in FIGS. 20 and 23, as well as when in the second orientation shown in FIGS. 21 and 24, in a third orientation rotated opposite from the second orientation (not shown), and in orientations therebetween. As such, the third guide surface 5617 can reduce frictional contact between the first tension member 5420 and the end effector 5460 including the pulley portion 5467 during movements of the wrist assembly 5500 by maintaining parallel alignment of the first tension member between the second link 5610 and the end effector 5460.

Figure 21:
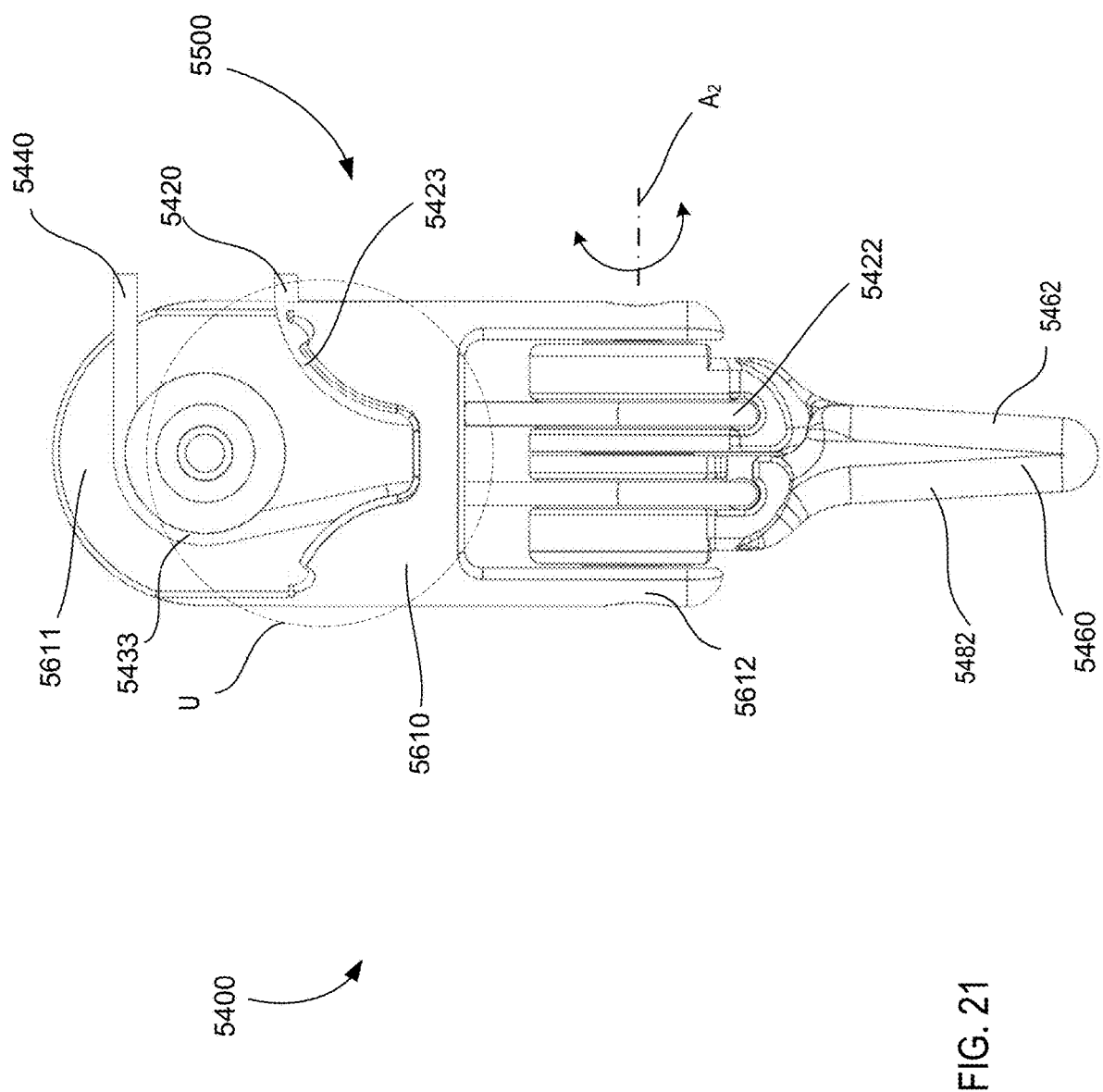
FIG. 21 is a side view of the distal end portion of the instrument of FIG. 18 in a second orientation and shown with the first link removed to expose portions of the tension members.
Figure 22:
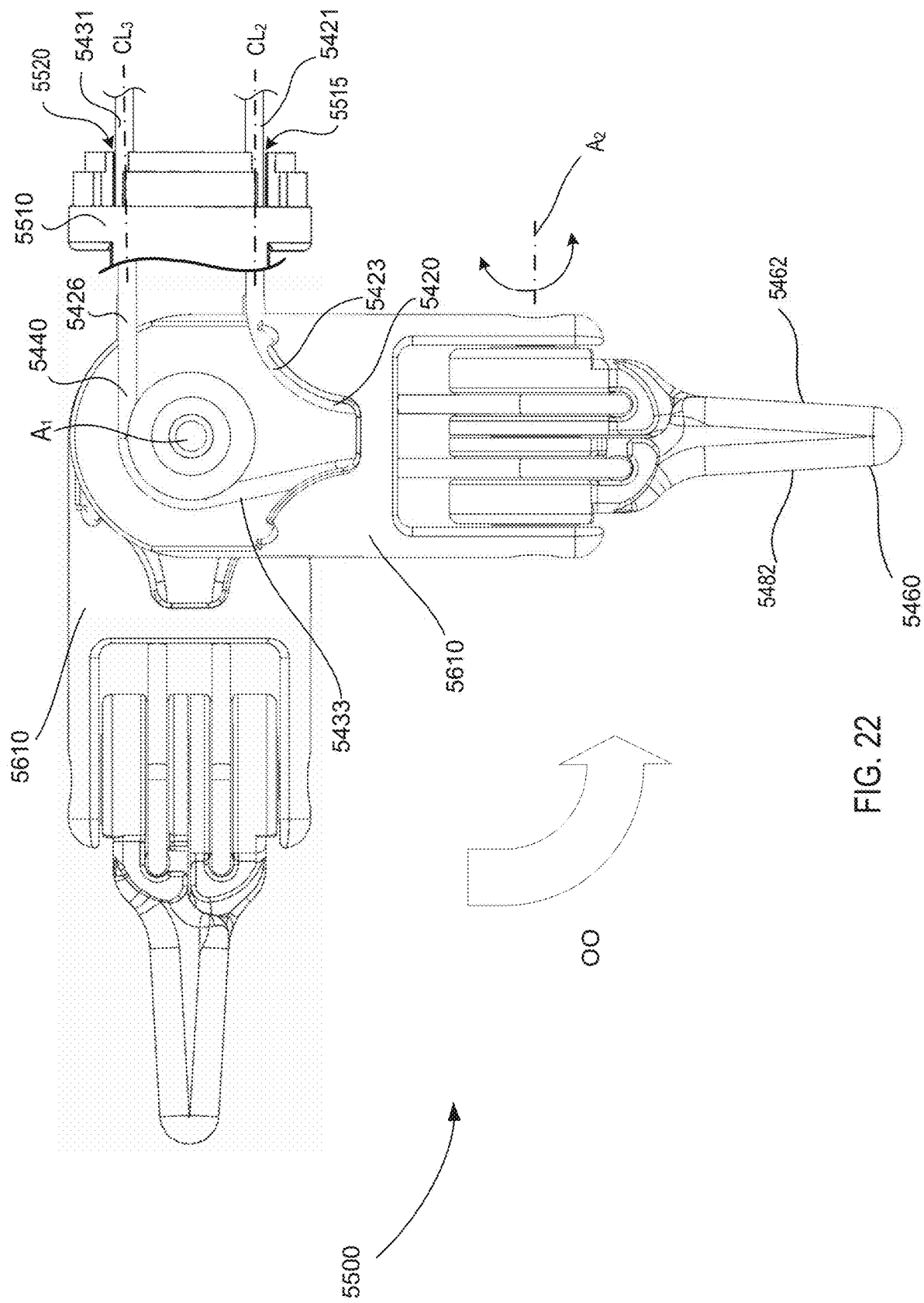
FIG. 22 is a side view of the distal end portion of the instrument of FIG. 18 showing the second orientation of FIG. 21 superimposed over the first orientation of FIG. 20, and both shown with the first link removed to expose portions of the tension members.

Referring to FIGS. 19, 20 and 23, at least the second guide surface 5621 of the second link 5610 contacts the second distal central portion 5433 of the second tension member 5440 when the second link 5610 is in the first orientation shown in FIGS. 19, 20 and 23, as well as when the second link 5610 is in other orientations, such as in the second orientation shown in FIGS. 21 and 24. Similarly stated, the second distal central portion 5433 of the second tension member 5440 is in contact with (e.g., wraps around as shown in FIGS. 21, 22 and 24) the second guide surface 5621 throughout a portion of the angular range of motion of the second link 5610 relative to the first link 5510. The second guide surface 5621 guides the path of the second tension member 5440 to transition within the second curved guide path 5620 while in the first orientation shown in FIGS. 19, 20 and 23, as well as when the second link 5610 rotates relative to the first link 5510 in direction OO shown in FIG. 22. Further, the second guide surface 5621 is configured to do so while also maintaining the second proximal central portion 5426 and the second proximal end portion 5431 of the second tension member 5440 in parallel alignment with the centerline $CL_3$ of the second guide path 5520 of the first link 5510.

In particular, the second guide surface 5621 is sized and positioned such that the second proximal end portion 5431, the second proximal central portion 5426, or both the second proximal end portion 5431 and the second proximal central portion 5426 of the second tension member 5440 are retained in parallel alignment with the centerline $CL_3$ of the second guide path 5520 throughout a portion of the angular range of motion. As such, the second tension member 5440 can move within the second guide path 5520 of the first link in the directions shown by arrow A-B of FIG. 19 without contacting surfaces within the second guide path. In this manner, frictional contact is reduced for movements of the second tension member 5440 for at least the angular range of motion in direction OO. In some embodiments, the second guide surface 5621 has an effective radius of curvature $R_{bend}$ about the first axis of rotation $A_1$ that is equal to the distance $d_1$ shown in FIG. 16A, such that the second proximal end portion 5431, the second proximal central portion 5426, or both the second proximal end portion 5431 and the second proximal central portion 5426 of the second tension member remain parallel to the centerline $CL_3$ over a portion of the range of motion of the second link 5610. Although shown as being a single radius of curvature $R_{bend}$, in other embodiments the second guide surface 5621 can be a curved surface that is characterized by multiple different radii of curvature.

When the first tension member 5420 and the second tension member 5440 are moved in the same direction (e.g., to produce a yaw motion of the end effector 5460), one of the first distal central portion 5423 or the second distal central portion 5433 will move along with rotation of the pulley 5660, and the other of the first distal central portion 5423 or the second distal central portion 5433 will slide against the outer surface 5661. Typically, the tension member that has the greater wrap angle about the pulley 5660 (i.e., the tension member that has the greater amount of friction with the outer surface 5661) will cause the pulley 5660 to rotate, and the tension member with the lesser wrap angle (i.e., the tension member that has the lower amount of friction) will slide against the outer surface 5661. In this manner, the pulley 5660 advantageously reduces the friction at the area of highest friction. This arrangement allows for efficient operation of the end effector 5460 regardless of the pitch orientation of the wrist assembly 5500.

When the wrist assembly 5500 is in the second orientation (FIGS. 21 and 24), the first distal central portion 5423 of the first tension member 5420 remains within the first curved guide path 5615, and is in contact with the first guide surface 5616. Moreover, the first distal central portion 5423 is spaced apart from the pulley 5660. Further, when the wrist assembly 5500 is in the second orientation (FIGS. 21 and 24), the second distal central portion 5433 of the second tension member 5440 remains within the second curved guide path 5620, and is in contact with (and at least partially wrapped about) the outer surface 5661 of the pulley 5660. Thus, when axial tension is applied to the second tension member 5440 for pitch movements or movement of the second tool member 5482 for yaw or grip movements, the pulley 5660 rotates along with movement of the second distal central portion 5433. The rotation of the pulley 5660 is based on contact with the second tension member 5440 at the outer surface 5661, and reduces friction that would otherwise occur when the tension member slides against the surfaces of the second link 5610 when tension is applied for pitch, yaw, or grip movements.

In some embodiments, the instrument 5400 is configured such that one or more pitch tension members (not shown) are additionally provided for assisting other tension members (e.g., the first and second tension members 5420, 5440) with producing pitch rotations and/or for the primary purpose of producing the pitch movements. The pitch tension members can be coupled to the second link 5610 in such as manner as to cause the second link to rotate with respect to the first link 5510 (i.e., a pitch rotation) when the pitch tension member(s) are moved. In this manner, the wrist assembly 5500 can be, for instance, a six-tension member (or six-cable) configuration (two pitch tension members or portions of pitch tension members controlling the pitch rotation and four tension members or portions of tension members controlling the yaw and grip rotations). In other embodiments any number of pitch tension members can be provided as appropriate to produce and/or assist with producing pitch movements in the wrist assembly. For example, referring to FIGS. 26-31, diagrammatic illustrations are shown of various portions of an instrument 6400 that includes a wrist assembly 6500 having a pitch tension member 6455 for producing pitch rotations, according to an embodiment. Instrument 6400 and wrist assembly 6500 generally include the aspects and preferences of the instruments described above including instruments 2400, 3400, 4400 and 5400 and the corresponding wrist assemblies, except as discussed below.

In some embodiments, the instrument 6400 or any of the components therein are optionally parts of a surgical system that performs minimally invasive surgical procedures, and which can include a manipulator unit, a series of kinematic linkages, a series of cannulas, or the like. The instrument 6400 (and any of the instruments described herein) can be used in any suitable surgical system, such as the MIRS system 1000 shown and described above. The instrument 6400 includes a wrist assembly 6500, at least one tension member 6455, and a tool member 6462. Although only one tension member 6455 is shown, one or more additional tension members can be included. As described herein, the instrument 6400 is configured such that movement of the tension member 6455 produces movement of the wrist assembly 6500 (as indicated by arrow BB shown in FIG. 26).

Figure 26:
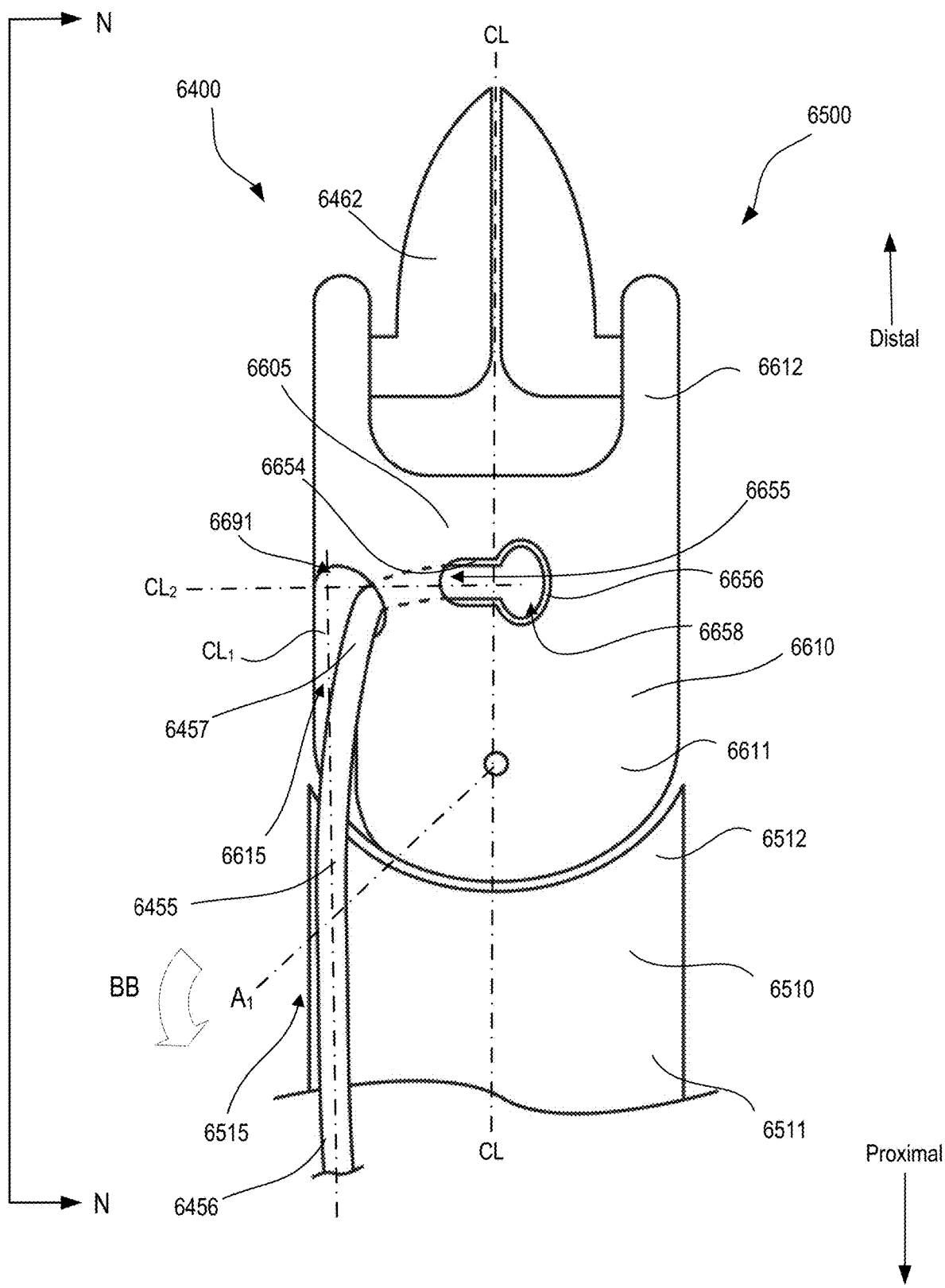
FIG. 26 is a diagrammatic front view of a portion of an instrument of a surgery system in a first orientation, according to an embodiment.
Figure 27:
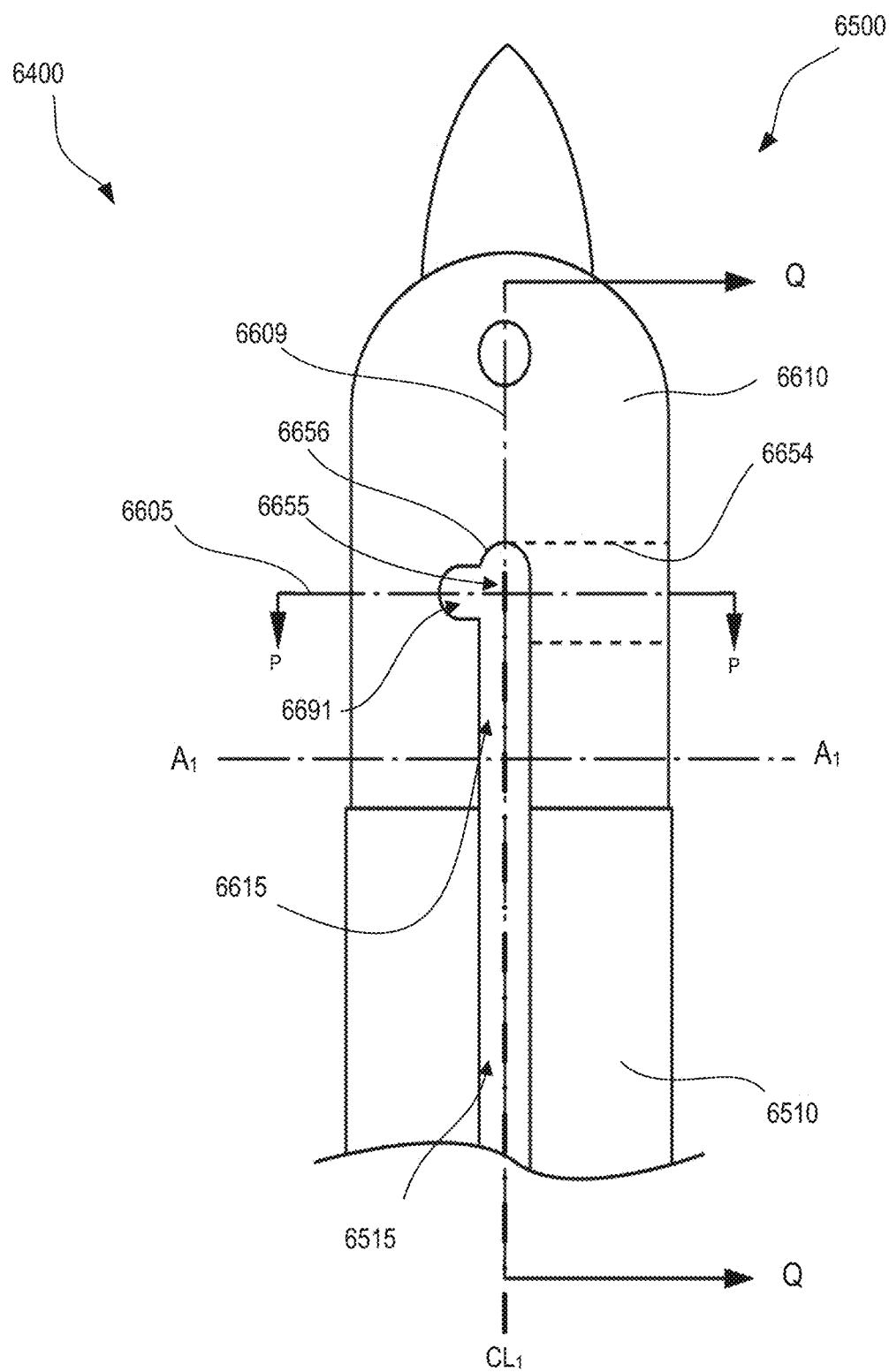
FIG. 27 is a diagrammatic side view of the portion of the instrument shown in FIG. 26 in the first orientation, as viewed according to line N-N shown in FIG. 26, and shown without the tension member to expose paths formed therein.
Figure 28:
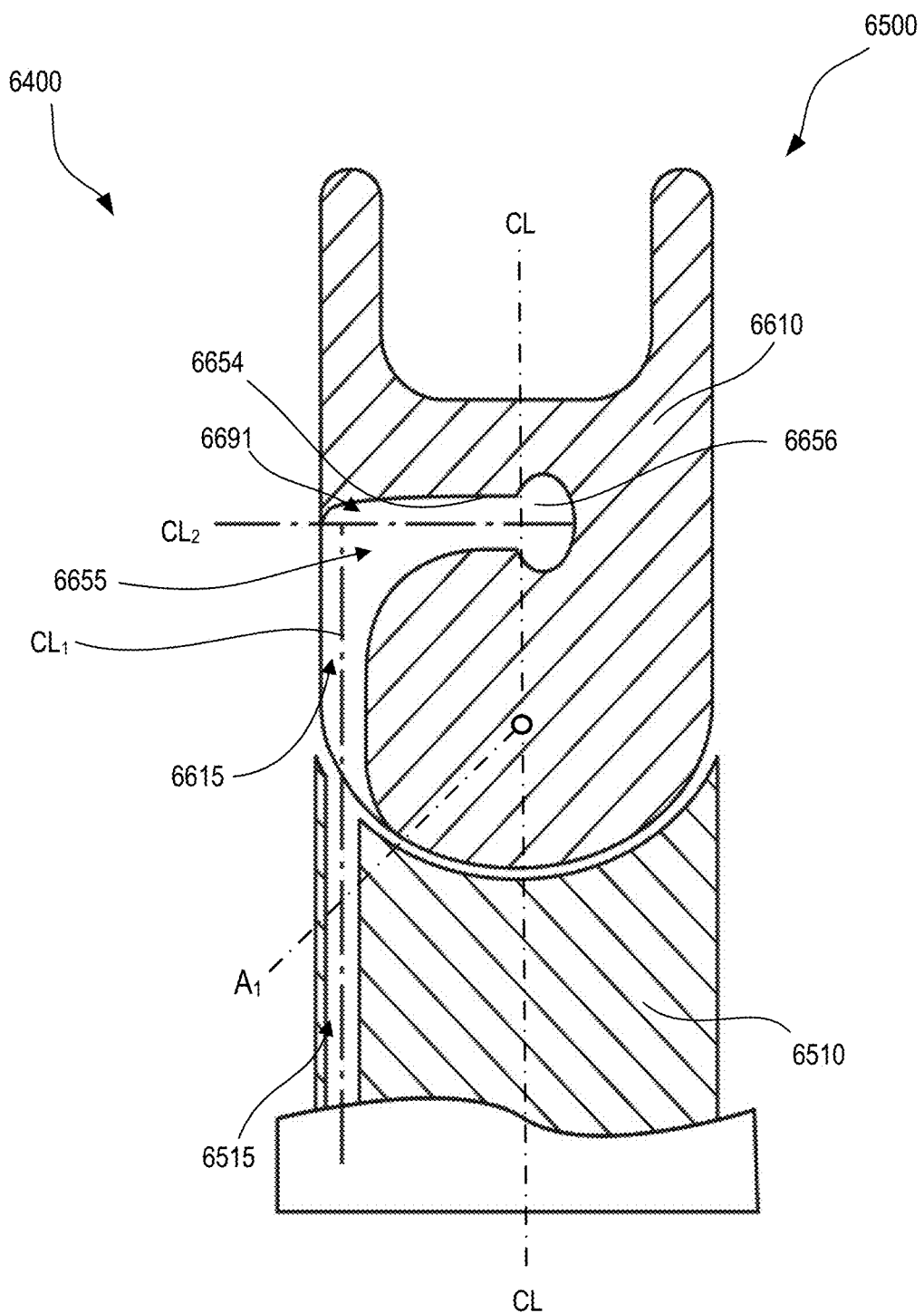
FIG. 28 is a diagrammatic, cross-sectional view of the portion of the instrument shown in FIGS. 26 and 27 in the first orientation, taken along line Q-Q shown in FIG. 27, and shown without the tension member to expose paths formed therein.

Referring to FIGS. 26-28, the wrist assembly 6500 includes a proximal first link 6510, and a distal second link 6610. The first link 6510 has a proximal end portion 6511 and a distal end portion 6512. The proximal end portion 6511 is coupled to an instrument shaft (not shown). Although the instrument shaft is not shown in FIGS. 26-31, the proximal end portion 6511 can be coupled to any suitable instrument shaft, such as the instrument shaft 4410 (FIG. 9) shown and described above along with instrument 4400. Moreover, the proximal end portion 6511 of the first link 6510 can be coupled to the instrument shaft via any suitable mechanism, such as welding, interference fit, adhesive, etc. As described below, the distal end portion 6512 is rotatably coupled to the second link 6610. In this manner, the first link 6510 and the second link 6610 form the wrist assembly 6500 having a first axis of rotation $A_1$ (which functions as a pitch axis; the term pitch is arbitrary) about which the second link can rotate relative to the first link through an angular range of the wrist assembly.

The proximal first link 6510 defines a first guide path 6515 within and through the first link, which extends from the proximal end portion 6511 of the first link to its distal end portion 6512. At least a portion of the first guide path 6515 is parallel with the centerline CL of the shaft, but is offset from the centerline of the shaft as discussed further below. As such, a centerline CU of the first guide path 6515 is offset from the centerline CL of the shaft by a distance. In some embodiments, the centerline CL of the shaft is coaxial with a centerline of the first link 6510 and intersects the first axis of rotation $A_1$.

The second link 6610 has a proximal end portion 6611 and a distal end portion 6612. As described above, the proximal end portion 6611 is rotatably coupled to the distal end portion 6512 of the first link 6510 to form a wrist joint. The axis of rotation $A_1$ is located on the centerline CL of the shaft and, in some embodiments, on the centerline of the first link 6510, as well as on the centerline of the second link 6610 as shown in FIG. 26. In a first orientation shown in FIGS. 26-28, the centerline CL of the first link 6510, and the centerline of the second link 6610 are collinear. Thus, the centerlines of the first and second links 6510, 6610 and the wrist assembly 6500 while in the first orientation of FIGS. 26-28 are collectively represented CL in FIGS. 26-28 for simplicity and to avoid confusion with centerlines of paths and/or other features defined in the wrist assembly 6500. Similar to wrist assemblies discussed above, the distal end portion 6612 of the second link 6610 includes a connector (not shown) that is coupled to the tool member 6462 such that the tool member 6462 can rotate relative to the wrist assembly 6500 about a second axis of rotation (not shown) through an angular range. The connector can be any suitable connector for rotatably coupling the tool member 6462 to the second link 6610 and forming a tool joint.

Referring to FIGS. 26-28, the second link 6610 defines a second guide path 6615, a retention pocket 6656, a connection path 6655 and an assembly path 6691. The second guide path 6615 is defined within and through a portion of the second link, and extends from the first guide path 6515 at the proximal end portion 6611 of the second link to the connection path 6655. The connection path 6655 is defined within and through a portion of the second link, and extends between the second guide path 6615 and the retention pocket 6656. In some embodiments, the connection path 6655 has a centerline $CL_2$ that intersects a centerline $CL_1$ of the second guide path 6615. A wall 6654 of the second link 6610 surrounds a portion of the connection path 6655. The second link 6610 defines the retention pocket 6656 as an interior cavity formed within the second link 6610, which is coupled to the connection path 6655 at one end of the connection path. In some embodiments, the second link 6610 can define a slot opening 6658 that can provide access to the retention pocket 6656, such as for use during installation of the tension member 6455. As also described in further detail below, the retention pocket 6656 is configured to receive and retain therein a retention member 6459 that is coupled to the tension member 6455. Further, the retention pocket 6656 is sized to extend beyond a cross-section of the connection path 6655 at its connection therewith, so that the wall 6654 surrounding the connection path 6655 forms a stop that can help retain therein the retention member 6459. Similar to the connection path 6655, the assembly path 6691 is also defined within and through a portion of the second link 6610, and also extends between the retention pocket 6656 and a portion of the second link that is proximate to the centerline $CL_1$ of the second guide path 6615. However, as discussed in greater detail below along with the tension member 6455, the assembly path 6691 is angled away from the connection path 6655 as the paths extend outward from the retention pocket 6656.

The centerline $CL_2$ of the connection path 6655 is aligned with a centerline $CL_1$ of the second guide path 6615 such that the two paths together form a combined path for the tension member between the first guide path 6515 in the first link 6510 and the retention pocket 6656 formed within the second link 6610. As such, the connection path centerline $CL_2$ intersects the second guide path centerline $CL_1$ at the intersection of the two paths. The intersecting centerlines $CL_1$, $CL_2$ of the aligned paths define a first plane 6605 within the second link 6610. In some embodiments, the first plane 6605 is oriented such that it is transverse with respect to the longitudinal axis of the second link 6610. As shown in FIG. 27, the first plane 6605 defined in wrist assembly 6500 corresponds with the cross-sectional view line Q-Q. As such, the cross-sectional view of FIG. 28 that is taken according to line Q-Q shown in FIG. 27 provides a view of the wrist assembly 6500 along the first plane 6605 including the centerline $CL_1$ of the second guide path 6615 and the centerline $CL_2$ of the connection path 6655.

Figure 29:
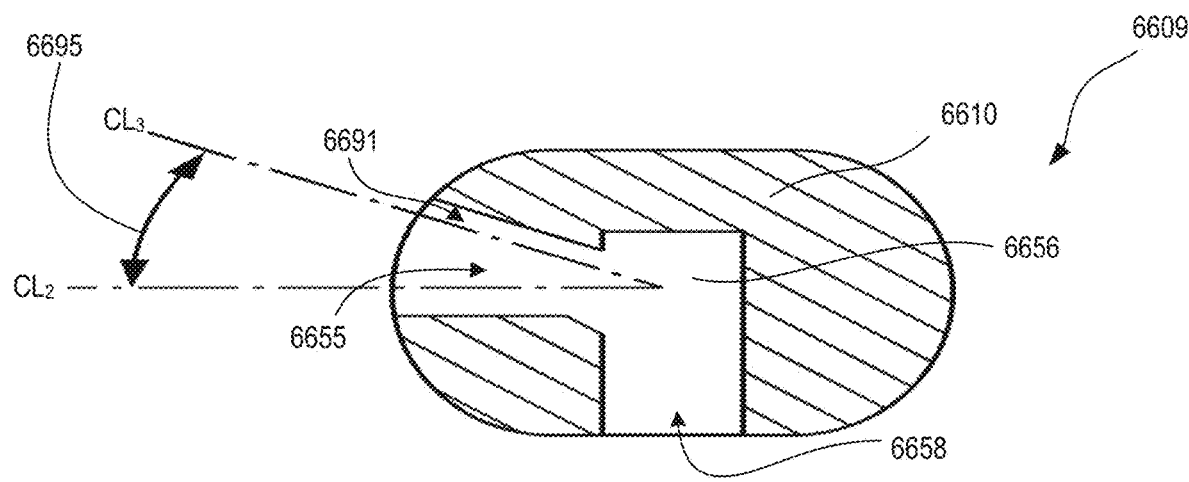
FIG. 29 is a diagrammatic, cross-sectional view of the portion of the instrument shown in FIGS. 26 and 27 in the first orientation, taken along line P-P shown in FIG. 27, and shown without the tension member to expose paths formed therein.

Referring to FIGS. 27 and 29, the assembly path 6691 is not parallel to the second guide path 6615. Rather, as shown FIG. 29, the assembly path 6691 is nonparallel to (or angled away from) the connection path 6655 as it extends outward from the retention pocket 6656. Further, the centerline $CL_3$ of the assembly path 6691 is configured to be nonparallel to the connection path centerline $CL_2$ of the connection path 6655 within a second plane 6609, which is nonparallel to the first plane 6605. Because both the connection path 6655 and the assembly path 6691 connect with the retention pocket 6656, the centerline $CL_3$ of the assembly path forms an insertion angle 6695 with respect to the centerline $CL_2$ of the connection path at the retention pocket 6656 when considered from a plane other than from the first plane 6605.

Stated differently, the assembly path 6691 extends outward from the retention pocket 6656 at an insertion angle 6695 that is oriented away from the connection path 6655 and away from the path of the tension member 6455 within the second link 6610 along the first plane 6605, which includes the second guide path 6615 and the connection path 6655 aligned to form a path between the first guide path 6515 (e.g., a first link guide path) and the retention pocket 6656 for the tension member. As discussed further below, the orientation of the assembly path 6691 at the insertion angle 6695 with respect to the connection path 6655 and the first plane 6605 allows the tension member 6455 to be installed and routed more easily within the second link 6610 while avoiding damage to the tension member 6455 during installation. Further, the second link defines an open path at inner portions of the second link located between the connection path 6655 and the assembly path 6691 within the insertion angle 6695 (see FIG. 29). Stated differently, the inner side portion of the connection path 6655 and the assembly path 6691 located between the two paths is open such that tension member 6455 can be moved from the assembly path 6691 to the connection path 6655 as appropriate during installation of the tension member.

Referring to FIGS. 26 and 29-31, the tension member 6455 has a proximal end portion 6456, a distal end portion 6458 that is coupled to a retention member 6459, and a central portion 6457 disposed between the proximal end portion and the distal end portion. The proximal end portion 6456 is located within a portion of the first guide path 6515 of the first link 6510. Further, the proximal end portion 6456 is coupled to an instrument shaft (not shown), which is coupled to a housing of a transmission mechanism, such as transmission mechanism 4700 discussed above. The central portion 6457 is between the distal end portion 6458 and the proximal end portion 6456, and is located within the second guide path 6615 of the second link 6610 and within a portion of the connection path 6655. The retention member 6459 is connected to the distal end portion 6458 of the tension member 6455 and is configured to fit within the retention pocket 6656 such that the distal end portion 6458 of the tension member extends from retention member 6459 and the retention pocket 6656 to be within the connection path 6655. The retention member 6459 is sized such that it is larger than the distal end portion 6458 of the tension member at its connection thereto. Further, the retention member 6459 is sized to fit within the retention pocket 6656 such that the wall 6654 surrounding the connection path 6655 forms a stop to assist with retaining the retention member 6459 within the retention pocket 6656 when tension is applied to the tension member along its longitudinal axis for providing pitch movements of the second link 6610 with respect to the first link 6510. Stated differently, the retention member 6459, the retention pocket 6656 and the connection path 6655 are configured such that the retention member is unable to move with the connection path 6655.

Thus, the wrist assembly 6500 is configured to securely retain the tension member 6455 within the connection path 6655 and the second guide path 6615 during pitch movements in the direction BB shown in FIG. 26, for example, for angular rotations about the first axis $A_1$ away from the first orientation shown in FIG. 26. The retention pocket 6656 securely retains the retention member 6459 therein based on beneficial features, such as interference with stop features like the wall 6654 surrounding a portion of the connection path 6655, as well as the retention pocket 6656 being sized to be larger than the cross-section of the connection path 6655, and the retention member being sized to fit within the retention pocket 6656 and also to extend beyond the cross-section of the distal end portion 6458.

In addition, the wrist assembly 6500 is further configured to improve the ease of installing the tension member 6455 within the wrist assembly 6500 including routing the tension member 6455 through the second link 6610 and installing the retention member 6459 within the retention pocket 6656 and other features that can provide benefits for retaining the tension member within the second link 6610. Further, the wrist assembly 6500 is configured to reduce the likelihood of the tension member 6455 being damaged during installation, such as avoiding bends or kinks from forming within the tension member, and reducing the likelihood of cuts and abrasions to the tension member from installation. Such damage to the tension member can induce areas of stress concentration within the tension member, permit corrosion to occur more quickly, adversely impact its structural integrity, change its performance properties, and otherwise degrade the function, longevity and performance of the tension member.

Figure 30:
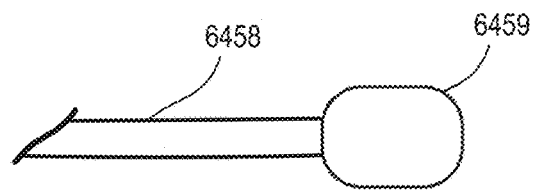
FIG. 30 is a diagrammatic top view of a distal end portion of the tension member of the portion of the instrument shown in FIGS. 26 and 27.

Referring to FIGS. 29-30, the instrument 6400 and the wrist assembly 6500 are configured to allow easy installation of the tension member 6455 and the retention member 6459 therein along with providing the retention benefits described above, as well as to reduce the likelihood of damaging the tension member 6455 during installation. As illustrated in FIGS. 29-30, the wrist assembly 6500 and the tension member 6455 are configured such that the proximal end portion 6456 and the central portion 6457 of the tension member 6455 can be: A) inserted through the assembly path 6691 along the assembly path centerline $CL_3$; and B) the proximal end portion 6456 and the central portion 6457 can be rotated until the proximal end portion 6456 is within the first guide path 6515 (FIG. 26) and the central portion 6457 is within the second guide path 6615, such that the distal end portion 6458 is within the connection path 6655 when assembled.

Figure 31C:
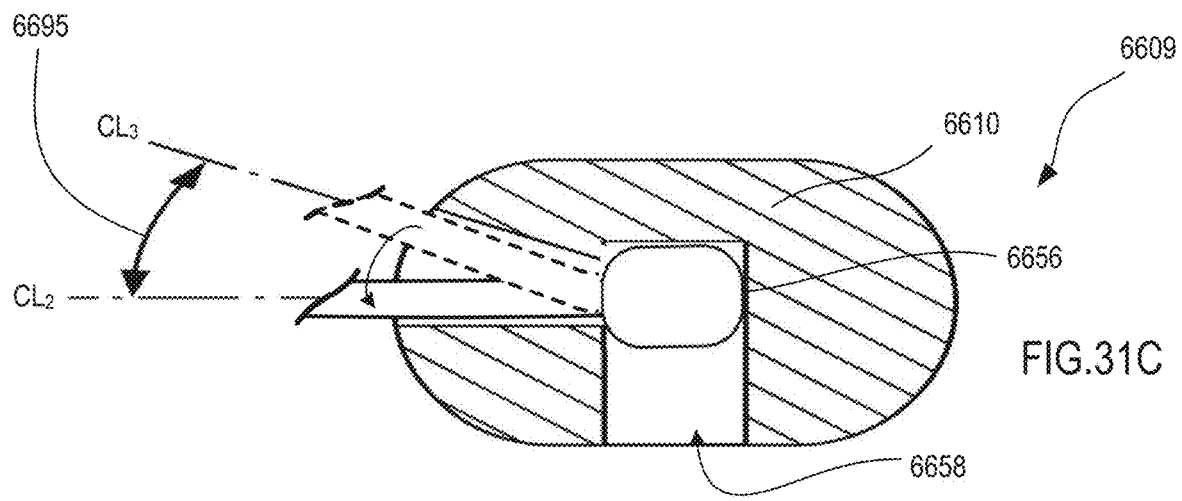
FIGS. 31B and 31C are diagrammatic, cross-sectional views of the portion of the instrument shown in FIGS. 26 and 27, taken along line P-P shown in FIG. 27, and each shown along with a top view of the distal end portion of the tension member of FIG. 30 to illustrate an installation method, according to an embodiment.
Figure 31B:
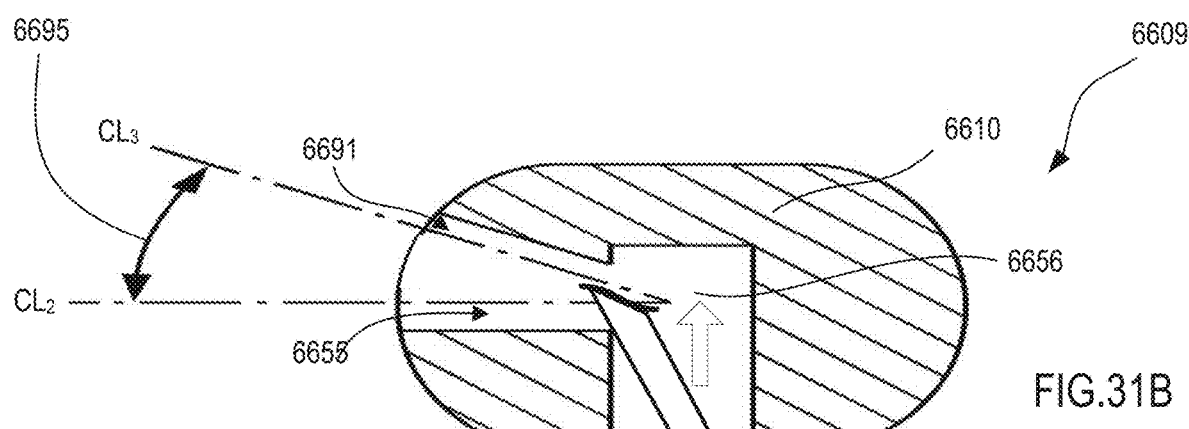
Figure 31A:
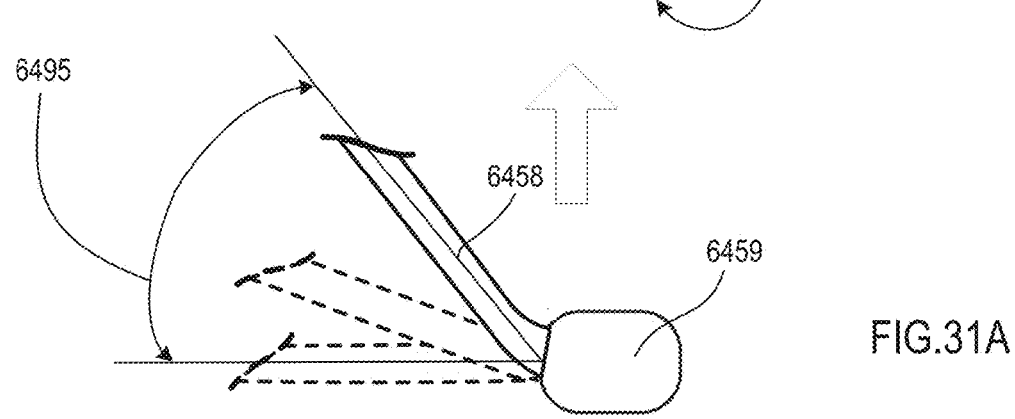
FIG. 31A is a diagrammatic top view of a distal end portion of the tension member of the portion of the instrument shown in FIGS. 26 and 27, which illustrates installation bends in the tension member as part of an installation method, according to an embodiment.

As shown in FIG. 31A, the tension member 6455 can be flexed within its range of flexibility based on its modulus of elasticity and other tension member properties at an appropriate bend angle 6495 to assist with installation of the tension member while avoiding excessive bending or flexing that can damage the tension member. The tension member 6455 cam be installed by threading the proximal end portion 6456 and the central portion 6457 into the second link through the exposed slot opening 6658 of the retention pocket 6656. The bend angle 6495 can be an acute angle as shown in FIG. 31A that flexes the tension member with respect to the retention member 6459 by a small angle to assist with installation while avoiding avoid kinking, permanently bending or otherwise damaging the tension member, such as can occur at much larger bend angles. In some embodiments, the bend angle can be more than the insertion angle 6695. In some embodiments, the bend angle can be the same as the insertion angle 6695, and in some embodiments the bend angled can be less than the insertion angle 6695. As described above, the assembly path 6691 is configured and oriented with the respect to the retention pocket such that the assembly path is angled away from the connection path 6655 as the paths extend outward from the retention pocket 6656 at insertion angle 6695. In addition, as shown in FIGS. 31B and 31C, the centerline $CL_1$ of the assembly path can be oriented away from the connection path 6655 such that the assembly path 6691 is aligned as much as possible with the slot opening 6658. As such, an installation path is formed through the slot opening 6658 and the retention pocket 6656, and into and through the angled assembly path 6691, which avoids flexing the tension member 6455 at large bend angles or through contoured paths to install the tension member within the wrist assembly 6500.

When the tension member 6455 has been threaded through the assembly path 6691 completely such that the retention member 6459 is retained and installed within the retention pocket 6656 as shown in FIG. 31C, the tension member can be moved from the assembly path 6691 into the connection path 6655 through the open spaced between the two paths. Thus, the tension member 6455 along with the retention member 6459 can be installed within the wrist assembly 6500 without significantly bending or flexing the tension member or routing it through tight bends that damage the tension member. In some embodiments (not shown), the retention member 6459 can be coupled to the distal end portion 6458 of the tension after the tension member has been partially installed, such as while in the position shown in FIG. 31B. Doing so can further avoid excessive bending and flexing of the tension member during installation. However, coupling the retention member 6459 to the tension member 6455 after partially installing the tension member can add other difficulties, such as increasing the likelihood of damage to the wrist assembly 6500 while attaching the retention member or reducing the quality or integrity of the connection between the retention member 6459 and the distal end portion 6458 of the tension member.

Many of the benefits and advantages discussed herein along with the various embodiments can be applied to other example embodiments shown or described herein, and/or combined in additional other embodiments. For example, many of the aspects and features of the wrist assembly 6500 pertaining to having one or more tension members configured to provide pitch movements can be combined with other embodiments having tension members that provide pitch movements along with movements of the end effector. For instance, in some embodiments, one or more tension members similar to tension member 6455 of wrist assembly 6500 can be added to another instrument, such as instrument 5400 and wrist assembly 5500. Said another way, although the instrument 5400 is shown as including a four-cable wrist assembly 5500, in other embodiments the wrist assembly 5500 can include two additional pitch cables. In such embodiments, the four cable ends (e.g., 5421, 5431, 5441, 5451) can be routed along similar friction reducing guide paths as described above, and can be manipulated to control the grip or yaw rotation of the end effector and two additional cable ends (see 7456, 7457) can be manipulated to control pitch movement. Moreover, in such embodiments the pitch cable (or cable ends) can be installed in a manner similar to that described above with reference to the instrument 6400.

For example, FIGS. 32-41 show an instrument 7400 having a wrist assembly 7500, according to an embodiment. The instrument generally includes the low-friction aspects and components of the instruments described above including instruments 2400, 3400, 4400 and 5400 and the corresponding wrist assemblies, except as discussed below. In particular, the instrument 7400 includes certain components and features described above for instrument 5400 and wrist assembly 5500 (see FIGS. 18-25), and such components are not described in detail below. Additionally, unlike the instrument 5400, the instrument 7400 also includes an additional tension member (with two proximal end portions, 7456 and 7457) such that the wrist assembly 7500 is a six-cable wrist. The additional guide paths, pitch control and movements of the wrist assembly 7500, as well as installation of a third tension member 7455 (e.g., a pitch tension member) are discussed below.

Figure 32:
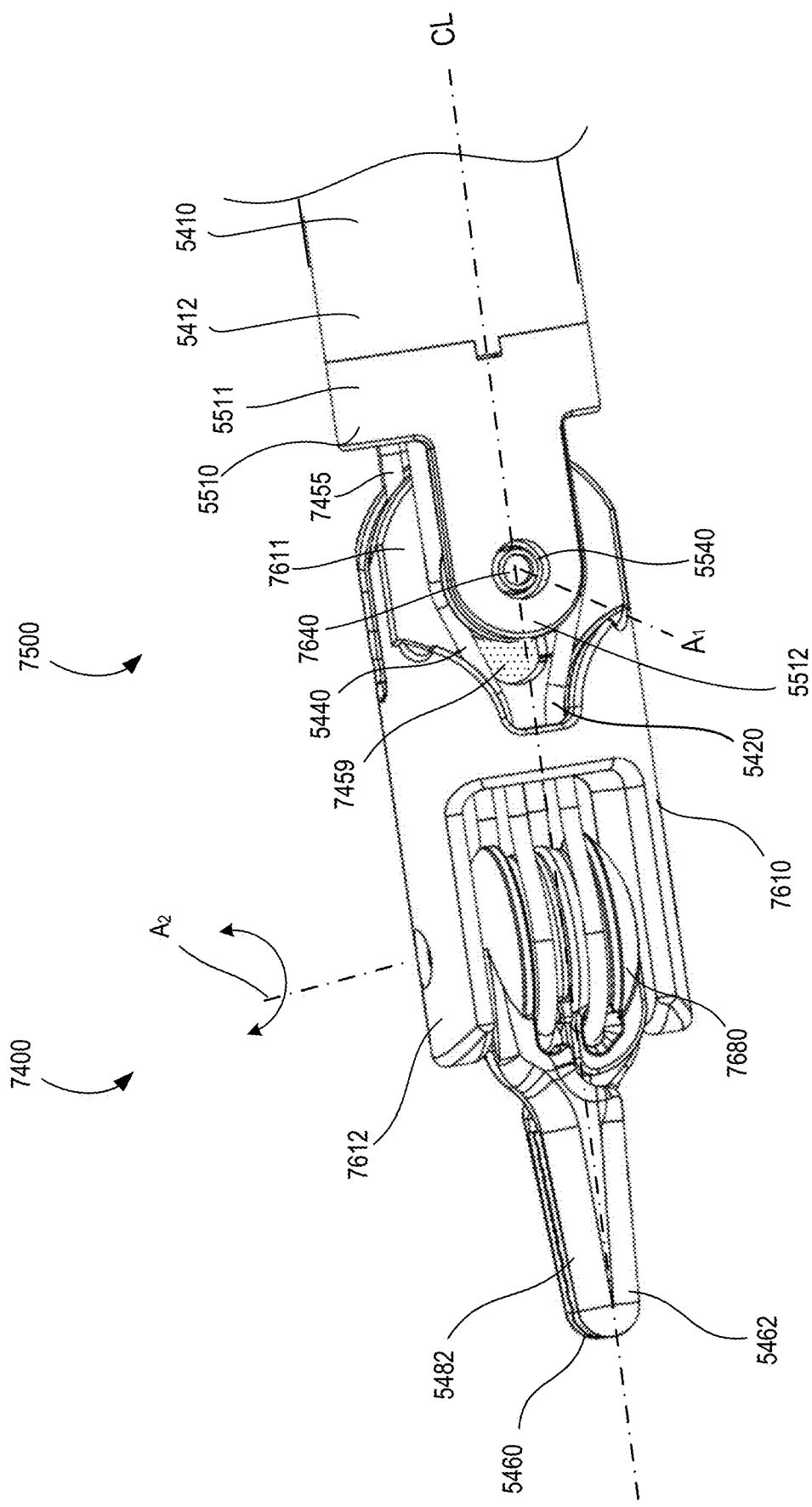
FIG. 32 is an enlarged perspective view of a distal end portion of an instrument in a first orientation, according to an embodiment.
Figure 33:
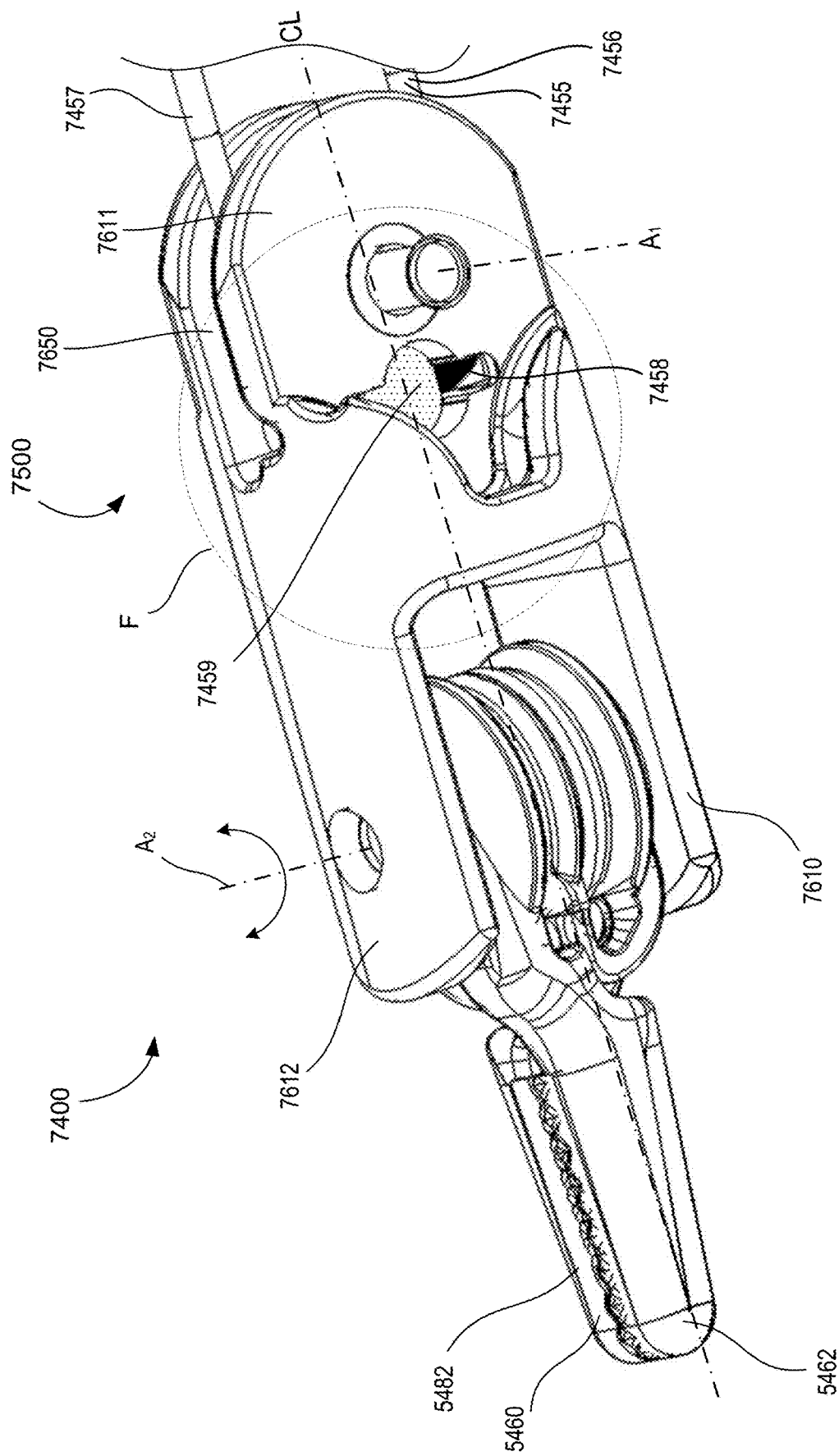
FIG. 33 is an enlarged perspective view of the distal end portion of the instrument of FIG. 32, shown with some of the tension members, the first link, and a pulley removed to expose portions of the second link.

The instrument 7400 and wrist assembly 7500 shown in FIGS. 32-42 can include any suitable transmission assembly (not shown in FIGS. 32-42), such as the transmission assembly 5700 described above. Additionally, the instrument 7400 includes an instrument shaft 5410, a wrist assembly 7500, and an end effector 5460. Referring to FIG. 32, the instrument 7400 also includes a first tension member 5420 and a second tension member 5440 that couple the transmission assembly to the wrist assembly 7500, as described in greater detail above with reference to FIGS. 18-25. However, instrument 7400 is configured such that movement of the tension members 5420, 5440 can produce yaw rotation of the end effector 5460 about a second axis of rotation $A_2$ ("yaw axis"), and grip rotation of the tool members of the end effector 5460 about the yaw axis, or any combination of these movements. In addition, instrument 7400 and wrist assembly 7500 includes a third tension member 7455 that, when moved, produces pitch movements by rotating the second link 7610 with respect to the first link 5510 about the first axis, $A_1$, for a range of angular rotation as described further below. In other embodiments (not shown), pitch movements can be provided by a combination of movements of the first and second tension members along with movements of the third pitch tension member.

Figure 35:
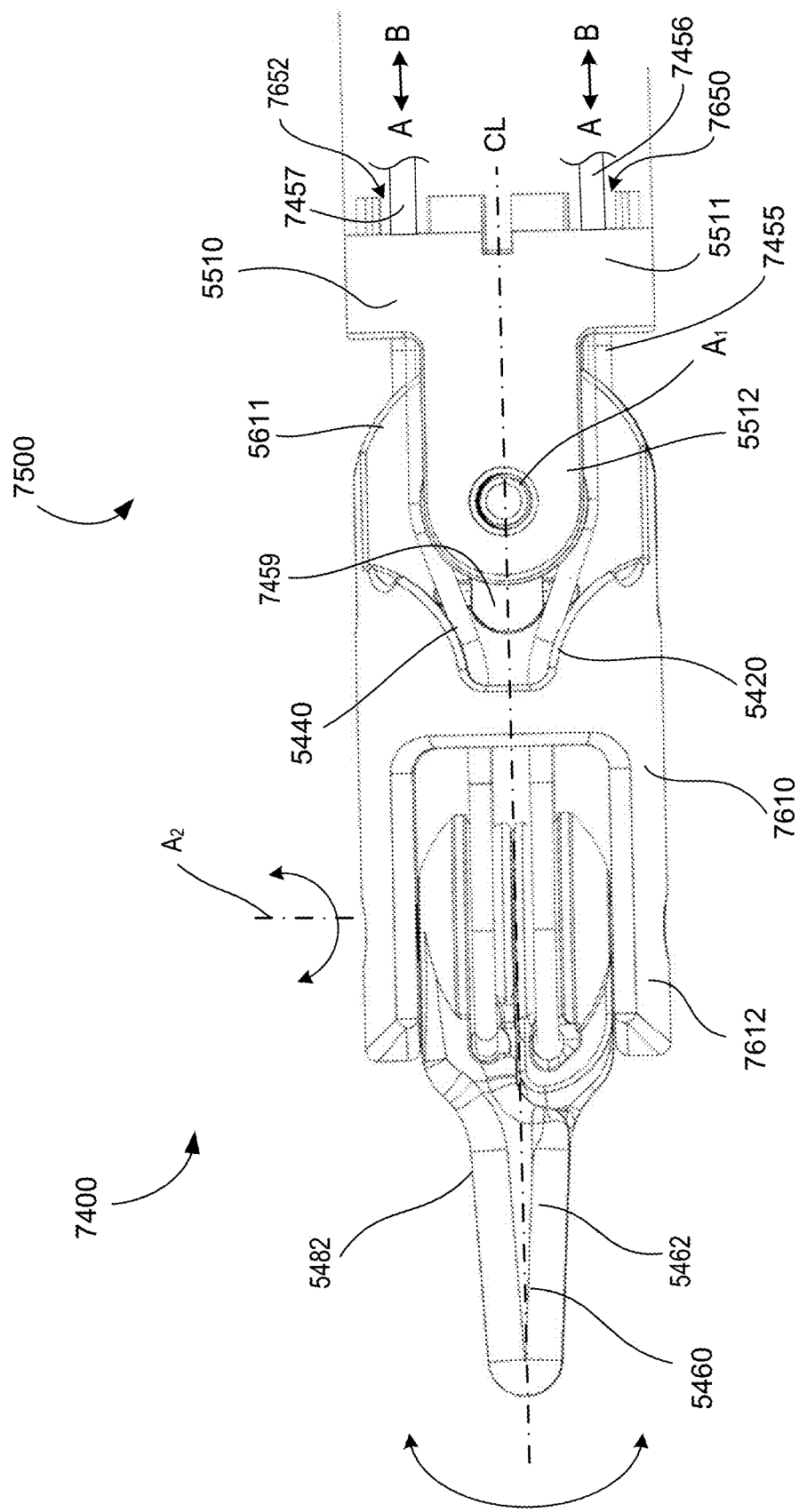
FIG. 35 is a side view of the distal end portion of the instrument of FIG. 32 in a first orientation.
Figure 38:
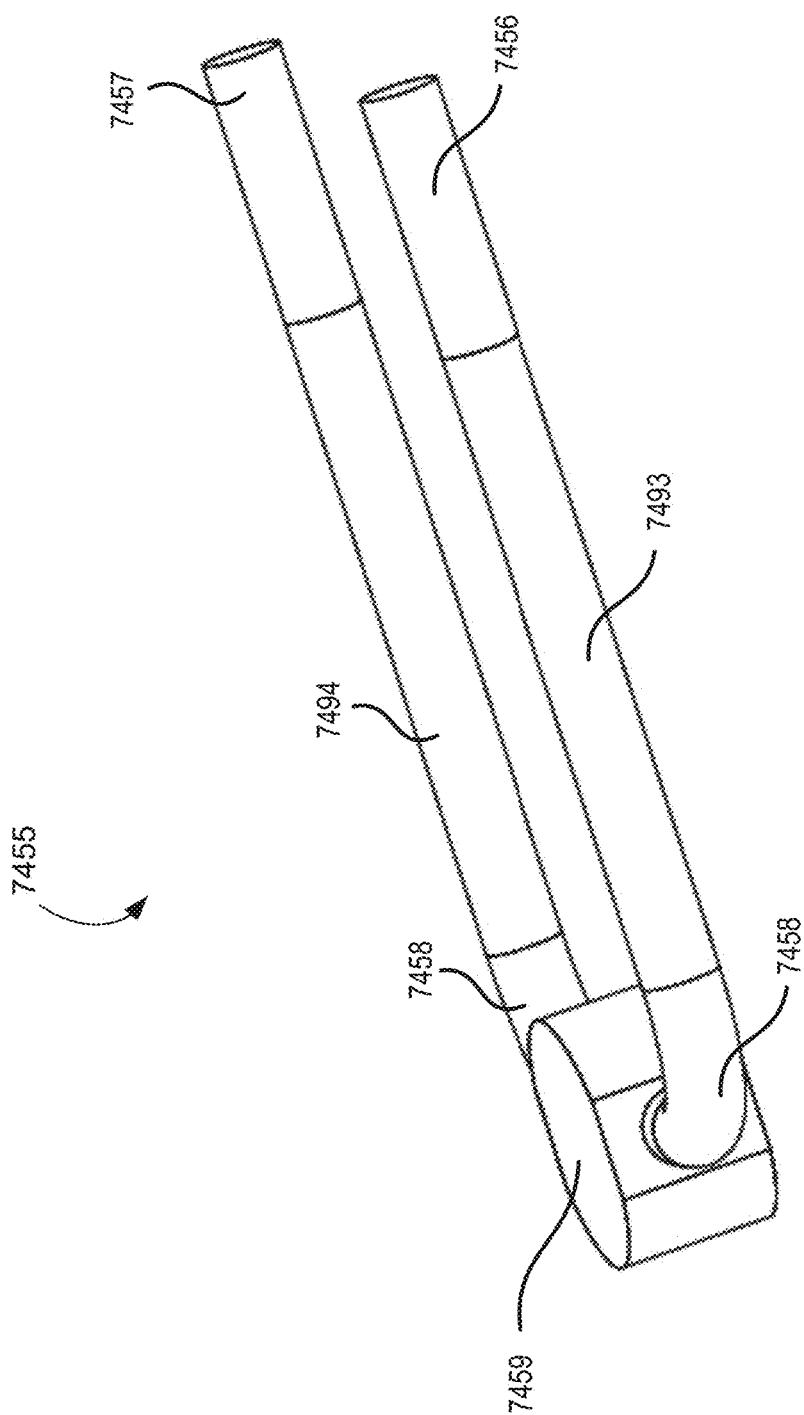
FIG. 38 is a perspective view of the third tension member of the instrument of FIG. 32.

Referring to FIG. 32, the wrist assembly 7500 includes a first link 5510 (proximal first link) and a second link 7610 (e.g., a distal second link). The first link 5510 has a proximal end portion 5511 and a distal end portion 5512. The proximal end portion 5511 is coupled to the distal end portion 5412 of the instrument shaft 5410. The distal end portion 5512 includes a joint portion 5540 that is rotatably coupled to a mating joint portion 7640 of the second link 5610. In this manner, the first link 5510 and the second link 7610 form the wrist assembly 5500 having a first axis of rotation $A_1$ (also referred to as the pitch axis) about which the second link 7610 can rotate relative to the first link 5510. As shown in FIG. 32, the first link 5510 and the second link 7610 define a longitudinal centerline that intersects the pitch axis $A_1$ when the instrument is in a first (or "straight") orientation, which is collinear with the shaft centerline CL. As shown in FIG. 35, the first link 5510 defines a fifth guide path 7650 and a sixth guide path 7652 that are configured to guide portions of the third tension member 7455 as described further below. The fifth guide path 7650 and the sixth guide path 7652 are similar to the guide paths (e.g., guide channels) shown and described above with reference to FIG. 11.

Referring to FIGS. 32-37, the second link 7610 has a proximal end portion 7611 and a distal end portion 7612. As described above, the proximal end portion 7611 includes a joint portion 7640 that is rotatably coupled to the joint portion 5540 of the first link 5510. The distal end portion 7612 of the second link 7610 includes a connector 7680 that is coupled to the end effector 5460. In this manner, the first tool member 5462 and the second tool member 5482 can rotate relative to the second link 7610 about a second axis of rotation (also referred to as the yaw axis) $A_2$. In addition to the guide paths for the first tension member 5420 and the second tension member 5440 (which are similar to the curved guide paths 5615, 5620 described above), the second link 7610 also defines a fifth guide path 7650, a sixth guide path 7652, a retention pocket 7656, a connection path 7655, and an assembly path 7691. The fifth guide path 7650 and sixth guide path 7652 are each defined within and through a portion of the second link, and each extends from a corresponding one of the fifth guide path 7650 and sixth guide path 7652 of the second link 5610 to the connection path 7655.

Figure 34:
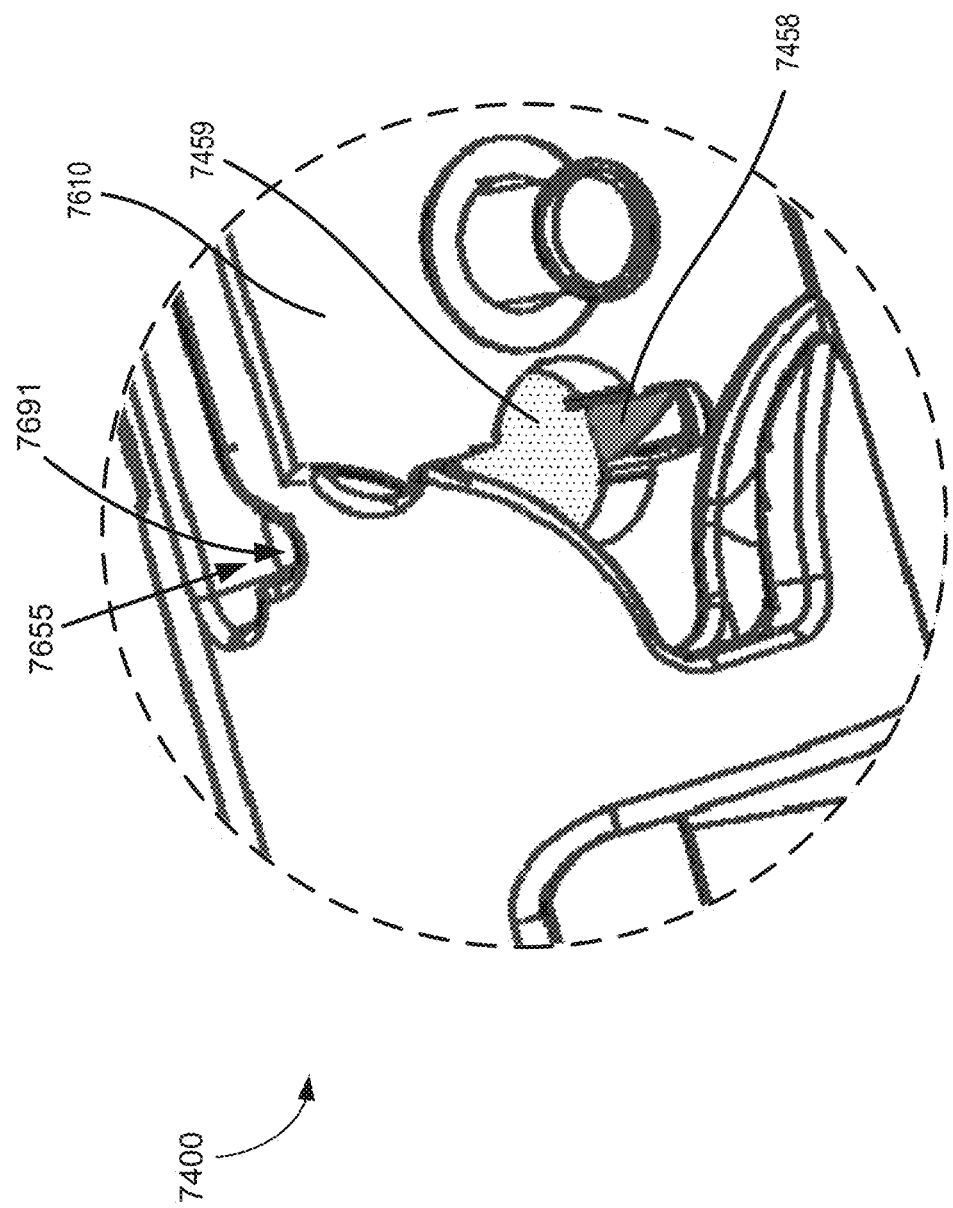
FIG. 34 is an enlarged perspective view of a portion of the instrument of FIGS. 32 and 33 indicated by the region F shown in FIG. 33.
Figure 41:
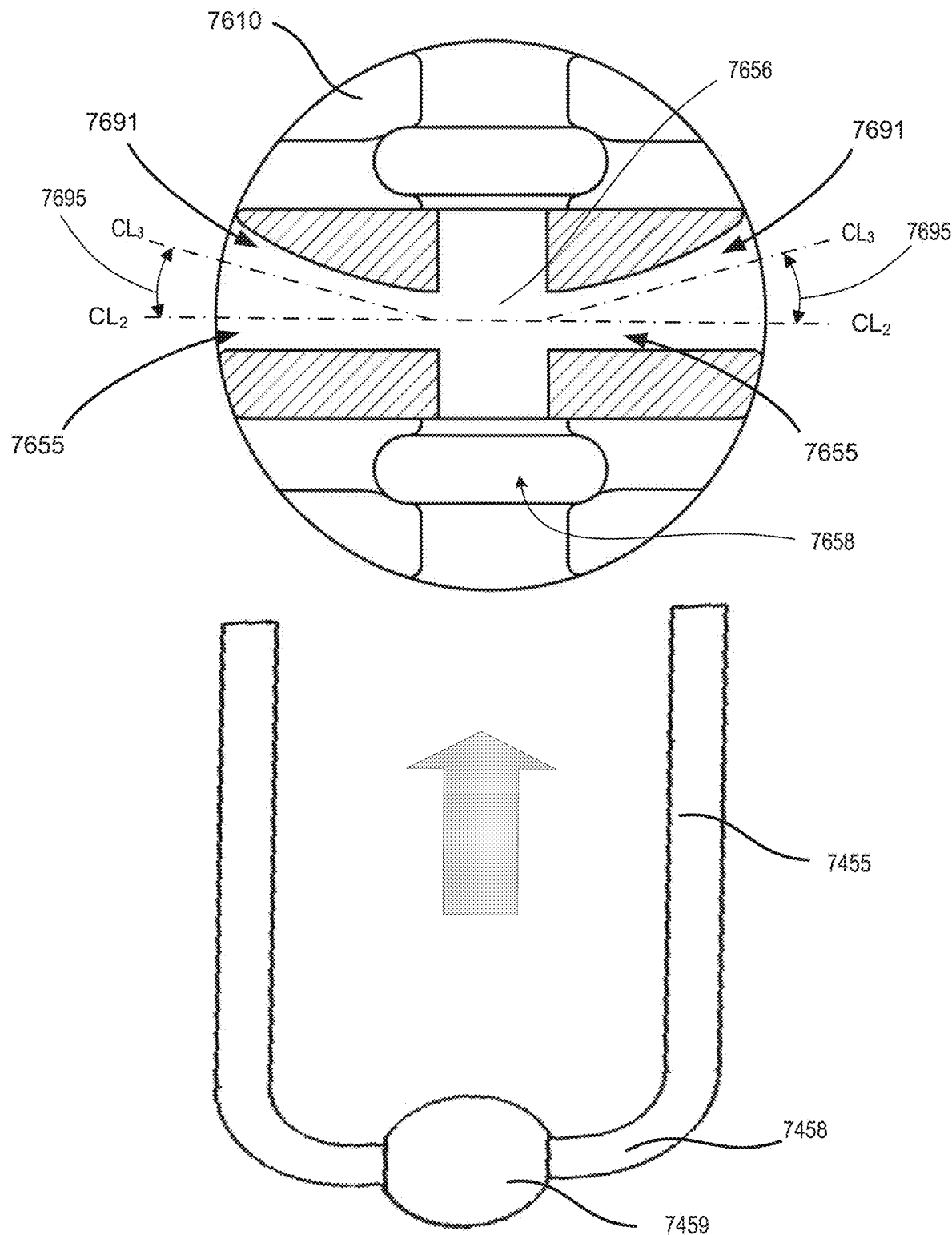
FIGS. 41 and 42 are top cross-sectional views of portions of the second link of the instrument of FIG. 32 and the pitch tension member for installation of the pitch tension member shown in FIGS. 38 and 39, viewed from line W-W shown in FIG. 38.
Figure 42:
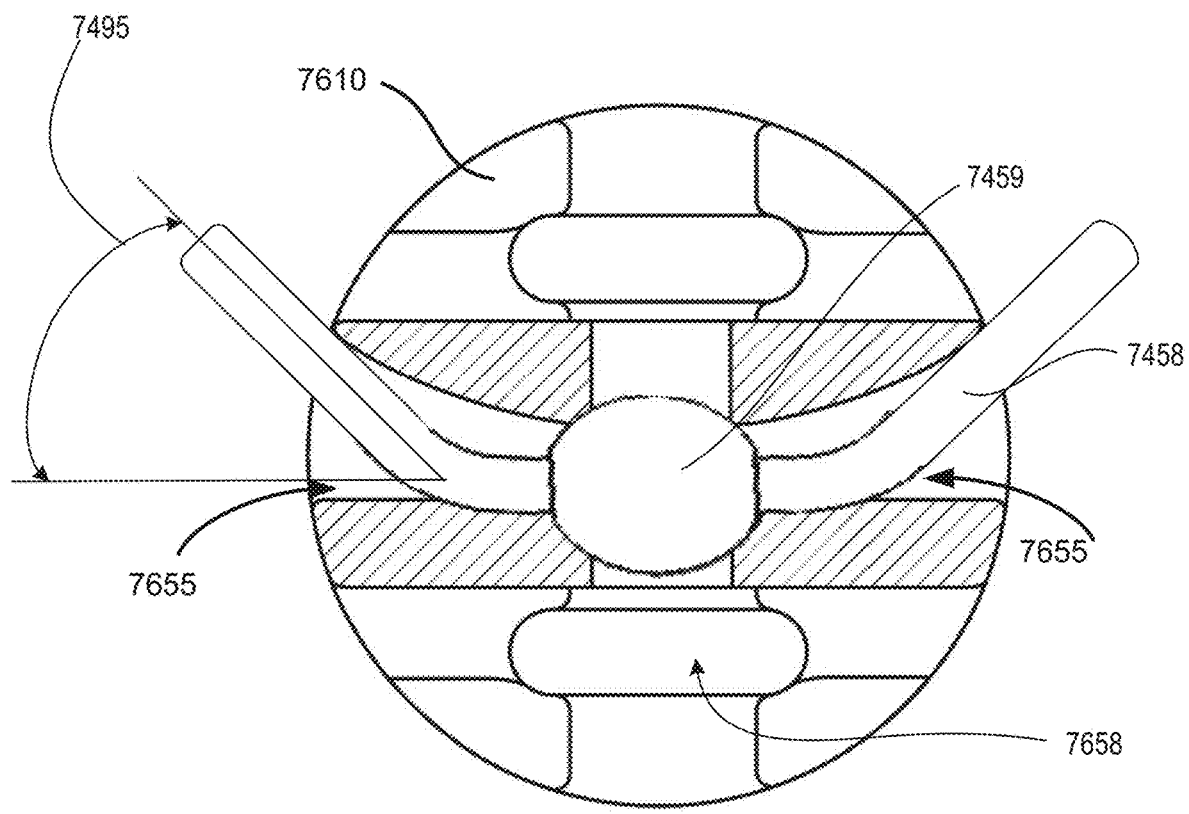

As shown in FIGS. 34, 41, and 42, the connection path 7655 is defined within and through a portion of the second link 7610, and extends between the retention pocket 7656 and each of the fifth and sixth guide paths 7650, 7652. In some embodiments, the connection path 7655 has a centerline $CL_2$ that intersects a centerline $CL_1$ of each of the fifth and sixth guide paths 7650, 7652 (FIG. 36). Referring to FIGS. 36 and 37, a wall 7654 of the second link 7610 surrounds a portion of the connection path 7655. The second link 7610 defines the retention pocket 7656 as an interior cavity formed within the second link 7610, which is coupled to a central portion of the connection path 7655. The second link 7610 defines a slot opening 7658 that can provide access to the retention pocket 7656, such as for use during installation of the third tension member 7455. As also described in further detail below, the retention pocket 7656 is configured to receive and retain therein a retention member 7459 that is coupled to the third tension member 7455. Further, the retention pocket 7656 is sized to be larger than a cross-section of the connection path 7655, so that the wall 7654 surrounding the connection path 7655 forms a stop that can help retain therein the retention member 7459. Similar to the connection path 7655, the assembly path 7691 is also defined within and through a portion of the second link 7610, and also extends from the retention pocket 7656 to portions of the second link that are proximate to the centerline $CL_1$ of each of the fifth and sixth guide paths 7650, 7652. However, as discussed in greater detail below along with the third tension member 7455, the assembly path 7691 is angled away from the connection path 7655 as the paths extend outward from the retention pocket 7656.

Figure 39:
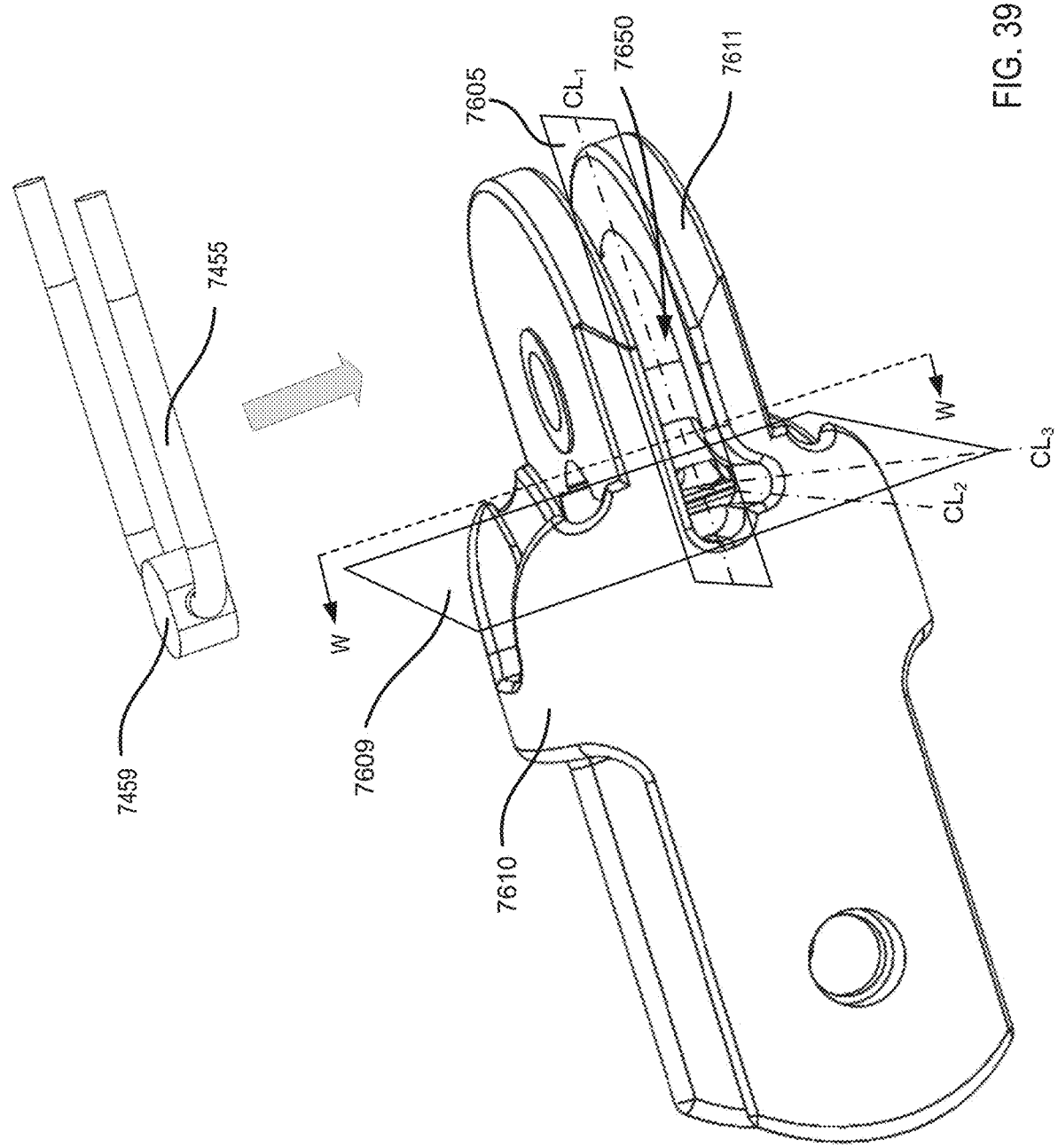
FIGS. 39 and 40 are perspective views of the second link of the instrument of FIG. 32 in the first orientation and portions of a pitch tension member illustrating installation of the pitch tension member.

The centerline $CL_2$ of the connection path 7655 is aligned with a centerlines $CL_1$ of the fifth and sixth guide paths 7650, 7652. Thus, the connection path 7655 and the fifth and sixth guide paths 7650, 7652 together form a combined path for the third tension member 7455 between the fifth and sixth guide paths 7650, 7652 in the first link 5510 that extends through the retention pocket 7656 formed within the second link 7610. As such, the connection path centerline, $CL_2$, intersects the centerlines $CL_1$ at the intersection of the connection path 7655 with the fifth and sixth guide paths 7650, 7652. The centerlines $CL_1$ of the fifth guide path 7650 and the sixth guide path 7652 define a first plane 7605 within the second link 7610 (FIG. 39). In some embodiments, the first plane 7605 is oriented such that it is transverse with respect to the longitudinal axis of the second link 7610. The centerline $CL_2$ of the connection path 7655 can lie within a second plane 7609 within the second link 7610 (FIG. 39). The second plane 7609 can be normal to the first plane 7605.

Referring to FIGS. 41 and 42, which shows a cross-section of the second link 7610 taken along the second plane 7609, the assembly path 7691 is not parallel to the fifth and sixth guide paths 7650, 7652. Rather, as shown FIG. 41, the assembly path 7691 is nonparallel to (or angled away from) the connection path 7655 as it extends outward from the retention pocket 7656. Said another way, the centerline $CL_3$ of the assembly path 7691 is configured to be nonparallel to the connection path centerline $CL_2$ of the connection path 7655 within a second plane 7609, which is nonparallel to the first plane 7605. Because both the connection path 7655 and the assembly path 7691 connect with the retention pocket 7656, the centerline $CL_3$ of the assembly path forms an insertion angle 7695 (e.g., an assembly angle) with respect to the centerline $CL_2$ of the connection path at the retention pocket 7656 when considered from a plane other than from the first plane 7605.

Stated differently, the assembly path 7691 extends outward from the retention pocket 7656 at an insertion angle 7695 that is oriented away from the connection path 7655 and away from the fifth and sixth guide paths 7650, 7652 of the tension member 7455 within the second link 7610 along the first plane 7605. The insertion angle 7695 can have any suitable value, e.g., from five degrees to 45 degrees. As discussed further below, the orientation of the assembly path 7691 at the insertion angle 7695 with respect to the connection path 7655 and the first plane 7605 allows the third tension member 7455 to be installed and routed more easily within the second link 7610 while avoiding damage to the third tension member 7455 during installation. Further, the second link 7610 defines an open path at inner portions of the second link located between the connection path 7655 and the assembly path 7691 within the insertion angle 7695 (see FIG. 41). Stated differently, the inner side portion of the connection path 7655 and the assembly path 7691 located between the two paths is open such that third tension member 7455 can be moved from the assembly path 7691 to the connection path 7655 as appropriate during installation of the tension member.

Referring to FIGS. 34, 35, 38 and 39, the third tension member 7455 has a first proximal end portion 7456, a distal end portion 7458 that is coupled to a retention member 7459, a first central portion 7493 disposed between the first proximal end portion 7456 and the distal end portion 7458, and a second central portion 7494 disposed between the distal end portion 7458 and a second proximal end portion 7457. When installed, the first proximal end portion 7456 is located within a portion of the fifth guide path 7650 of the first link 5510. Similarly, the second proximal end portion 7457 is located within a portion of the sixth guide path 7652 of the first link 5510. Further, the first and second proximal end portions 7456, 7457 are each routed within an instrument shaft (not shown), which is coupled to a housing of a transmission mechanism, such as transmission mechanism discussed above. The first central portion 7493 is between the first distal end portion 7458 and the proximal end portion 7458, and is located within the fifth guide path 7650 of the second link 7610 and within a portion of the connection path 7655. The second central portion 7494 is between the second proximal end portion 7457 and the distal end portion 7458, and is located within the sixth guide path 7652 of the second link 7610 and within a portion of the connection path 7655.

The retention member 7459 is connected to the distal end portion 7458 of the third tension member 7455 and is configured to fit within the retention pocket 7656 such that the distal end portion 7458 of the tension member extends from retention member 7459 and the retention pocket 7656 to be within the connection path 7655. The retention member 7459 is sized such that it is larger than the distal end portion 7458 of the tension member at its connection thereto. Further, the retention member 7459 is sized to fit within the retention pocket 7656 such that the wall 7654 surrounding the connection path 7655 forms a stop to assist with retaining the retention member 7459 within the retention pocket 7656 when tension is applied to the tension member along its longitudinal axis (arrow A-B shown in FIG. 35) for providing pitch movements of the second link 7610 with respect to the first link 5510. Stated differently, the retention member 7459, the retention pocket 7656 and the connection path 7655 are configured such that the retention member is unable to move with the connection path 7655.

Thus, the wrist assembly 7500 is configured to securely retain the third tension member 7455 within the connection path 7655 and the fifth and sixth guide path 7650, 7652 during pitch movements, for example, for angular rotations about the first axis $A_1$ away from the first orientation shown in FIGS. 32 and 35. The retention pocket 7656 securely retains the retention member 7459 therein based on beneficial features, such as interference with stop features like the wall 7654 surrounding a portion of the connection path 7655, as well as the retention pocket 7656 being sized to be larger than the cross-section of the connection path 7655, and the retention member being sized to fit within the retention pocket 7656 and also to be larger than the cross-section of the distal end portion 7458.

In addition, the wrist assembly 7500 is further configured to improve the ease of installing the third tension member 7455 within the wrist assembly 7500 including routing the third tension member 7455 through the second link 7610 and installing the retention member 7459 within the retention pocket 7656 and other features that can provide benefits for retaining the tension member within the second link 7610. Further, the wrist assembly 7500 is configured to reduce the likelihood of the third tension member 7455 being damaged during installation, such as avoiding bends or kinks from forming within the tension member, and reducing the likelihood of cuts and abrasions to the tension member from installation.

Referring to FIGS. 39-42, the instrument 7400 and the wrist assembly 7500 are configured to allow easy installation of the third tension member 7455 and the retention member 7459 therein along with providing the retention benefits described above, as well as to reduce the likelihood of damaging the third tension member 7455 during installation. As illustrated in FIGS. 39-42, the wrist assembly 7500 and the tension member 7455 are configured such that the first proximal end portion 7456 and each of the first and second central portions 7493, 7494 of the third tension member 7455 can be: A) inserted through the assembly path 7691 along the assembly path centerline $CL_2$; and B) the first and second proximal end portions 7456, 7457 and the first and second central portions 7493, 7494 can be rotated until each of the first and second proximal end portions 7456, 7457 is within the corresponding fifth and sixth guide paths 7650, 7652 of the first link 5510 (FIG. 35) and the first and second central portions 7493, 7494 are each within the corresponding fifth and sixth guide paths 7650, 7652, such that the distal end portion 7458 is within the connection path 7655 when assembled.

Figure 40:
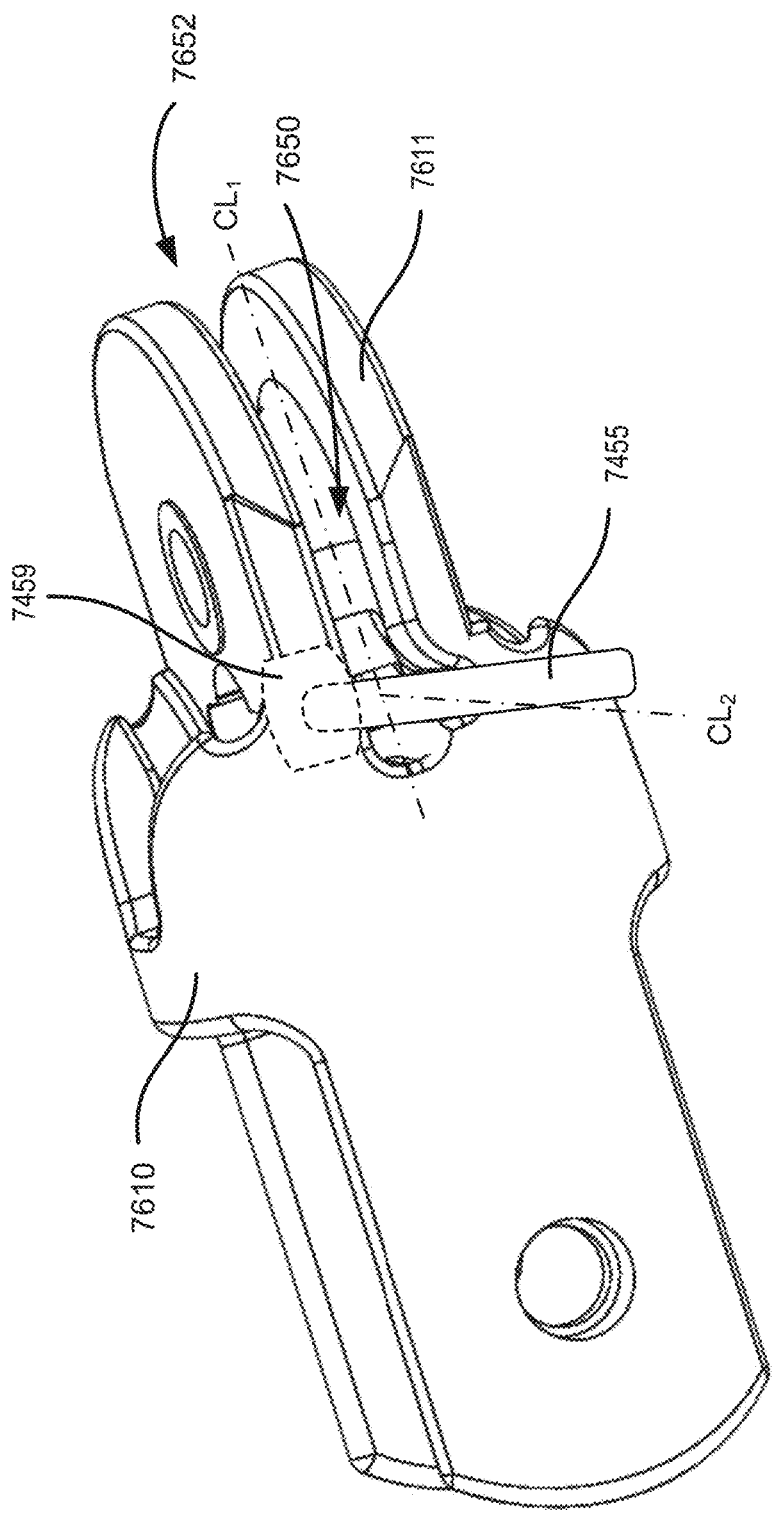

As shown in FIGS. 40 and 42, the third tension member 7455 can be flexed within its range of flexibility based on its modulus of elasticity and other tension member properties at an appropriate bend angle to assist with installation of the tension member while avoiding excessive bending or flexing that can damage the tension member. The third tension member 7455 can be installed by threading the first and second proximal end portions 7456, 7457 and the first and second central portions 7493, 7494 into the second link through the exposed slot opening 7658 of the retention pocket 7656. The bend angle 7495 can be an acute angle as shown in FIG. 42 that flexes the tension member with respect to the retention member 7459 by a small angle to assist with installation while avoiding avoid kinking, permanently bending or otherwise damaging the tension member, such as can occur at much larger bend angles. In some embodiments, the bend angle can be more than the insertion angle 7695. In some embodiments, the bend angle can be the same as the insertion angle 7695, and in some embodiments the bend angled can be less than the insertion angle 7695.

As described above, the assembly path 7691 is configured and oriented with the respect to the retention pocket such that the assembly path is angled away from the connection path 7655 as the paths extend outward from the retention pocket 7656 at the insertion angle 7695. In addition, as shown in FIGS. 39-42, the centerline $CL_3$ of the assembly path can be oriented away from the connection path 7655 such that the assembly path 7691 is aligned as much as possible with the slot opening 7658. As such, an installation path is formed through the slot opening 7658 and the retention pocket 7656, and into and through the angled assembly path 7691, which avoids flexing the third tension member 7455 at large bend angles or through contoured paths to install the tension member within the wrist assembly 7500.

When the third tension member 7455 has been threaded through the assembly path 7691 such that the retention member 7459 is retained and installed within the retention pocket 7656 as shown in FIG. 42, the tension member can be moved from the assembly path 7691 into the connection path 7655 through the open spaced between the two paths. Thus, the third tension member 7455 along with the retention member 7459 can be installed within the wrist assembly 7500 without significantly bending or flexing the tension member or routing it through tight bends that damage the tension member. In some embodiments (not shown), the retention member can be coupled to the distal end portion of the tension after the tension member has been partially installed. Doing so can further avoid excessive bending and flexing of the tension member during installation.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys or the like. Further, any of the links, tool members, tension members, or components described herein can be constructed from multiple pieces that are later joined together. For example, in some embodiments, a link can be constructed by joining together separately constructed components. In other embodiments however, any of the links, tool members, tension members, or components described herein can be monolithically constructed.

Although the instruments are generally shown as having a second axis of rotation $A_2$ that is normal to the first axis of rotation $A_1$, in other embodiments any of the instruments described herein can include a second axis of rotation $A_2$ that is offset from the first axis of rotation $A_1$ by any suitable angle.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

For example, in some embodiments an instrument can include a tension member that is twisted as described above with reference to the instrument 5400 and that also has one or more links (e.g., a first link or a second link) that include and inner guide surface or an outer guide surface as described above with reference to the instrument 3400. Thus, in some embodiments, the instrument can include a wrist assembly that defines a guide surface that can be curved along a longitudinal centerline and that can have a linear surface along a cross-section normal to the longitudinal centerline.

What is claimed is:

1. An apparatus, comprising:
   an instrument shaft, a first link, a second link, a tool member, and a tension member;
   the first link being coupled to the instrument shaft and comprising a first guide path having a centerline;
   the second link comprising a proximal end portion, a distal end portion, and a second guide path, the proximal end portion of the second link being coupled to the first link,
the second link being rotatable relative to the first link about a first axis through an angular range,
the distal end portion of the second link being coupled to the tool member, the tool member being rotatable relative to the second link about a second axis,
the second guide path being located between the tool member and the first guide path; and
the tension member comprising a first tension member portion, a second tension member portion, and a third tension member portion,
the first tension member portion being within the first guide path and parallel to the centerline of the first guide path,
the second tension member portion being coupled to the tool member,
the third tension member portion between the first tension member portion and the second tension member portion in the second link, the third tension member portion being maintained parallel to the centerline of the first guide path throughout the angular range of the second link by the second guide path.

2. The apparatus of claim 1, wherein:
the apparatus includes a pulley coupled to the second link; and
an outer surface of the pulley defines a portion of the second guide path.

3. The apparatus of claim 1, wherein:
the second link includes a wall; and
the wall defines a portion of the second guide path.

4. The apparatus of claim 1, wherein:
the apparatus includes a pulley coupled to the second link;
the second link includes a wall;
the tension member is in contact with an outer surface of the pulley when the second link is at a first angle within the angular range of the second link; and
the tension member is in contact with the wall when the second link is at a second angle within the angular range of the second link different from the first angle.

5. The apparatus of claim 4, wherein:
the apparatus includes a pin, and the pin defines the first axis;
the proximal end portion of the second link is coupled to the first link by the pin; and
the pulley is configured to rotate relative to the second link about the pin.

6. The apparatus of claim 1, wherein:
the instrument shaft has an axial centerline;
the centerline of the first guide path is offset from the axial centerline of the instrument shaft by a first distance;
the second tension member portion is parallel to the axial centerline of the instrument shaft and is offset from the axial centerline of the instrument shaft by a second distance; and
the second distance is less than the first distance.

7. An apparatus, comprising:
an instrument shaft, a first link, a second link, a tool member, and a tension member;
the first link being coupled to the instrument shaft and comprising a first guide path having a centerline;
the second link comprising a proximal end portion, a distal end portion, a second guide path, an inner guide surface, and an outer guide surface,
the proximal end portion of the second link being coupled to the first link,
the second link being rotatable relative to the first link about a first axis through an angular range,
the distal end portion of the second link being coupled to the tool member, the tool member being rotatable relative to the second link about a second axis,
the second guide path being located between the tool member and the first guide path, and
a portion of the second guide path is defined by the inner guide surface and the outer guide surface; and
the tension member comprising a first tension member portion, a second tension member portion, and a third tension member portion between the first tension member portion and the second tension member portion,
the first tension member portion being within the first guide path and parallel to the centerline of the first guide path,
the second tension member portion being coupled to the tool member, and
the third tension member portion being in contact with the inner guide surface throughout a first portion of the angular range of the second link and being in contact with the outer guide surface throughout a second portion of the angular range of the second link.

8. The apparatus of claim 7, wherein:
the third tension member portion is spaced apart from the inner guide surface and in contact with the outer guide surface when the second link is in a first orientation relative to the first link; and
the third tension member portion is spaced apart from the outer guide surface and in contact with the inner guide surface when the second link is in a second orientation relative to the first link different from the first orientation.

9. The apparatus of claim 7, wherein:
the tension member includes a fourth tension member portion between the first tension member portion and the third tension member portion; and
the fourth tension member portion is parallel to the centerline of the first guide path throughout the angular range of the second link.

10. The apparatus of claim 7, wherein:
the inner guide surface of the second link is an outer surface of a pulley coupled to the second link.

11. The apparatus of claim 10, wherein:
the instrument shaft has an axial centerline;
the centerline of the first guide path is offset from the axial centerline of the instrument shaft by an offset distance;
the outer surface of the pulley defines a pulley radius; and
the pulley radius is equal to the offset distance.

12. The apparatus of claim 7, wherein:
the outer guide surface of the second link is a wall of the second link.

13. An apparatus, comprising:
an instrument shaft, a first link, a second link, a tool member, and a tension member;
the first link being coupled to the instrument shaft having an axial centerline and comprising a first guide path having a centerline,
the centerline of the first guide path is offset from the axial centerline of the instrument shaft by an offset distance;
the second link comprising a proximal end portion, a distal end portion, a second guide path, and an inner guide surface,
the proximal end portion of the second link being coupled to the first link, the second link being rotatable relative to the first link about a first axis through an angular range, the distal end portion of the second link being coupled to the tool member, the tool member being rotatable relative to the second link about a second axis, the second guide path being located between the tool member and the first guide path, the inner guide surface defining a portion of the second guide path, and an outer radius of the inner guide surface is equal to the offset distance; and the tension member comprising a first tension member portion, a second tension member portion, and a third tension member portion between the first tension member portion and the second tension member portion, the first tension member portion being within the first guide path and parallel to the centerline of the first guide path, the second tension member portion being coupled to the tool member, and the third tension member portion being in contact with the inner guide surface throughout a portion of the angular range of the second link.

14. The apparatus of claim 13, wherein:
the portion of the second guide path is a first portion of the second guide path;
the second link includes an outer guide surface; and
the outer guide surface defines a second portion of the second guide path.

15. The apparatus of claim 14, wherein:
the portion of the angular range is a first portion of the angular range of the second link; and
the third tension member portion is in contact with the outer guide surface throughout a second portion of the angular range of the second link that is different from the first portion of the angular range.

16. The apparatus of claim 13, wherein:
the second tension member portion is parallel to the axial centerline of the instrument shaft and is offset from the axial centerline of the instrument shaft by a second distance that is less than the offset distance.

17. The apparatus of claim 13, wherein:
the tension member comprises a fourth tension member portion between the first tension member portion and the third tension member portion; and
the fourth tension member portion is parallel to the centerline of the first guide path throughout the angular range of the second link.

18. The apparatus of claim 13, wherein:
the tool member is a first tool member, a third guide path is defined within the first link, a fourth guide path is defined within the second link between a second tool member and the third guide path, the distal end portion of the second link is coupled to the second tool member, and the tension member is a first tension member;
the apparatus further comprises a second tension member having a fifth tension member portion, a sixth tension member portion, and a seventh tension member portion;
the fifth tension member portion is within the third guide path;
the sixth tension member portion is coupled to the second tool member; and
the seventh tension member portion is parallel to a centerline of the third guide path throughout the angular range.

19. An apparatus, comprising:
an instrument shaft, a first link, a second link, a tool member, and a tension member;
the first link being coupled to the instrument shaft having an axial centerline and comprising a first guide path having a centerline,
the centerline of the first guide path is offset from the axial centerline of the instrument shaft by an offset distance;
the second link comprising a proximal end portion, a distal end portion, a second guide path, and an outer guide surface,
the proximal end portion of the second link being coupled to the first link,
the second link being rotatable relative to the first link about a first axis through an angular range,
the distal end portion of the second link being coupled to the tool member, the tool member being rotatable relative to the second link about a second axis,
the second guide path being located between the tool member and the first guide path,
the outer guide surface defining a portion of the second guide path; and
the tension member comprising a first tension member portion, a second tension member portion, a third tension member portion, and a fourth tension member portion,
the first tension member portion being within the first guide path and parallel to the centerline of the first guide path,
the second tension member portion being coupled to the tool member,
the third tension member portion between the first tension member portion and the second tension member portion and being in the second link, the third tension member portion being maintained parallel to the centerline of the first guide path during a portion of the angular range of the second link by a radius of curvature of the outer guide surface.

20. The apparatus of claim 19, wherein:
the portion of the second guide path is a first portion of the second guide path;
the second link includes an inner guide surface; and
the inner guide surface defines a second portion of the second guide path.

21. The apparatus of claim 20, wherein:
the portion of the angular range is a first portion of the angular range of the second link; and
the third tension member portion is maintained parallel to the centerline of the first guide path during a second portion of the angular range of the second link by an outer radius of the inner guide surface.

22. The apparatus of claim 20, wherein:
an outer radius of the inner guide surface is equal to the offset distance.

23. The apparatus of claim 20, wherein:
the third tension member portion is spaced apart from the inner guide surface and in contact with the outer guide surface when the second link is in a first orientation relative to the first link; and
the third tension member portion is spaced apart from the outer guide surface and in contact with the inner guide surface when the second link is in a second orientation relative to the first link different from the first orientation.

24. The apparatus of claim 19, wherein:
the second tension member portion is parallel to the axial centerline of the instrument shaft and is offset from the axial centerline of the instrument shaft by a second distance that is less than the offset distance.

* * * * *